United States Patent
Mazed et al.

(10) Patent No.: US 9,557,271 B2
(45) Date of Patent: Jan. 31, 2017

(54) OPTICAL BIOMODULE FOR DETECTION OF DISEASES

(71) Applicants: Mohammad A. Mazed, Chino Hills, CA (US); Sayeeda Mazed, Yorba Linda, CA (US)

(72) Inventors: Mohammad A. Mazed, Chino Hills, CA (US); Sayeeda Mazed, Yorba Linda, CA (US)

(*) Notice: Subject to any disclaimer, the term of this patent is extended or adjusted under 35 U.S.C. 154(b) by 772 days.

(21) Appl. No.: 13/663,376

(22) Filed: Oct. 29, 2012

(65) Prior Publication Data

US 2013/0338039 A1    Dec. 19, 2013

Related U.S. Application Data

(63) Continuation-in-part of application No. 13/448,378, filed on Apr. 16, 2012, and a continuation-in-part of application No. 13/135,832, filed on Jul. 15, 2011, now abandoned, which is a continuation-in-part of application No. 12/573,012, filed on Oct. 2, 2009, now Pat. No. 8,017,147, application No. 13/663,376, which is a continuation-in-part of application No. 12/238,286, filed on Sep. 25, 2008, now abandoned.

(60) Provisional application No. 61/742,074, filed on Aug. 1, 2012, provisional application No. 61/631,071, filed on Dec. 27, 2011, provisional application No. 61/517,204, filed on Apr. 15, 2011, provisional application No. 61/628,060, filed on Oct. 24, 2011.

(51) Int. Cl.
*G01N 21/64* (2006.01)
*G01N 21/65* (2006.01)
*G01N 27/414* (2006.01)
*B82Y 15/00* (2011.01)

(52) U.S. Cl.
CPC ...... *G01N 21/6454* (2013.01); *G01N 21/6452* (2013.01); *G01N 21/65* (2013.01); *G01N 21/658* (2013.01); *G01N 27/4145* (2013.01); *B82Y 15/00* (2013.01); *Y10S 977/958* (2013.01)

(58) Field of Classification Search
None
See application file for complete search history.

(56) References Cited

U.S. PATENT DOCUMENTS

| | | | | |
|---|---|---|---|---|
| 4,933,147 A * | 6/1990 | Hollar | ..................... | B01L 3/508 356/368 |
| 5,527,712 A * | 6/1996 | Sheehy | ................ | G01N 33/553 422/552 |
| 5,677,196 A * | 10/1997 | Herron | ................. | C08G 65/329 356/244 |
| 6,303,389 B1 * | 10/2001 | Levin | .................. | B01L 3/50255 422/424 |
| 7,799,558 B1 * | 9/2010 | Dultz | ................... | B01J 19/0046 422/401 |

(Continued)

*Primary Examiner* — Chris L Chin

(57) ABSTRACT

An optical biomodule for detecting a disease(s) in a biological fluid (containing a disease specific biomarker(s)) in a fluidic container(s) or on a substrate(s), utilizing an enhanced fluorescence emission (due to integration of three-dimensional (3-D) protruded structure(s)) upon chemical binding of a disease specific biomarker(s) with its corresponding specific disease specific biomarker binder(s) is disclosed. Furthermore, the invention includes spatial multiplexing and optical multiplexing of disease specific biomarker binders.

11 Claims, 41 Drawing Sheets

(56) References Cited

U.S. PATENT DOCUMENTS

| | | | | |
|---|---|---|---|---|
| 7,863,037 B1* | 1/2011 | Dultz | ............... | G01N 33/54373 |
| | | | | 422/403 |
| 7,981,664 B1* | 7/2011 | Dultz | ................... | B01L 3/5085 |
| | | | | 422/407 |
| 8,062,591 B2* | 11/2011 | Yamamoto | ........... | G01N 35/026 |
| | | | | 422/63 |
| 9,012,207 B2* | 4/2015 | Blair | ...................... | B82Y 15/00 |
| | | | | 422/82.11 |

* cited by examiner

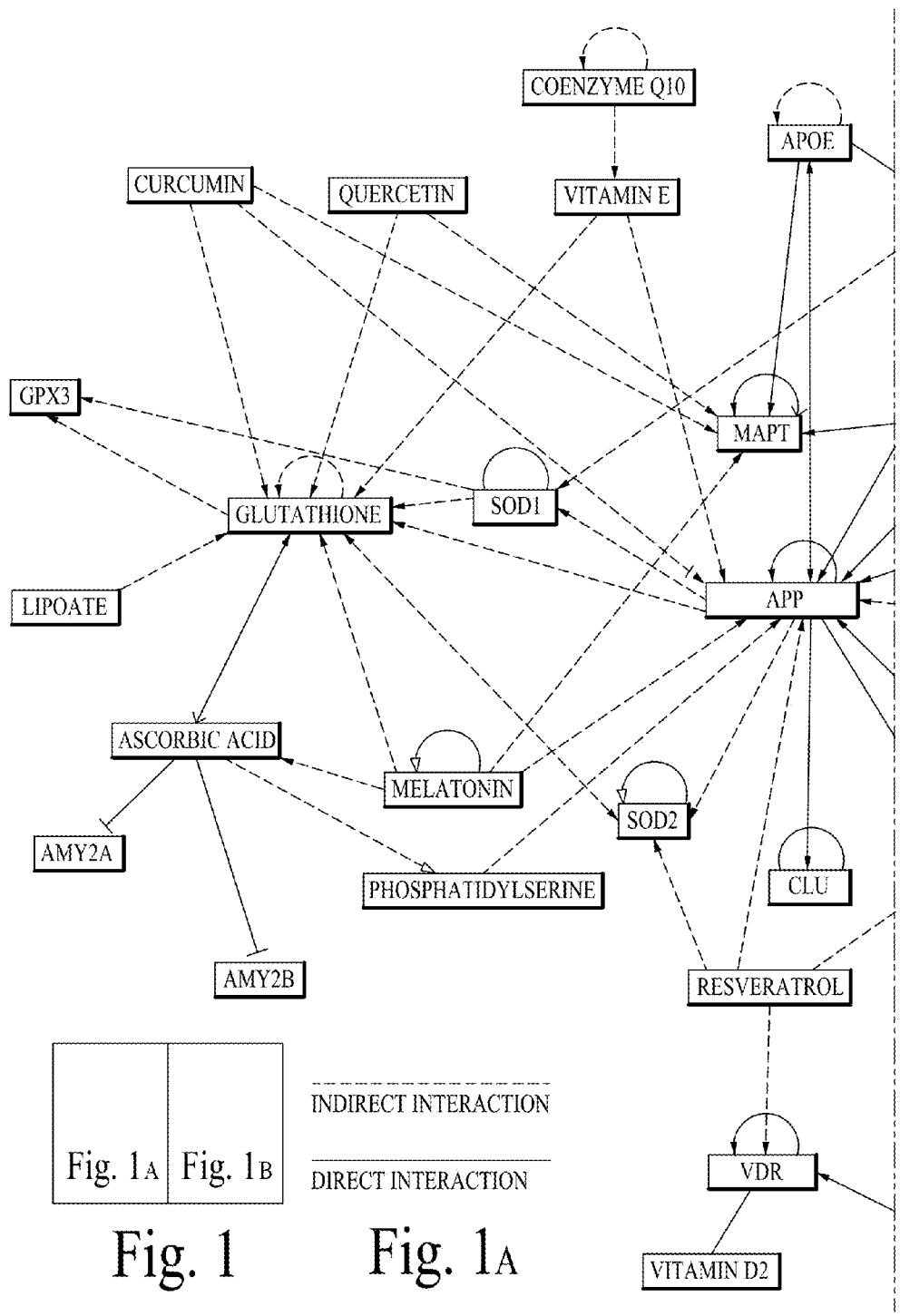

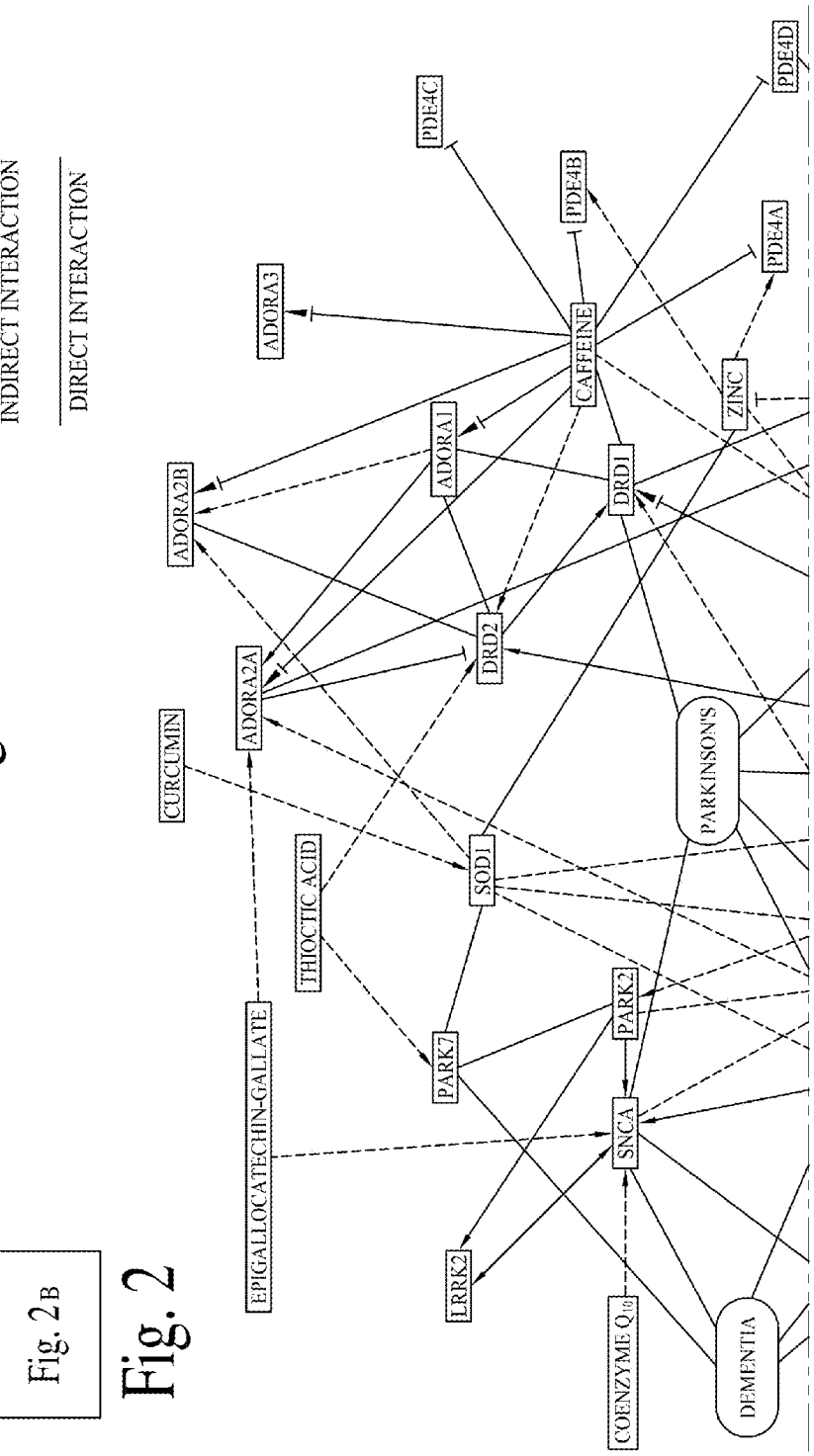

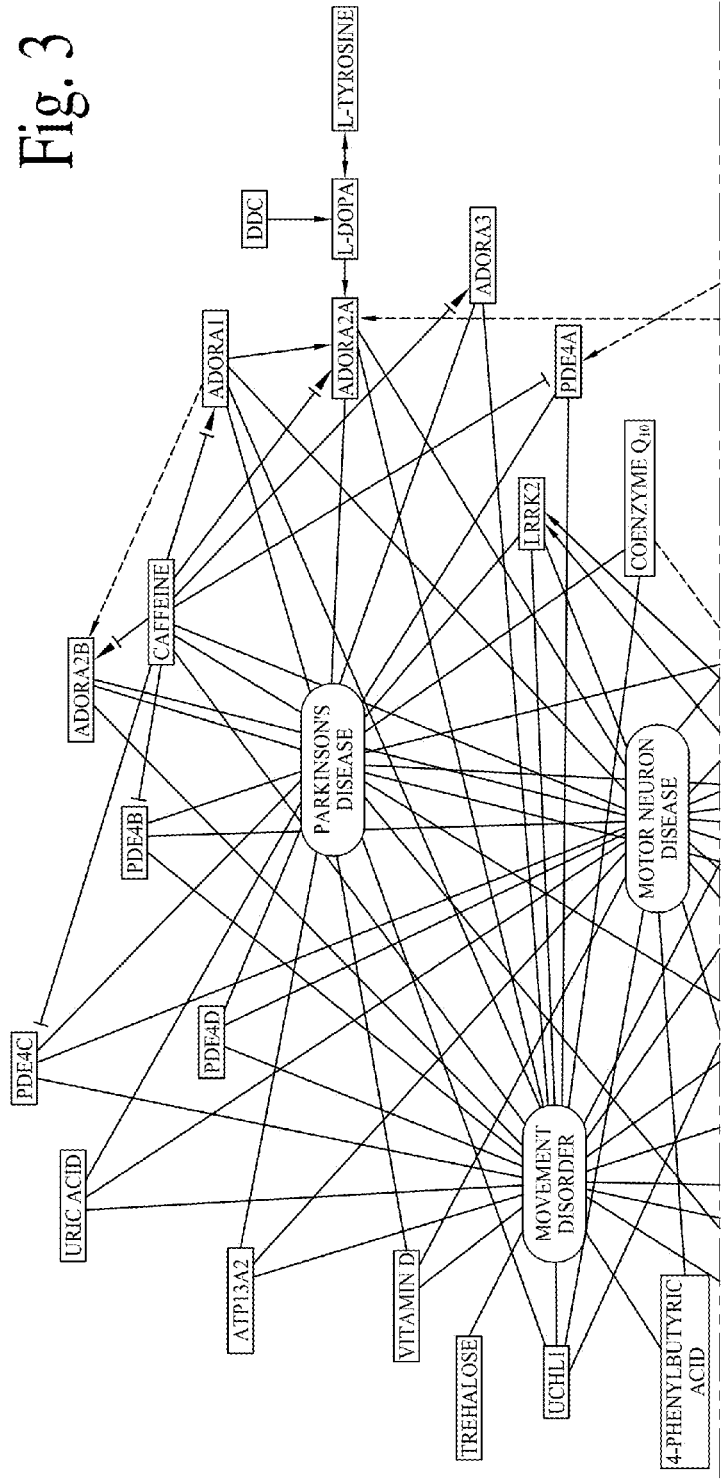

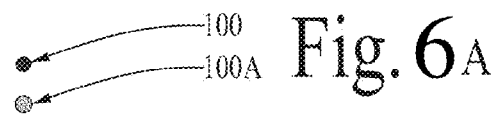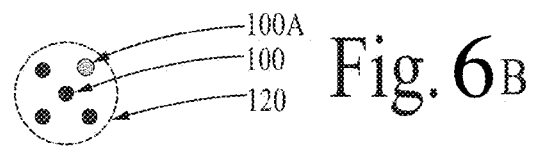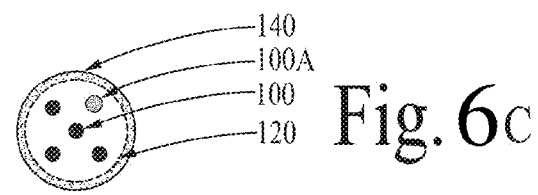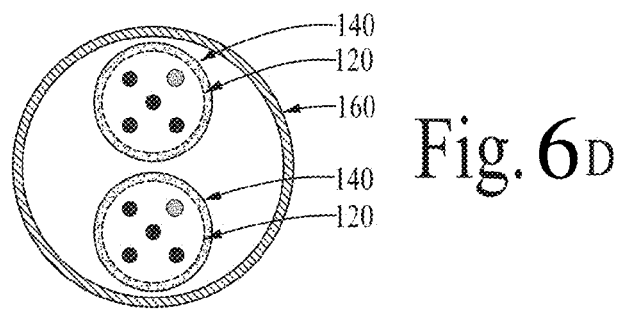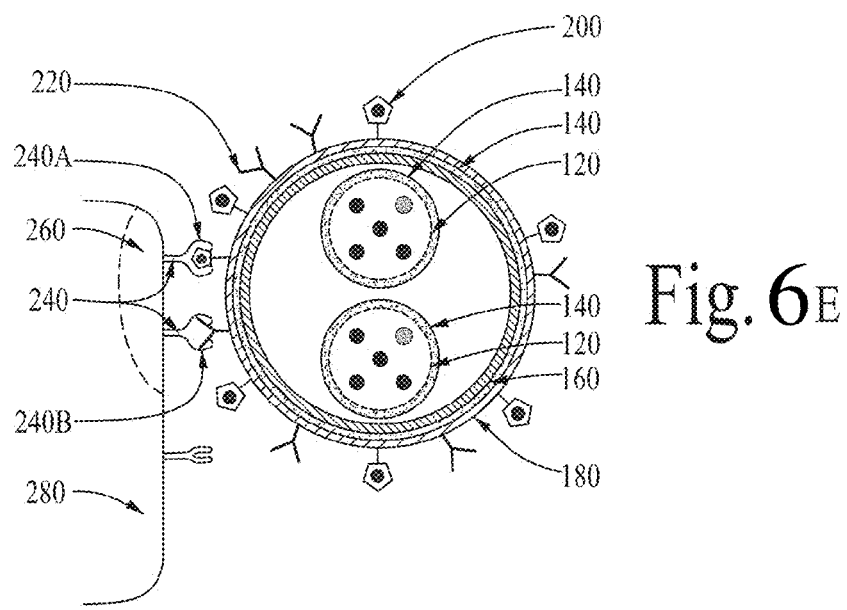

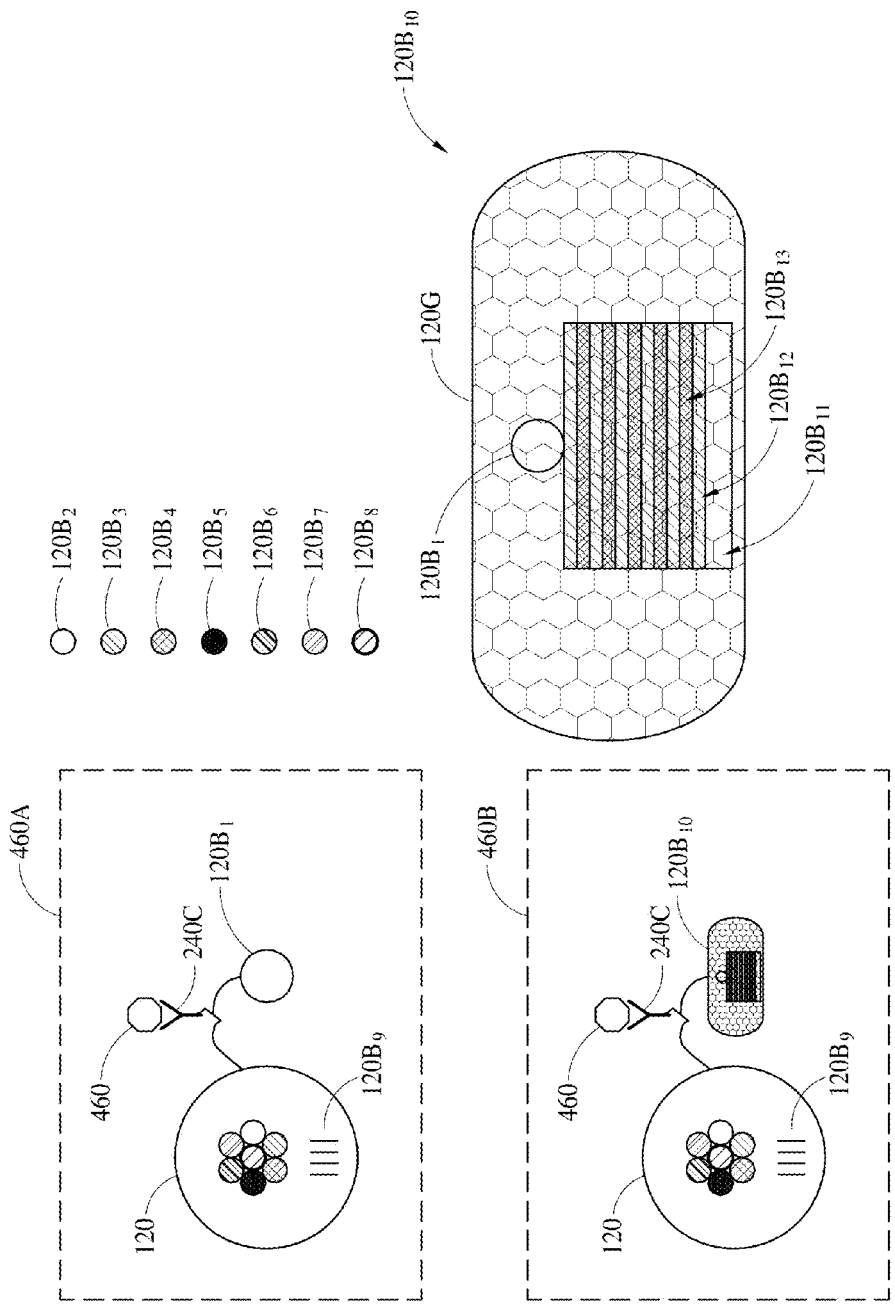
Fig. 12_F

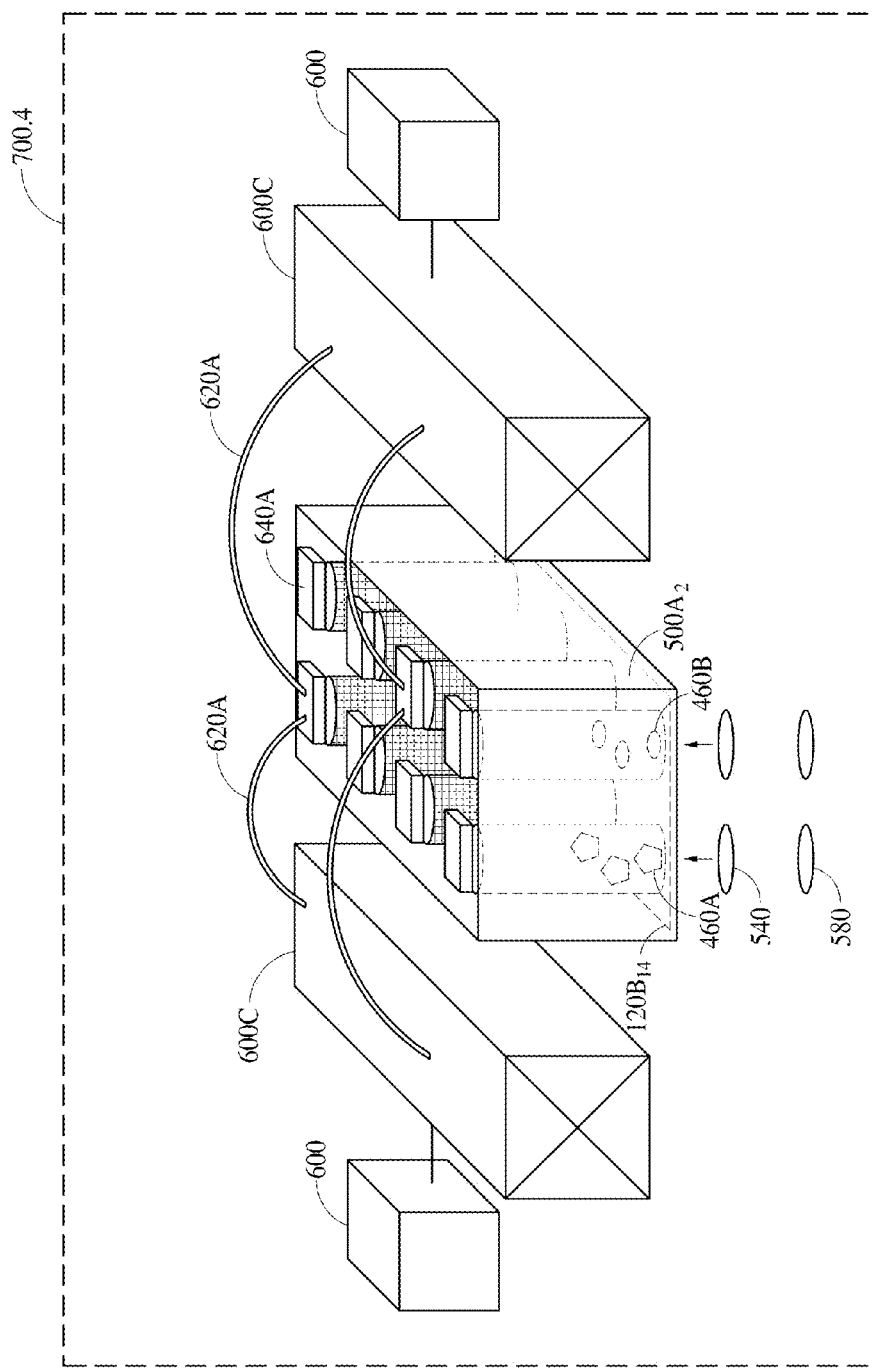
Fig. 12_G

OPTICAL BIOMODULE FOR DETECTION OF DISEASES

CROSS REFERENCE OF RELATED APPLICATIONS

The present application is a continuation-in-part (CIP) of:
(a) U.S. Non-Provisional patent application Ser. No. 13/448,378 entitled "SYSTEM AND METHOD FOR INTELLIGENT SOCIAL COMMERCE", filed on Apr. 16, 2012,
(b) U.S. Non-Provisional patent application Ser. No. 13/135,832 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Jul. 15, 2011,
which is a continuation-in-part (CIP) of U.S. Non-Provisional patent application Ser. No. 12/573,012 entitled, "NUTRITIONAL SUPPLEMENT FOR THE PREVENTION OF CARDIOVASCULAR DISEASE, ALZHEIMER'S DISEASE, DIABETES AND REGULATION AND REDUCTION OF BLOOD SUGAR AND INSULIN RESISTANCE", filed on Oct. 2, 2009 (now as granted U.S. Pat. No. 8017147, issued on Sep. 13, 2011),
(c) U.S. Non-Provisional patent application Ser. No. 12/238,286 entitled, "PORTABLE INTERNET APPLIANCE" filed on Sep. 25, 2008.
The present application also claims priority to:
(a) U.S. Provisional Patent Application No. 61/742,074 entitled "CHEMICAL COMPOSITION AND ITS DELIVERY FOR LOWERING THE RISKS OF ALZHEIMER'S CARDIOVASCULAR AND TYPE-2 DIABETES DISEASES", filed on Aug. 1, 2012,
(b) U.S. Provisional Patent Application No. 61/631,071 entitled "CHEMICAL COMPOSITION AND ITS DELIVERY FOR LOWERING THE RISKS OF ALZHEIMER'S, CARDIOVASCULAR AND TYPE-2 DIABETES DISEASES" filed on Dec. 27, 2011,
(c) U.S. Provisional Patent Application No. 61/628,060 entitled "CHEMICAL COMPOSITION AND ITS DELIVERY FOR LOWERING RISKS OF ALZHEIMER'S, CARDIOVASCULAR AND DISEASES", filed on Oct. 24, 2011,
(d) U.S. Provisional Patent Application No. 61/517,204 entitled "INTELLIGENT SOCIAL E-COMMERCE" filed on Apr. 15, 2011.
The entire contents of all Non-Provisional Patent Applications and Provisional Patent Applications as listed in the previous paragraph are hereby incorporated by reference.

FIELD OF THE INVENTION

The present invention relates to chemical compositions (various embodiments) of bioactive compounds and/or bioactive molecules for lowering the risks of Alzheimer's, Cardiovascular and Diabetes diseases.

The present invention relates to a chemical composition of a sugar free sweetener for people with Type-2 Diabetes disease.

Furthermore, the present invention relates to chemical compositions (various embodiments) of a sugar free super-sweetener for people with Type-2 Diabetes disease.

The present invention relates to targeted (nanoformulation: nanoemulsion/nanodispersion/nanosuspension/nanoencapsulation) deliveries (various embodiments) of bioactive compounds and/or bioactive molecules for lowering the risks of Alzheimer's, Cardiovascular, Diabetes and other diseases.

The present invention relates to passive deliveries (various embodiments) of bioactive compounds and/or bioactive molecules for lowering the risks of Alzheimer's, Cardiovascular, Diabetes and other diseases.

The present invention relates to programmable/active deliveries (various embodiments) of bioactive compounds and/or bioactive molecules for lowering the risks of Alzheimer's, Cardiovascular, Diabetes and other diseases.

The present invention relates to optical diagnostics biomodules (various embodiments) to detect a disease specific biomarker/an array of disease specific biomarkers.

The present invention relates to electrical diagnostics biomodules (various embodiments) to detect a disease specific biomarker/an array of disease specific biomarkers.

The present invention relates to a nanohole based single molecule DNA/RNA sequencing electrical diagnostics biomodule to detect a disease specific biomarker/an array of disease specific biomarkers (by measuring an alteration/elimination of a single molecule of a single stranded DNA/RNA).

The present invention relates to an X-ray fluorescence diagnostics biomodule to detect a disease specific biomarker/an array of disease specific biomarkers.

The present invention relates to a retinal contact lens subsystem biomodule to detect a disease specific biomarker/an array of disease specific biomarkers.

Furthermore, the present invention relates to a retinal contact lens subsystem biomodule for a programmable/active delivery of bioactive compounds and/or bioactive molecules.

The present invention relates to integrated bioelectronics subsystems (various embodiments) to detect a disease specific biomarker/an array of disease specific biomarkers and deliver (programmable/active) bioactive compounds and/or bioactive molecules.

BACKGROUND OF THE INVENTION

One of the most intriguing discoveries is that many risk factors for Cardiovascular, Type-1 Diabetes and Type-2 Diabetes diseases can be risk factors for Alzheimer's disease (also known as Type-3 Diabetes disease).

High blood cholesterol levels are important risk factors for Alzheimer's disease. If blood flow is restricted because of plaque accumulation/buildup in a human brain, less oxygen gets to a human brain and fewer waste residues leave a human brain.

Type-1 Diabetes disease can be caused by autoimmune destruction of insulin-producing cells in the pancreas, resulting in high blood sugar.

The drugs that block effector-memory T cells can delay and/or prevent Type-1 Diabetes disease.

Type-2 Diabetes disease can be linked to excessive iron, diseased pancreas and metabolic syndrome/obesity-hence macrophages in fat tissues. The macrophages in fat tissues produce cytokine molecules, which can cause inflammations in the pancreas.

Such inflammations in the pancreas can increase the insulin (a hormone needed to convert carbohydrates, foods and glucose into energy needed for daily life) resistance and gradually the pancreas loses its ability to produce insulin.

Type-2 Diabetes disease is marked by high levels of blood glucose resulting from defects in glucose production and/or glucose inaction and/or insulin production and/or insulin inaction.

Type-2 Diabetes disease and obesity can be linked with cryptochrome, a protein. Cryptochrome can regulate/modulate/synchronize the biological clock and glucose level in a human body.

An increased level of cryptochrome can suppress/inhibit the production of enzymes (in the liver) for glucose generation during fasting (gluconeogenesis).

Bioactive compounds and/or bioactive molecules that enhance the activity of calcineurin/NFAT can be effective against Type-2 Diabetes, wherein the beta cells do not produce enough insulin.

Both Type-1 Diabetes and Type-2 Diabetes diseases can lead to serious complications (e.g., high blood pressure, kidney disease and premature death).

But people with Type-1 Diabetes and Type-2 Diabetes diseases can control/manage the diseases to lower the risks of serious complications.

The risk of Alzheimer's disease can be linked with obesity and Type-2 Diabetes disease.

A human brain has a low antioxidant level and requires a large volume of blood pumped through it to function properly.

The biochemical reaction of glucose (in blood) with proteins is known as glycation.

Glycation can cause problems in a human brain. The glucose molecule can be splitted/divided open by enzymes for energy consumption in a human brain and two (2) reactive aldehydes can crosslink with proteins in a human brain—thus leading to a decreased blood flow.

Another possible link is leptin, a hormone. Leptin is released by fat cells in a human body and acts on the leptin receptors in a human brain to regulate hunger. There are a number of leptin receptors all over a human body including in the hypothalamus of a human brain.

Higher level of leptin can suppress appetite and enhance metabolism.

Leptin also plays a key role in modulating insulin.

But obesity can create leptin resistance—thus leptin is not transported efficiently in a human brain.

Higher level of leptin in a human brain may lower risk of developing Alzheimer's disease. Leptin can also reduce the production of amyloid beta (Aβ) protein, wherein amyloid beta (Aβ) protein is involved in Alzheimer's disease.

SUMMARY OF THE INVENTION

The present invention relates to chemical compositions (various embodiments) of bioactive compounds for lowering the risks of Alzheimer's, Cardiovascular and Diabetes diseases.

The present invention relates to a chemical composition of a sugar free sweetener for people with Type-2 Diabetes disease.

The present invention relates to chemical compositions (various embodiments) of a sugar free super-sweetener for people with Type-2 Diabetes disease.

The present invention relates to targeted (nanoformulation: nanoemulsion/nanodispersion/nanosuspension/nanoencapsulation) deliveries (various embodiments) of bioactive compounds and/or bioactive molecules.

The present invention relates to passive deliveries (various embodiments) of bioactive compounds and/or bioactive molecules.

The present invention relates to programmable/active deliveries (various embodiments) of bioactive compounds and/or bioactive molecules.

The present invention relates to an array of photonic crystal cavities based integrated optical diagnostics biomodule to detect a disease specific biomarker/an array of disease specific biomarkers.

The present invention relates to (an array of microcapillaries based) integrated optical diagnostics biomodules (various embodiments) to detect a disease specific biomarker/an array of disease specific biomarkers.

The present invention relates to (an array of microcapillaries based) integrated optical diagnostics biomodules (various embodiments) to detect up to two (2) million or more disease specific biomarkers.

The present invention relates to (a field-effect transistor (FET) based) integrated electrical diagnostics biomodules (various embodiments) to detect a disease specific biomarker/an array of disease specific biomarkers.

The present invention relates to a nanohole based single molecule DNA/RNA sequencing electrical diagnostics biomodule to detect a disease specific biomarker/an array of disease specific biomarkers (by measuring an alteration/elimination of a single molecule of the single stranded DNA/RNA).

The present invention relates to integrated bioelectronics subsystems (various embodiments) to detect a disease specific biomarker/an array of disease specific biomarkers and deliver (programmable/active) bioactive compounds and/or bioactive molecules.

The present invention relates to an x-ray fluorescence diagnostics biomodule for detection of a disease specific biomarker/an array of disease specific biomarkers.

The present invention relates to a retinal contact lens subsystem to detect a disease specific biomarker/an array of disease specific biomarkers.

The present invention relates to a retinal contact lens subsystem to deliver (programmable/active) bioactive compounds and/or bioactive molecules.

Embodiments described in the previous paragraphs can be applied/utilized to Alzheimer's, Cardiovascular and Diabetes diseases.

For example: a high level of tau protein in the spinal fluid (also found in a human brain) can indicate Alzheimer's disease about 15 years before Alzheimer's symptoms appear.

For example: low levels of HDL cholesterol and glutathione peroxidase (GPx3) enzyme biomarker can indicate Cardiovascular disease (including heart attack and stroke).

For example: low level of adiponectin and high levels of C-reactive protein CRP, interleukin-1 receptor antagonist and ferritin can indicate Diabetes disease in men.

For example: low level of adiponectin and high levels of apoB, C-reactive protein (CRP) and insulin can indicate Diabetes disease in women.

Alternatively in a related application, utilizing aptamer-conjugated fluorescence resonance energy transfer (FRET), one can assess the levels and enzymatic activity of telomerase, a key oncogene, which is upregulated in many tumors leading to their immortalization due to aberrant continuous maintenance of the chromosomal telomeric repeats.

The complexity of any disease suggests that there would not necessarily be just one biomarker, but a set of key biomarkers (signatures) in varying degrees would be needed to characterize (also utilizing mathematical analysis) a state of a disease.

The mathematical analysis may include: statistical analysis (e.g., Student t-test, ANOVA (analysis of variance) and Chi-Square), data mining analysis (e.g., ANN (artificial neural network), Hierarchical cluster analysis and KNN (K-nearest neighbor analysis) and performance analysis (e.g., specificity, sensitivity and accuracy).

BRIEF DESCRIPTION OF THE TABLES AND FIGURES

The present invention is better understood upon consideration of the description in conjunction with the following tables and drawings.

Table-1 illustrates a composition of a mixture of micronutrients.

Table-2A illustrates a composition of a mixture of antioxidants.

Table-2B illustrates a composition of a mixture of antioxidants.

Table-3A illustrates a composition of a multi-serve antioxidant liquid.

Table-3B illustrates a composition of a single-serve antioxidant liquid.

Table-3C illustrates a composition of a single-serve antioxidant liquid.

Table-3D illustrates a composition of a mixture of botanicals.

Table-3E illustrates a composition of a mixture of electrolytes and dextrose.

Table-4 illustrates a composition of a mixture for expression of beneficial $NrF_2$ protein.

Table-5 illustrates molecular docking score with mTOR, utilizing computational chemistry software.

Table-6A illustrates a composition of a mixture for suppressing/inhibiting mTOR.

Table-6B illustrates a composition of a mixture for suppressing/inhibiting mTOR.

Table-6C illustrates a composition of a mixture for suppressing/inhibiting mTOR.

Table-6D illustrates a composition of a mixture for suppressing/inhibiting mTOR.

Table-7A illustrates a composition of a mixture for lowering the risks of Alzheimer's disease.

Table-7B illustrates a composition of a mixture for lowering the risks of Alzheimer's disease.

Table-7C illustrates a composition of a mixture for lowering the risks of Alzheimer's disease.

Table-7D illustrates a composition of a mixture for lowering the risks of Alzheimer's disease.

Table-8 illustrates a composition of a mixture for lowering the risks of Cardiovascular disease.

Table-9A illustrates a composition of a mixture for lowering the risks of Type-2 Diabetes disease.

Table-9B illustrates a composition of a mixture for lowering the risks of Type-2 Diabetes disease.

Table-10 illustrates a composition of a mixture of sugar free sweetener for people with Type-2 Diabetes disease.

Table-11A, Table-11B, Table-11C, Table-11D, Table-11E, Table-11F, Table-11G, Table-11H, Table-11I, Table-11J, Table-11K, Table-11L and Table-11M, wherein each table illustrates a composition of a mixture of sugar free supersweetener for people with Type-2 Diabetes disease.

FIGS. 1A and 1B illustrate interactions of Alzheimer's disease related genes/proteins with a set of bioactive compounds (e.g., an antioxidant, enzymatic antioxidant, enzyme, micronutrient (mineral/vitamin) and drug) and/or bioactive molecules (e.g, enzyme molecule, protein molecule, small molecule, therapeutic molecule, DNA, gene, ribozyme, RNA, messenger RNA (m-RNA), micro RNA (mi-RNA) and small interfering RNA (s-RNAi)).

FIGS. 2A and 2B illustrate interactions of Alzheimer's, Dementia and Parkinson's disease related genes/proteins with a set of bioactive compounds and/or bioactive molecules.

FIGS. 3A and 3B illustrate interactions of Alzheimer's, Dementia and Parkinson's disease related genes/proteins with a set of bioactive compounds and/or bioactive molecules.

FIGS. 6A, 6B, 6C, 6D and 6E illustrate targeted delivery of bioactive compounds and/or bioactive molecules, utilizing a nanocarrier and/or nanoshell.

FIGS. 11A, 11B, 11C and 11D (an array of microcapillaries based) integrated optical diagnostics biomodules (various embodiments) to detect a disease specific biomarker/an array of disease specific biomarkers.

Figure 12A:
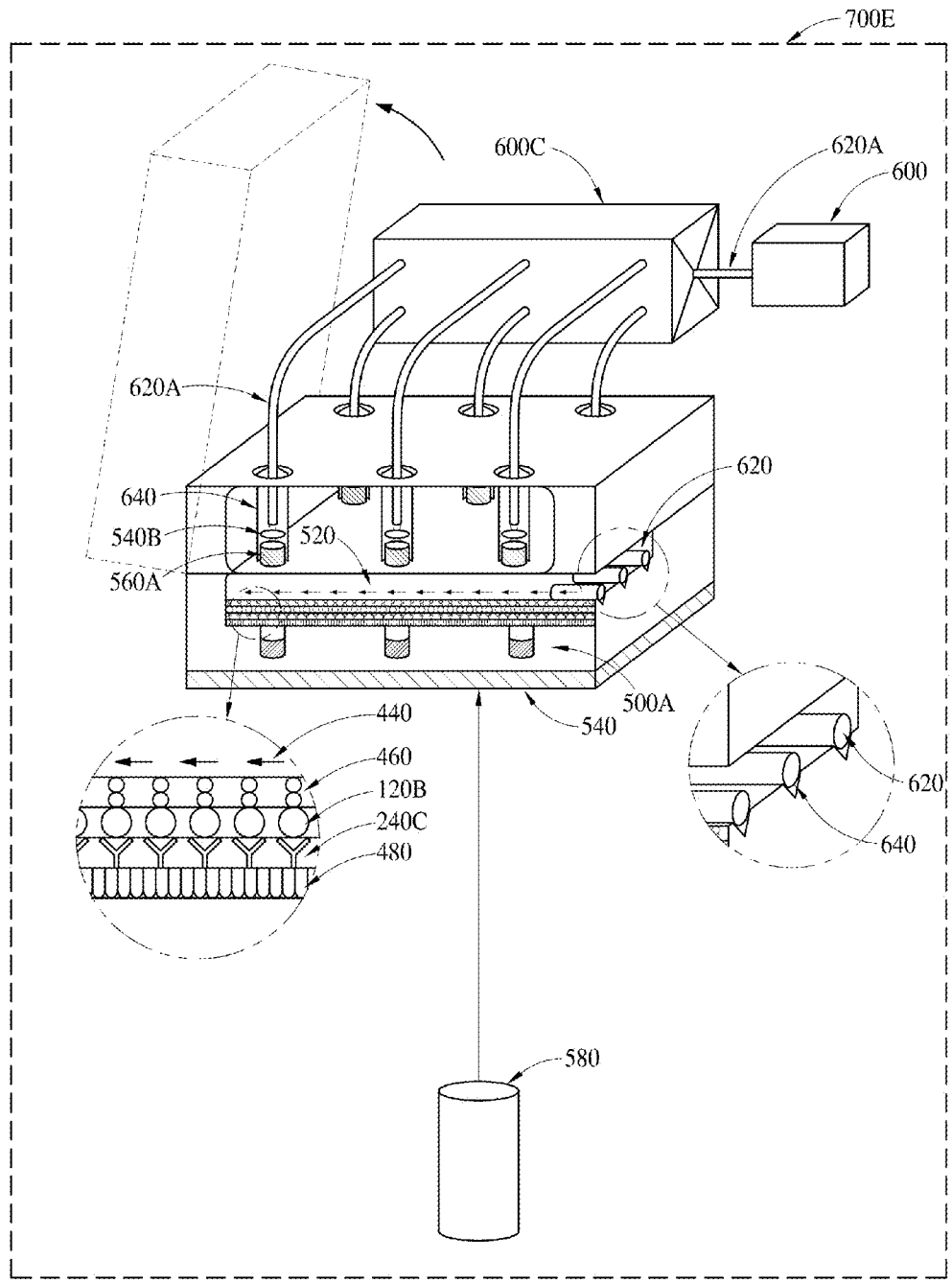
Figure 12B:
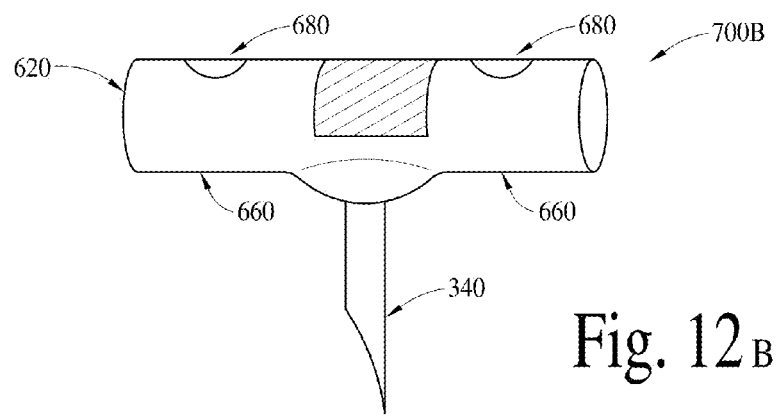
Figure 12C:
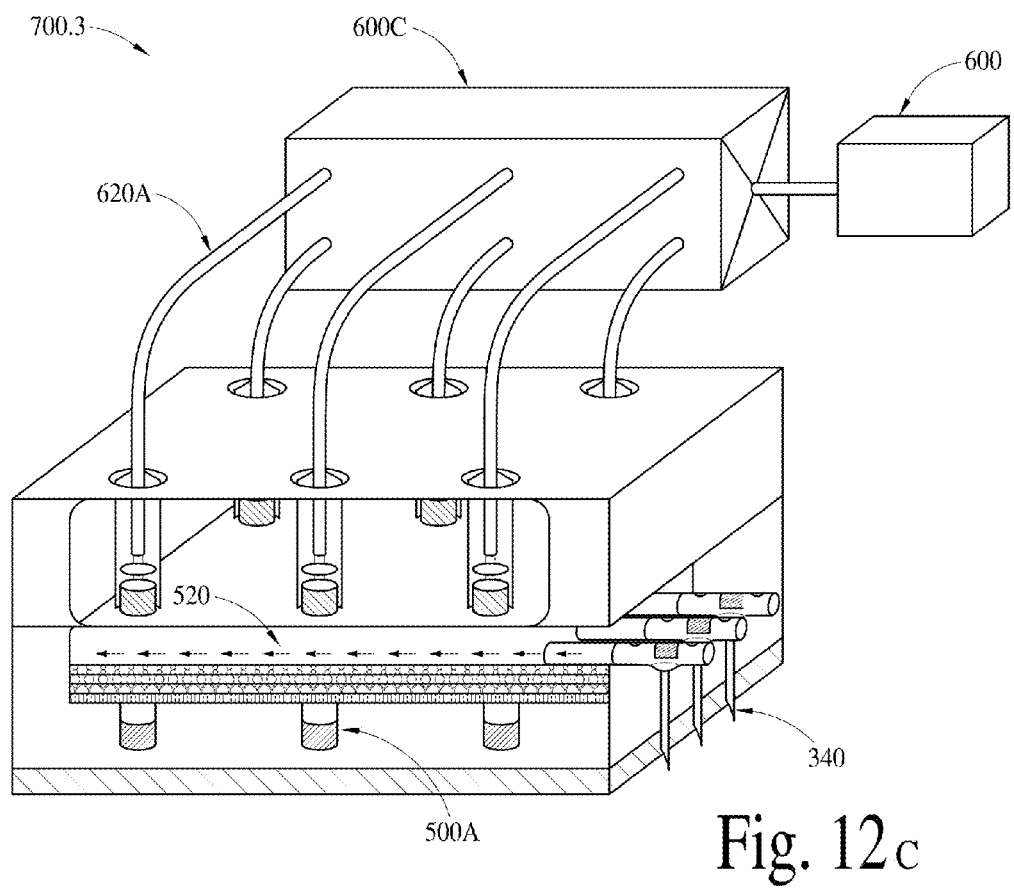

FIGS. 12A, 12B and 12C illustrate an array of microcapillaries based integrated optical diagnostics biomodules (various embodiments) to detect a disease specific biomarker/an array of disease specific biomarkers.

FIGS. 12D, 12E, 12F and 12G illustrate (an array of microcapillaries based) integrated optical diagnostics biomodules (various embodiments) to detect up to two (2) million or more disease specific biomarkers.

Figure 13A:
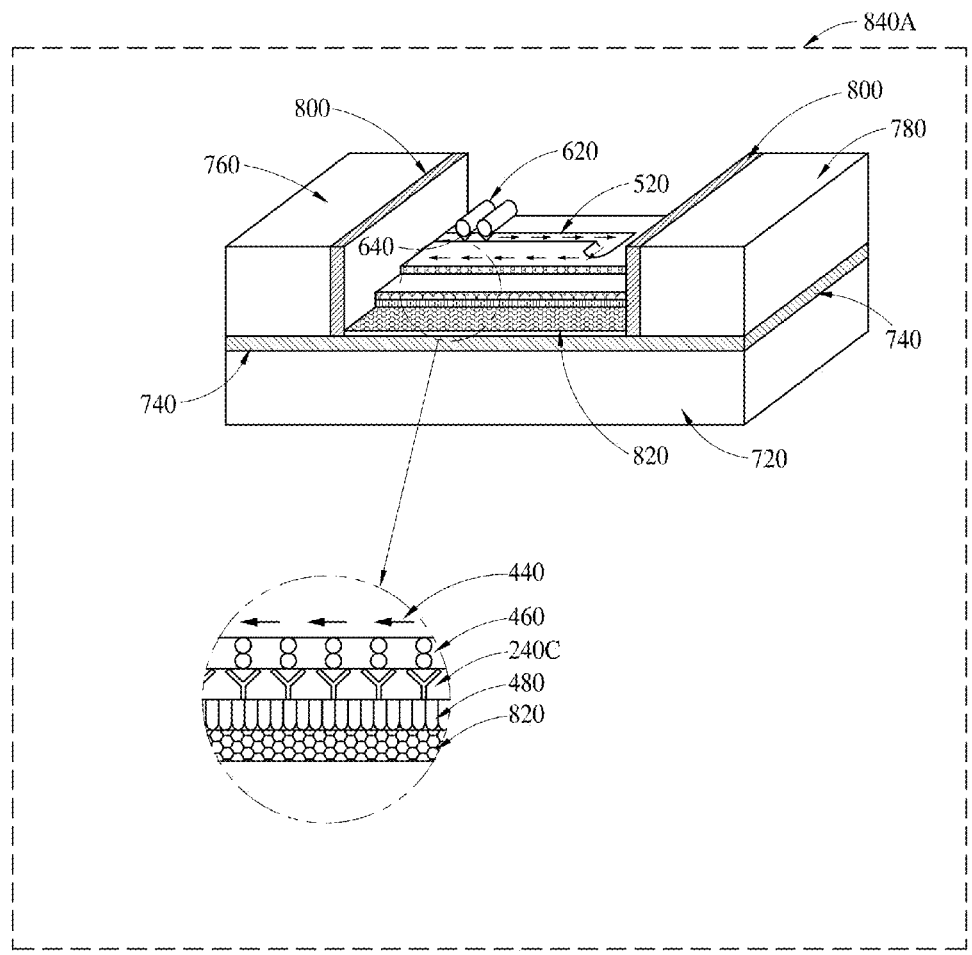
Figure 13B:
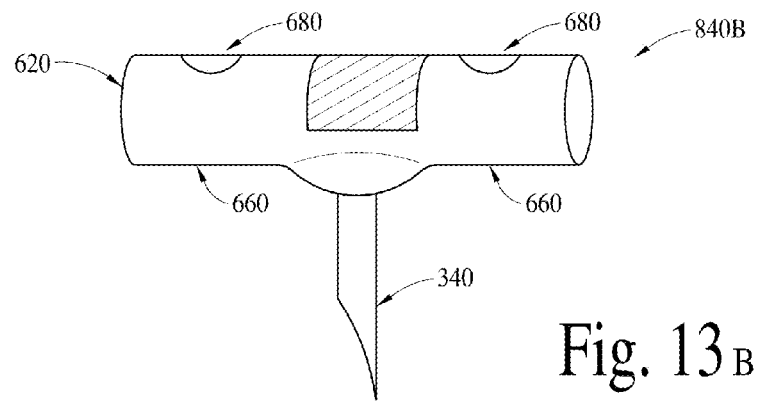
Figure 13C:
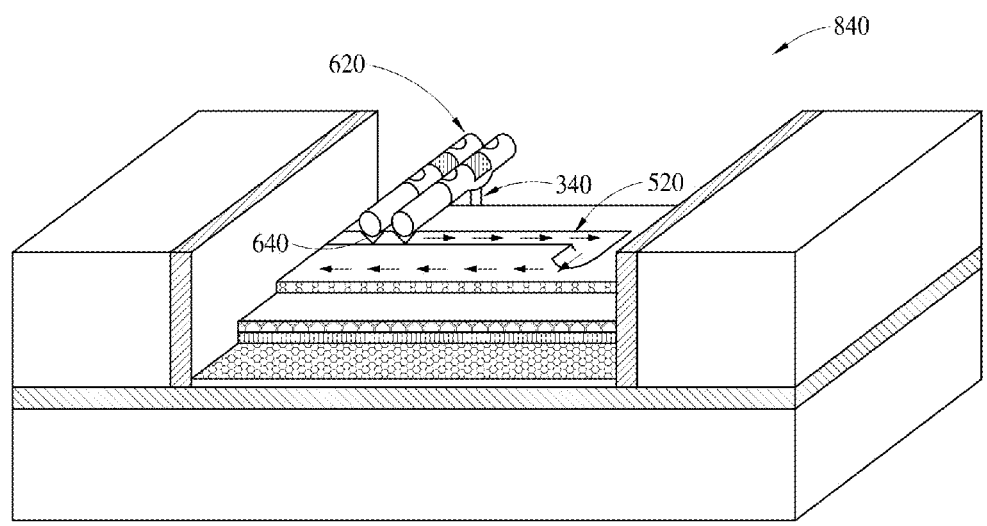

FIGS. 13A, 13B and 13C illustrate (a two-dimensional (2-D) crystal based field-effect transistor (FET) based) integrated electrical diagnostics biomodules (various embodiments) to detect a disease specific biomarker/an array of disease specific biomarkers.

Figure 13D:
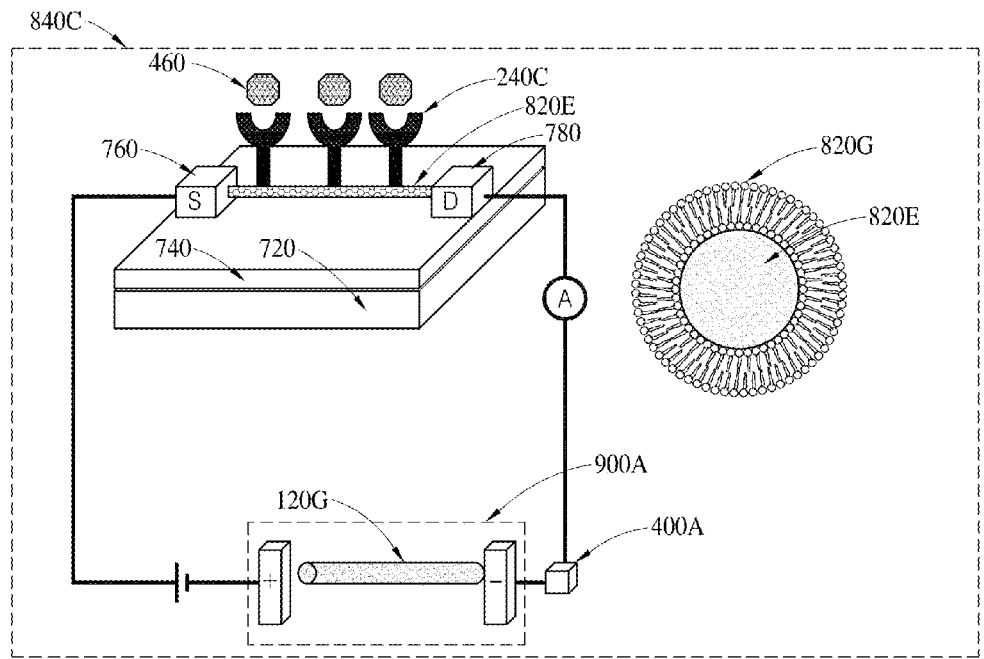

FIG. 13D illustrates chitosan/melanin based proton field-effect transistor ($H^+$ FET) integrated with a lipid layer and a nanotransmitter to detect a disease specific biomarker/an array of disease specific biomarkers.

Figure 13E:
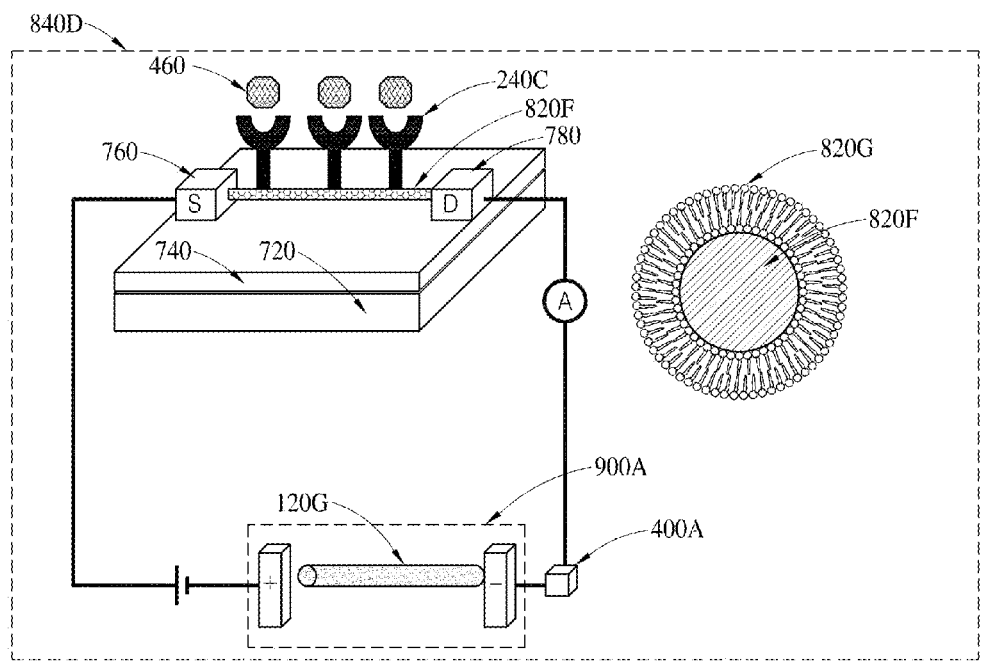

FIG. 13E illustrates a silicon nanowire based field-effect transistor integrated with a lipid layer and a nanotransmitter to detect a disease specific biomarker/an array of disease specific biomarkers.

Furthermore, 13D or 13E can replace the two-dimensional (2-D) crystal based field-effect transistor (FET) in FIG. 13A.

Figure 14A:
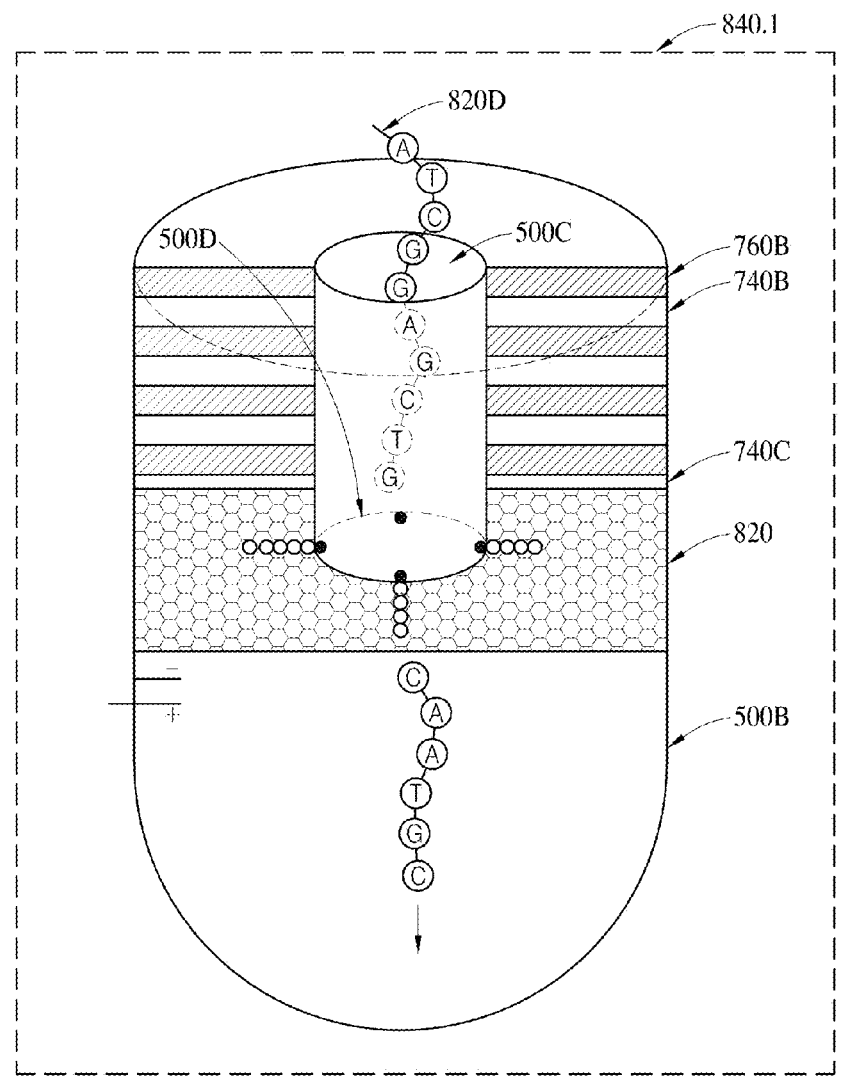
Figure 14B:
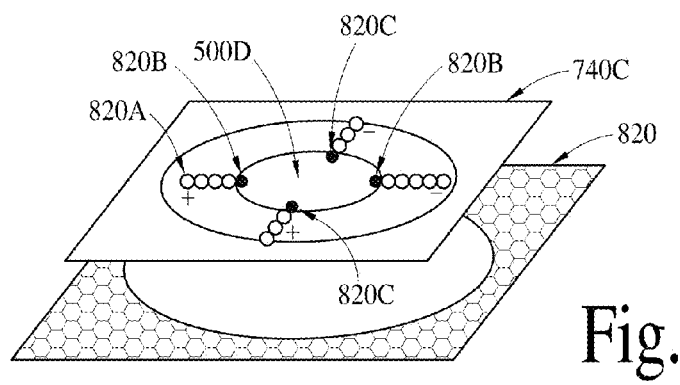

FIGS. 14A and 14B illustrate a nanohole based single molecule DNA/RNA sequencing electrical diagnostics biomodule to detect a disease specific biomarker/an array of disease specific biomarkers (by measuring an alteration/elimination of a single molecule of the single stranded DNA/RNA).

Figure 15A:
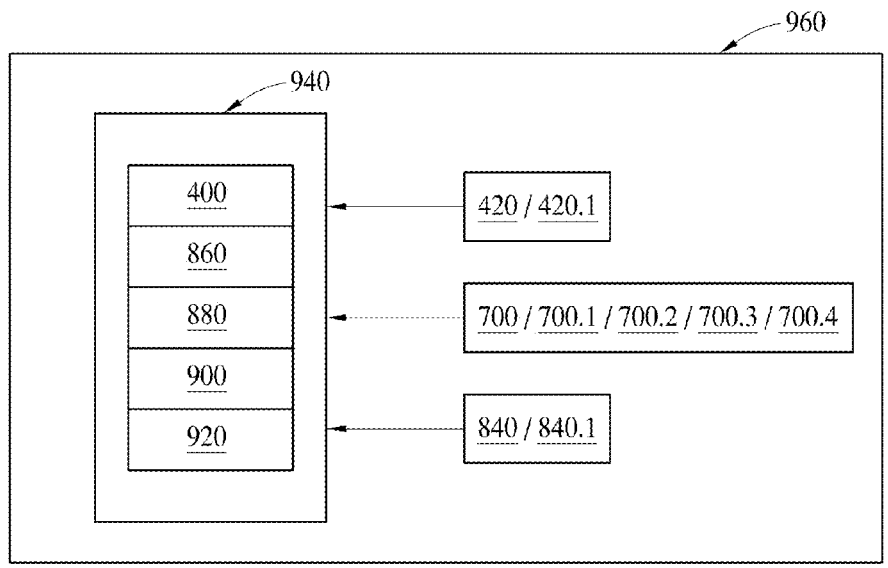

FIG. 15A illustrates integrated bioelectronics subsystems (various embodiments) to detect a disease specific biomarker/an array of disease specific biomarkers and deliver (programmable/active) bioactive compounds and/or bioactive molecules.

Figure 15B:
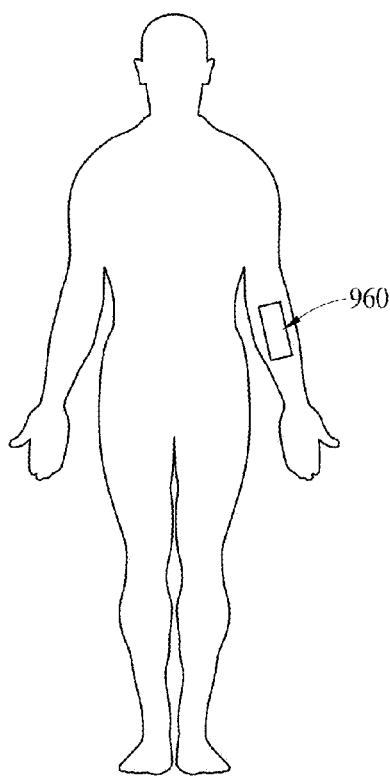

FIG. 15B illustrates a near real-time/real-time application of the wearable integrated bioelectronics subsystem in FIG. 15A.

Figure 16A:
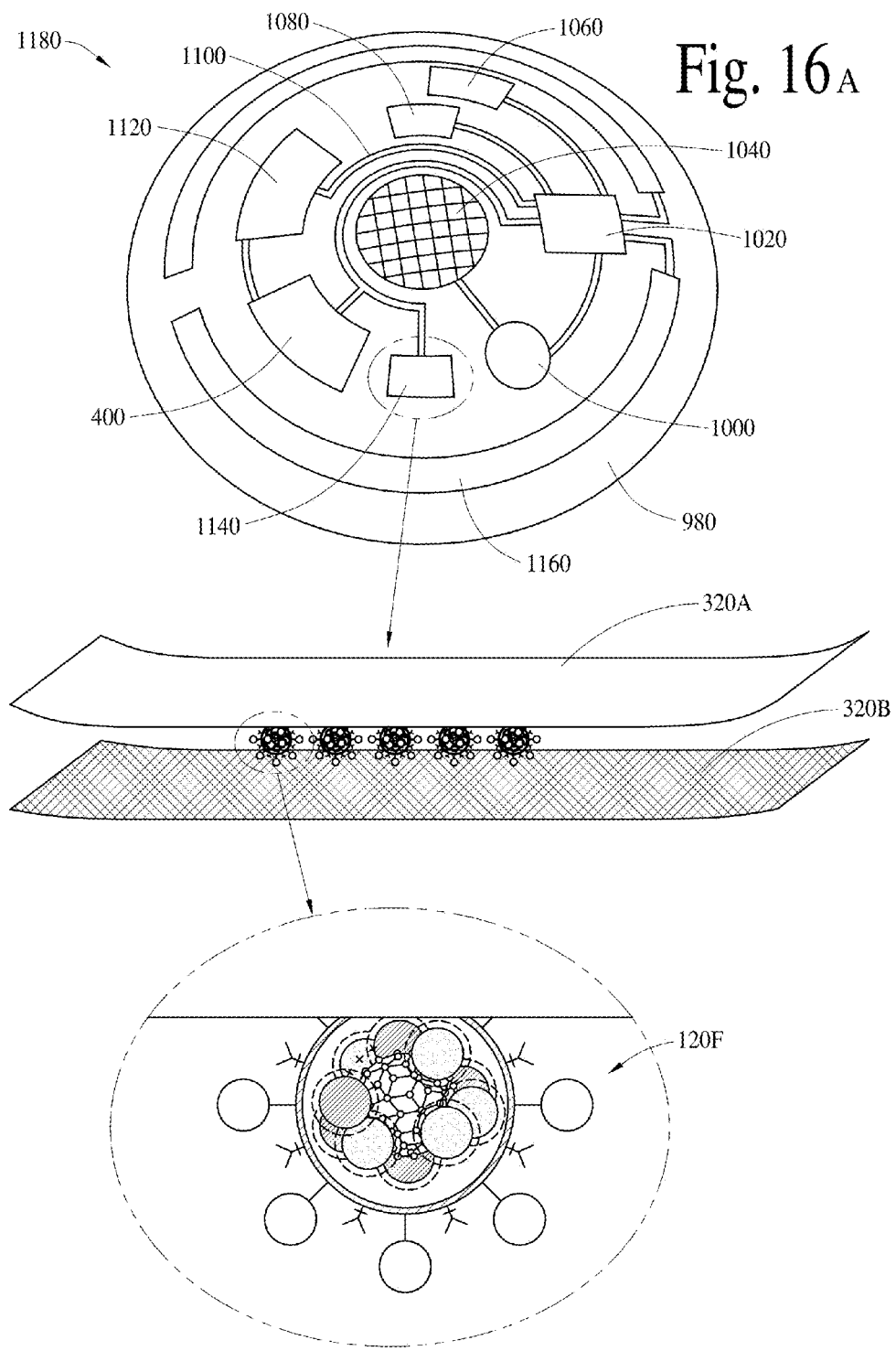

FIG. 16A illustrates a retinal contact lens subsystem to detect a disease specific biomarker/an array of disease specific biomarkers and deliver (programmable/active) bioactive compounds and/or bioactive molecules.

Figure 16B:
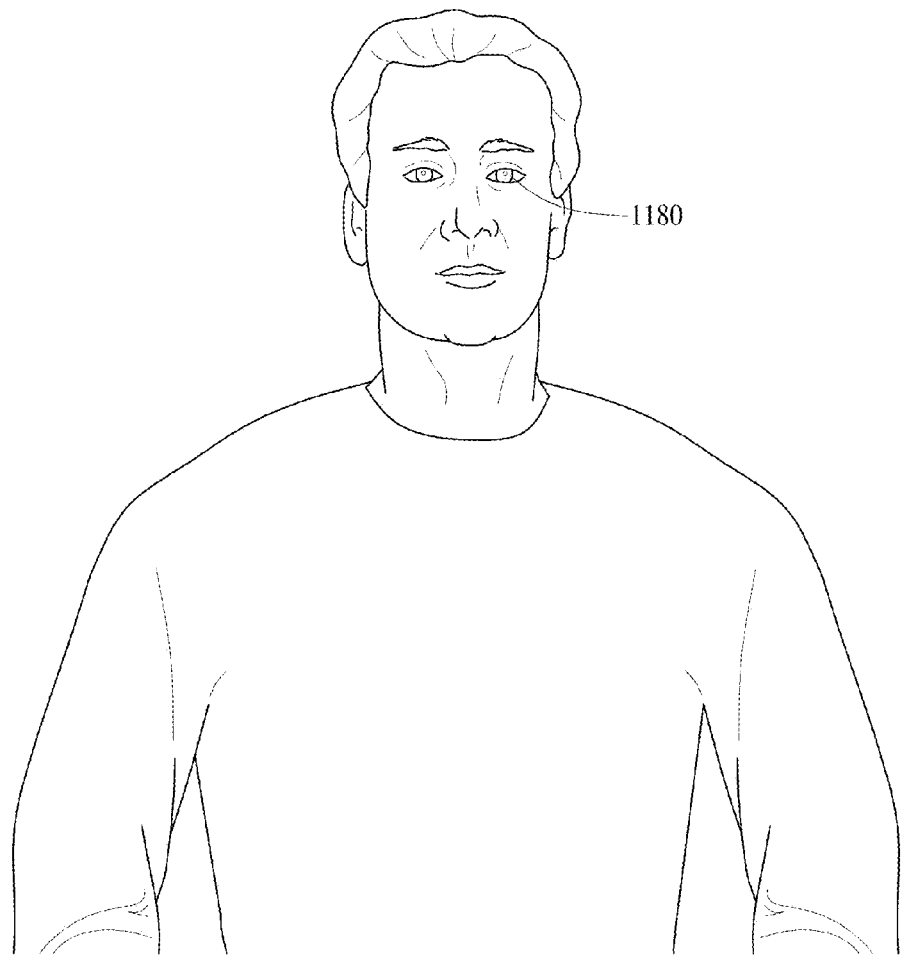

FIG. 16B illustrates a near real-time/real-time application of the wearable retinal contact lens subsystem in FIG. 16A.

DETAIL DESCRIPTION OF THE INVENTION

Bioactive Compounds &/Or Bioactive Molecules Interactions With Genes/Proteins

Figure 1B:
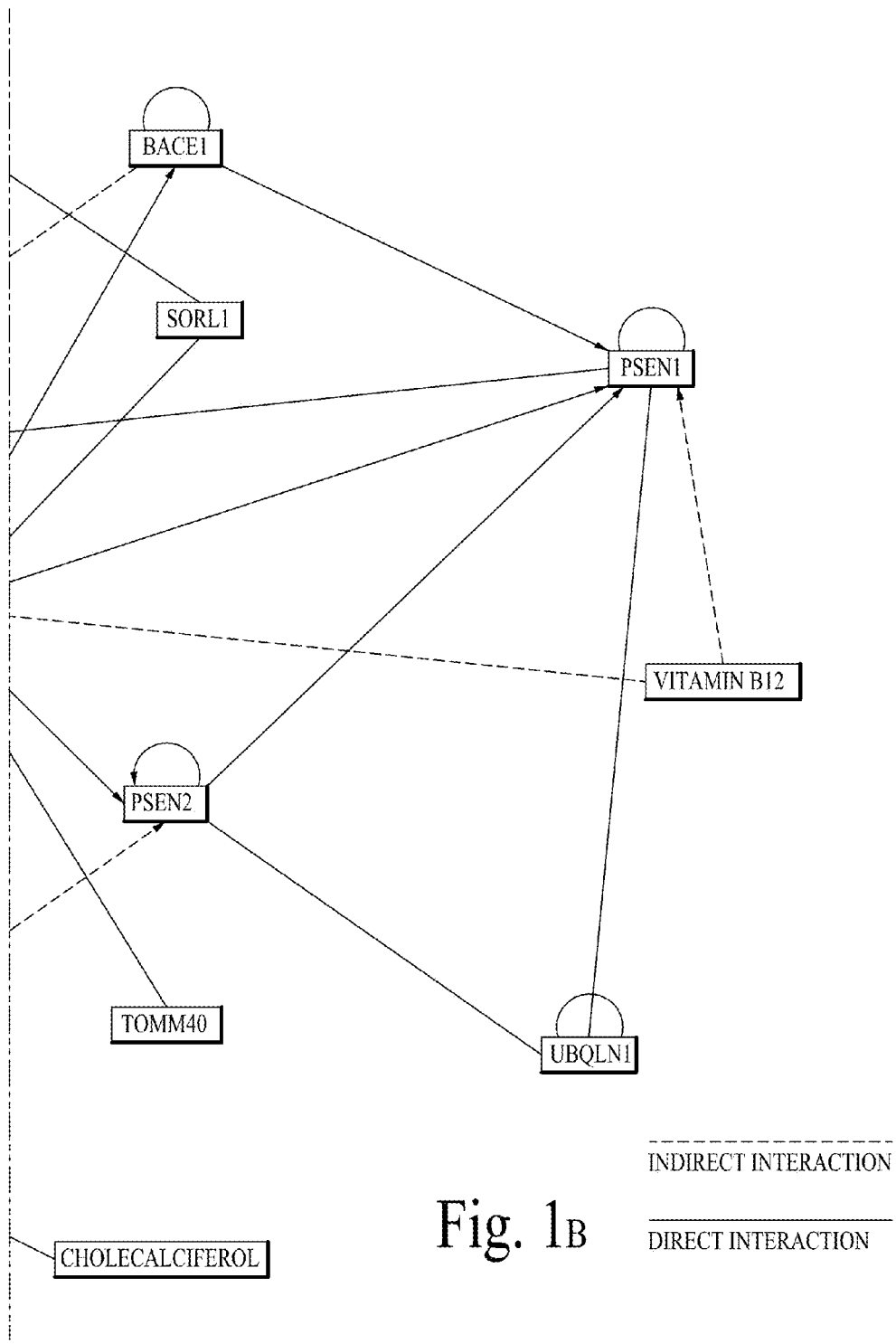
Figure 2B:
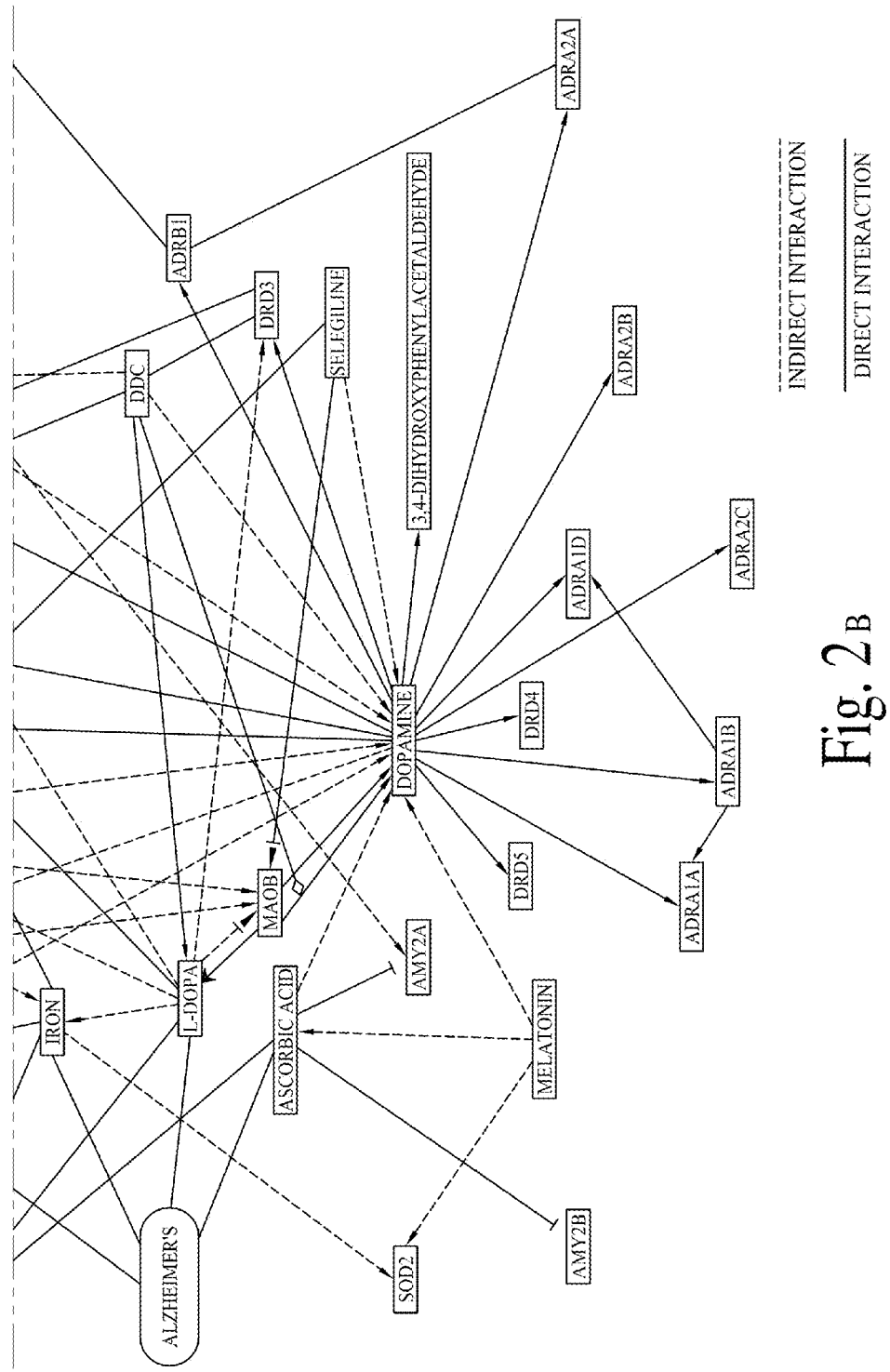
Figure 3B:
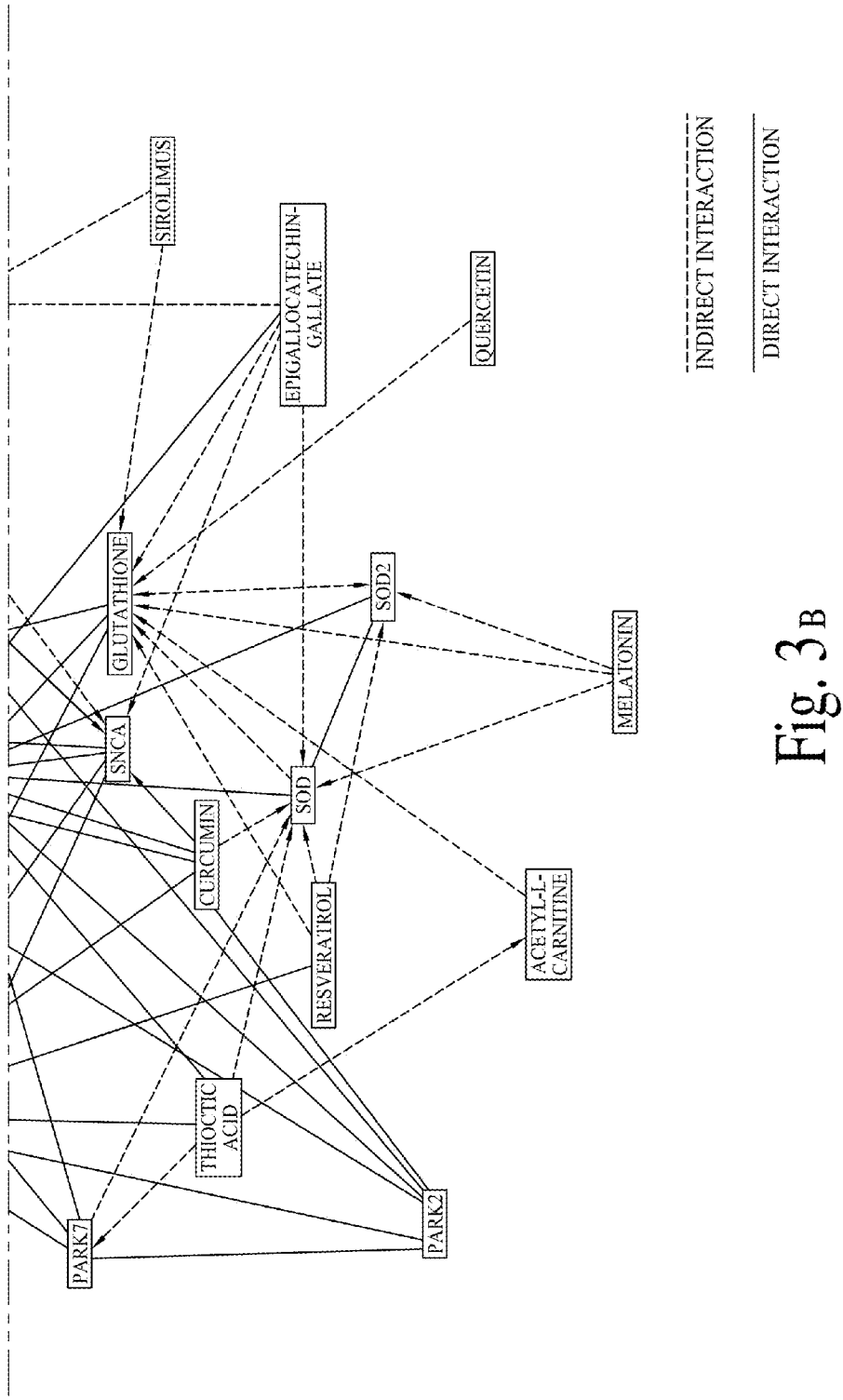

FIGS. 1A and 1B illustrate direct and indirect interactions of Alzheimer's disease related genes/proteins (e.g., APOE, APP, BACE1, CLU, MAPT/TAU, PSEN1, PSEN2, SORL1, TOMM40 and UBQLN1) with a set of bioactive compounds and/or bioactive molecules, utilizing a comprehensive biological pathway analysis (BPA) software.

FIGS. 2A, 2B, 3A and 3B illustrate direct and indirect interactions of Alzheimer's, Dementia and Parkinson's disease related genes/proteins (e.g., DOPAMINE, LRRK2, MAOB, PARK2 and SNCA) with a set of bioactive compounds and/or bioactive molecules, utilizing biological pathway analysis (BPA) software.

Figures 4, 4A:
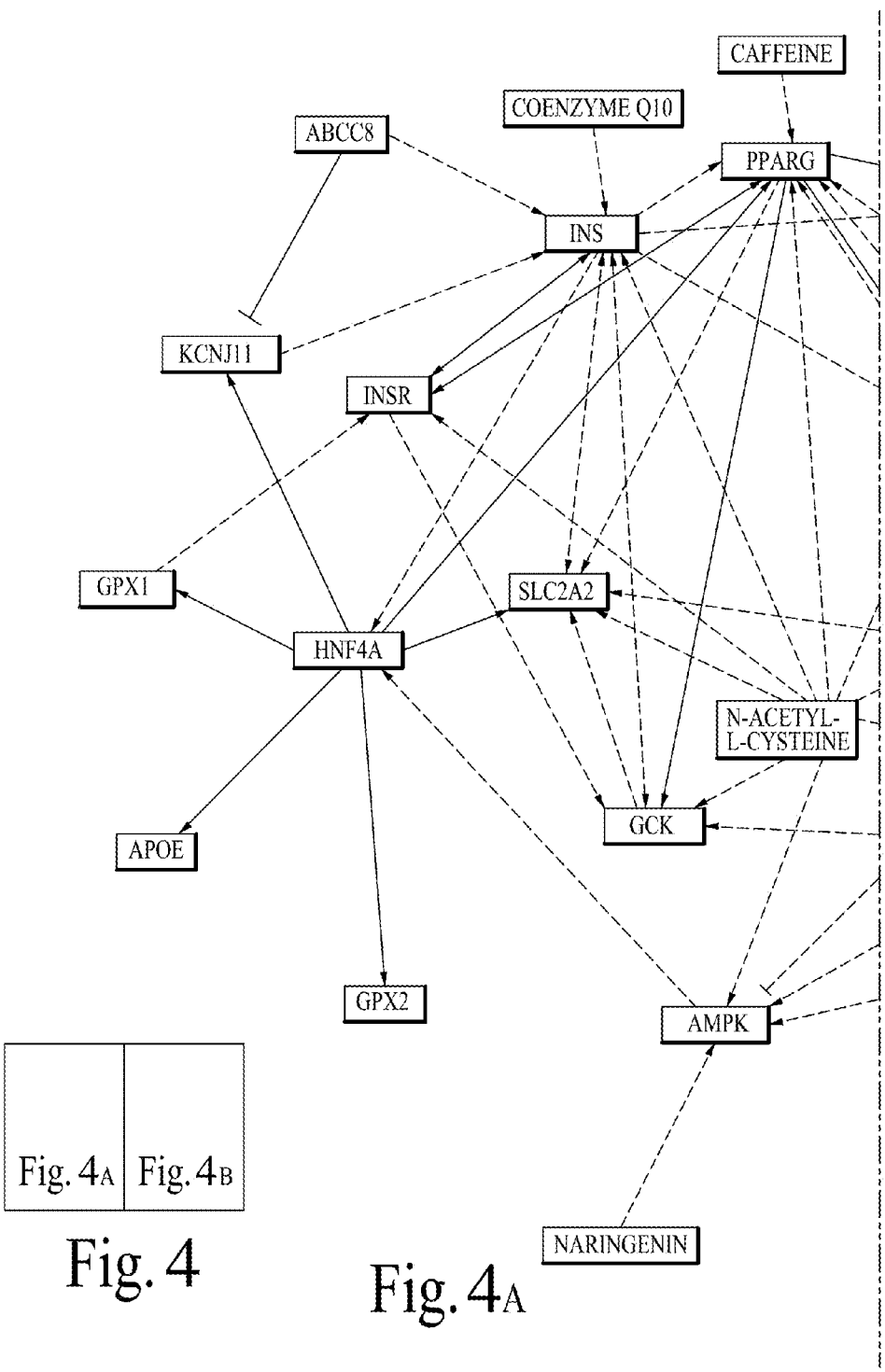
FIGS. 4A and 4B illustrate interactions of Type-2 Diabetes disease related genes/proteins with a set of bioactive compounds and/or bioactive molecules.
Figure 4B:
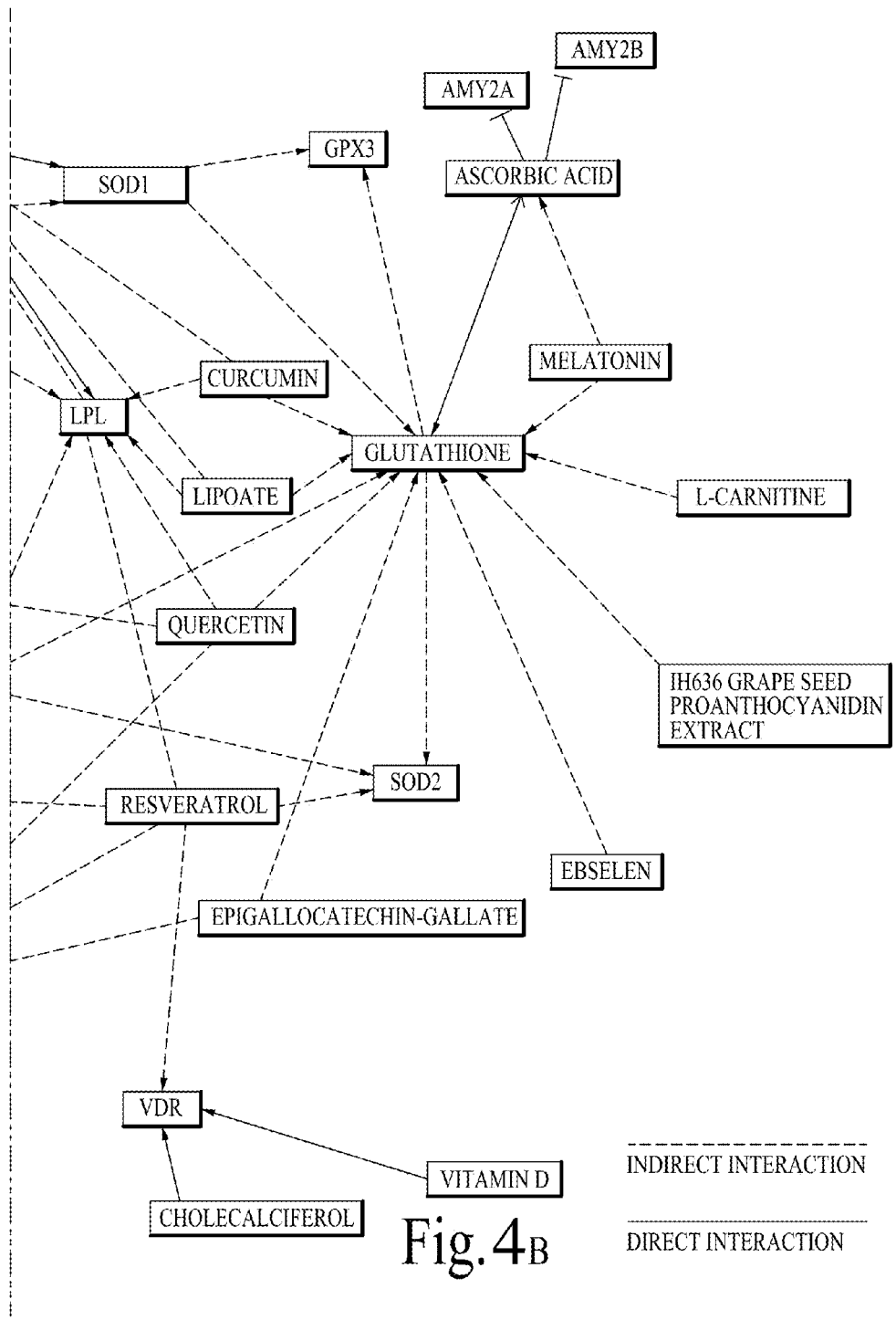

FIGS. 4A and 4B illustrate direct and indirect interactions of Type-2 Diabetes disease related genes/proteins (e.g., ABCC8, GCK, HNF4A, INS, INSR, KCNJ11, LPL, PPARG and SLC2A2) with a set of bioactive compounds and/or bioactive molecules, utilizing biological pathway analysis (BPA) software.

Furthermore, Alzheimer's disease related gene/protein APOE is linked with Type-2 Diabetes disease related gene/protein HNF4A.

FIGS. 1A, 1B, 2A, 2B, 3A and 3B are critical to design compositions for lowering the risks of Alzheimer's disease.

FIGS. 4A and 4B are critical to design compositions for lowering the risks of Diabetes disease.

Figure 5A:
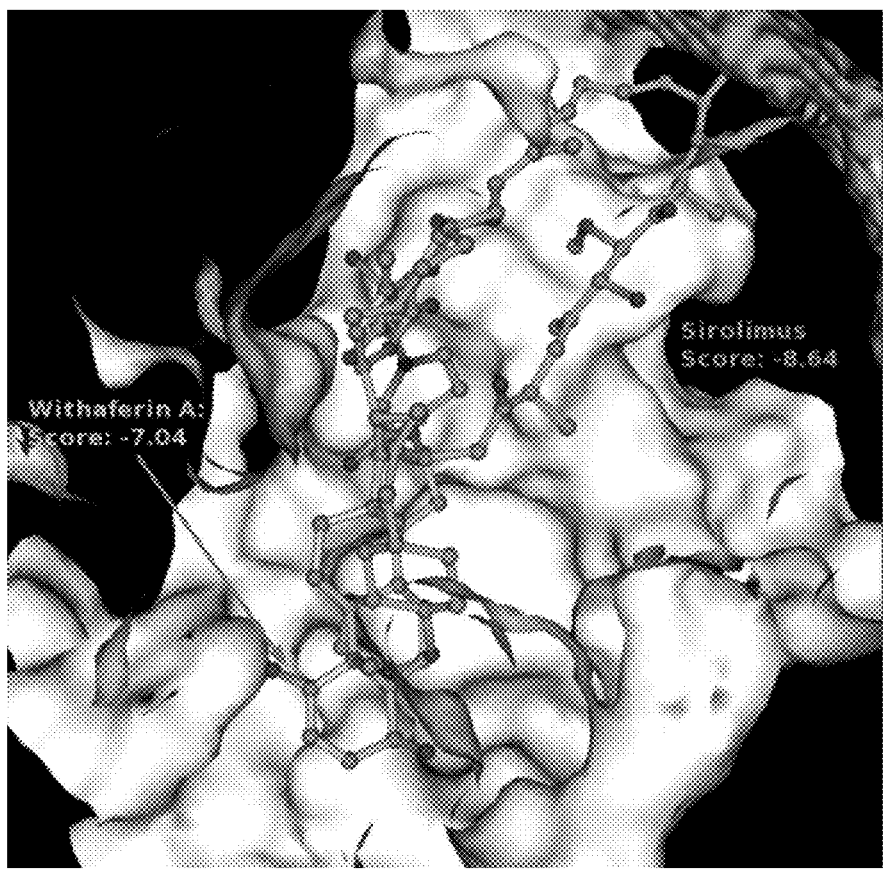
FIGS. 5A and 5B illustrate molecular docking score with mTOR.
Figure 5B:
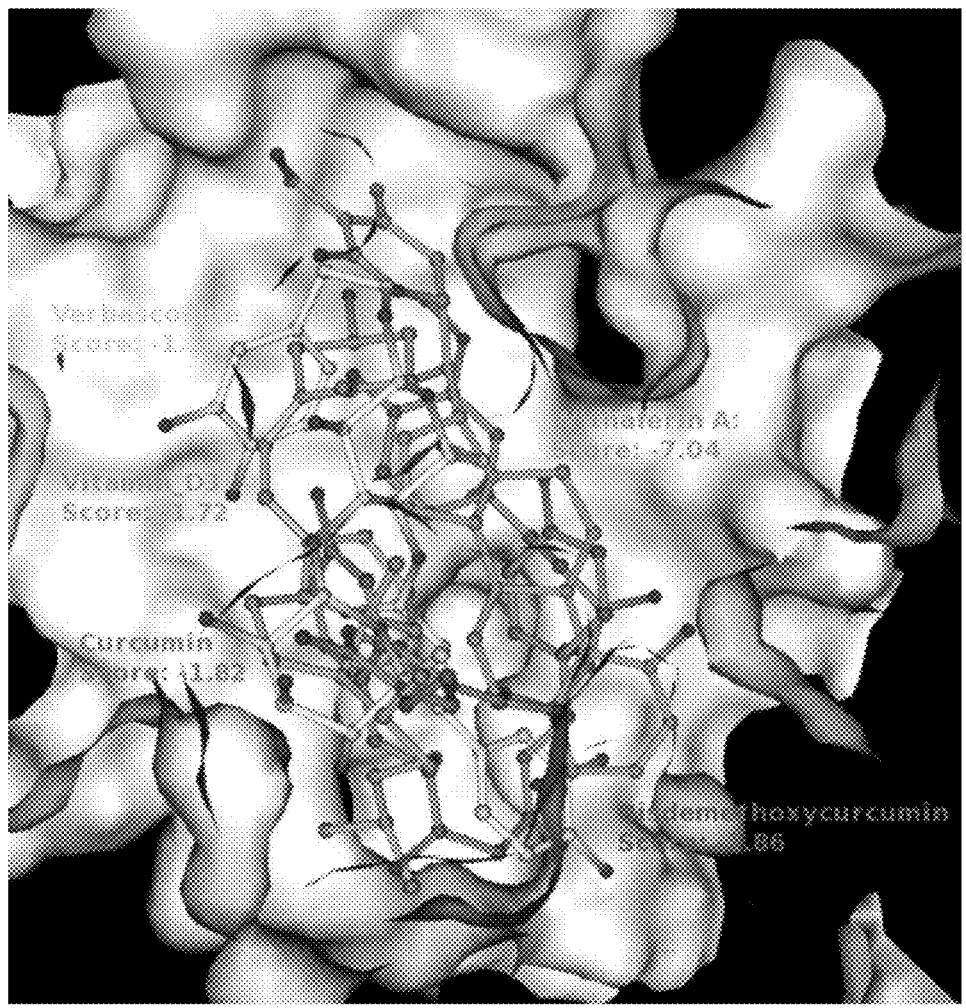

FIGS. 5A and 5B are critical to design compositions for suppressing/inhibiting mTOR.

Compositions

TABLE 1

Composition Of A Mixture Of Micronutrients - May Also Include Some Bioactive Compounds From Tables After This Table.

|  | Unit | +/−50% | WT % |
|---|---|---|---|
| Mineral | | | |
| Chromium Picolinate | Mg | 0.5 | 0.01% |
| Magnesium L-Threonate | Mg | 400 | 10.84% |
| Selenium (Selenomethionine) | Mg | 0.1 | 0.00% |
| Zinc (L-Opti) | Mg | 15 | 0.41% |
| Nucleotide | | | |
| Nucleotides (DNA) | Mg | 400 | 10.84% |
| Nucleotides (RNA) | Mg | 40 | 1.08% |
| Vitamin | | | |
| Vitamin $B_1$ (Thiamine) | Mg | 10 | 0.27% |
| Vitamin $B_3$ (Nicotinamide) | Mg | 400 | 10.84% |
| Vitamin $B_5$ | Mg | 200 | 5.42% |
| Vitamin $B_6$ (Pyritinol Or Pyridoxal 5'-Phosphate) | Mg | 20 | 0.54% |
| Vitamin $B_9$ (Folate) | Mg | 0.5 | 0.01% |
| Vitamin $B_{12}$ (Methylcobalamin) | Mg | 1 | 0.03% |
| Vitamin C | Mg | 200 | 5.42% |
| Vitamin $D_3$ (Cholecalciferol) | Mg | 0.25 | 0.01% |
| Vitamin $K_2$ | Mg | 2 | 0.05% |
| Other | | | |
| Lactoferrin | Mg | 2000 | 54.21% |
| Total Weight | G | 3.69 | 100.00% |

TABLE 2A

Composition Of A Mixture Of Antioxidants - May Also Include Some Bioactive Compounds From Tables Before & After This Table.

| Chemical | Unit | +/−50% | WT % |
|---|---|---|---|
| Acetyl-L-Carnitine | Mg | 200 | 3.69% |
| Alpha-R-Lipoic Acid | Mg | 20 | 0.37% |
| Coenzyme $Q_{10}$ (Nanoformulated)[1,2] | Mg | 200 | 3.69% |
| D-Ribose | Mg | 400 | 7.38% |
| Epigallocatechin Gallate | Mg | 200 | 3.69% |
| Ferulic Acid | Mg | 200 | 3.69% |
| Hyaluronic Acid | Mg | 200 | 3.69% |
| Inositol Hexanicotinate | Mg | 2000 | 36.90% |
| Isothiocyanate Sulforaphane | Mg | 200 | 3.69% |
| L-Analyl-L-Glutamine | Mg | 200 | 3.69% |
| L-Glutamine | Mg | 200 | 3.69% |
| L-Glutathione (Or Ebselen Or N-Acetyl-L-Cysteine) | Mg | 200 | 3.69% |
| Pterostilbene | Mg | 200 | 3.69% |
| Quercetin (Nanoformulated)[1,2] | Mg | 200 | 3.69% |
| Resveratrol (Nanoformulated)[1,2] | Mg | 200 | 3.69% |
| Superoxide Dismutase (SOD)* (Nanoformulated)[1,2] | Mg | 200 | 3.69% |
| Ubiquinol (Nanoformulated)[1,2] | Mg | 400 | 7.38% |
| Total Weight | G | 5.42 | 100.00% |

TABLE 2B

Additional Composition Of A Mixture Of Antioxidants - May Also Include Some Bioactive Compounds From Tables Before & After This Table.

| Botanical | Unit | +/−50% | WT % |
|---|---|---|---|
| Aronia melanocarpa[+] | Mg | 200 | 12.50% |
| Citrus limonum[+] | Mg | 200 | 12.50% |
| Daucus carota[+] | Mg | 200 | 12.50% |

TABLE 2B-continued

Additional Composition Of A Mixture Of Antioxidants - May Also Include Some Bioactive Compounds From Tables Before & After This Table.

| Botanical | Unit | +/−50% | WT % |
|---|---|---|---|
| *Hibiscus* spp.[+] | Mg | 200 | 12.50% |
| *Malus domestica*[+] | Mg | 200 | 12.50% |
| *Ribes nigrum*[+] | Mg | 200 | 12.50% |
| *Sambucus nigra*[+] | Mg | 200 | 12.50% |
| *Vaccinium* spp.[+] | Mg | 200 | 12.50% |
| Total Weight | G | 1.60 | 100.00% |

TABLE 3A

Composition Of A Multi-Serve Antioxidant Liquid - May Also Include Some Bioactive Compounds From Tables Before & After This Table.

| | Unit | +/−50% | WT % |
|---|---|---|---|
| Botanical | | | |
| *Actinidia chinenesis*[+] | G | 25 | 5.49% |
| *Ananas comosus*[+] | G | 25 | 5.49% |
| *Cocos nucifera*[+] | G | 350 | 76.88% |
| *Garcinia mangostana*[+] | G | 25 | 5.49% |
| *Litchi chinensis*[+] | G | 25 | 5.49% |
| *Vitis* spp.[+] | G | 0.75 | 0.16% |
| Chemical | | | |
| Citicoline (Or L-Alpha Glycerylphosphorylcholine) | G | 0.75 | 0.16% |
| Coenzyme $Q_{10}$ (Nanoformulated)[1,2] | G | 0.75 | 0.16% |
| D-Ribose | G | 0.75 | 0.16% |
| L-Analyl-L-Glutamine | G | 0.75 | 0.16% |
| L-Theanine | G | 0.75 | 0.16% |
| Ubiquinol (Nanoformulated)[1,2] | G | 0.75 | 0.16% |
| Total Weight | G | 455.25 | 100.00% |

TABLE 3B

Composition Of A Single-Serve Antioxidant Liquid - May Also Include Some Bioactive Compounds From Tables Before & After This Table.

| | Unit | +/−50% | WT % |
|---|---|---|---|
| Chemical | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.44% |
| D-Ribose | G | 0.25 | 0.05% |
| Gamma-Aminobutyric Acid | G | 0.25 | 0.05% |
| Inulin | G | 5 | 1.09% |
| L-Analyl-L-Glutamine | G | 0.25 | 0.05% |
| L-Theanine | G | 0.25 | 0.05% |
| Melatonin (Extended Release) | G | 0.002 | 0.00% |
| Omega 3-6-9 Acid (Including Decosahexanoic Acid) (Nanoformulated)[1] | G | 0.25 | 0.05% |
| Plant Sterol (Nanoformulated)[1] | G | 5 | 1.09% |
| Ubiquinol (Nanoformulated)[1,2] | G | 0.25 | 0.05% |
| Uridine | G | 0.25 | 0.05% |
| Sweetener | | | |
| Erythritol | G | 10 | 2.18% |
| *Stevia rebaudiana*[+] | G | 0.025 | 0.01% |
| Trehalose | G | 0.25 | 0.05% |

TABLE 3B-continued

Composition Of A Single-Serve Antioxidant Liquid - May Also Include Some Bioactive Compounds From Tables Before & After This Table.

| | Unit | +/−50% | WT % |
|---|---|---|---|
| Other | | | |
| Acidified Coconut Water (Or Filter Water) | G | 435 | 94.66% |
| Live *Lactobacillus plantarum* 299v | Billion | 10 | 0.00% |
| Total Weight | G | 459.52 | 100.00% |

TABLE 3C

Composition Of A Single-Serve Antioxidant Liquid - May Also Include Some Bioactive Compounds From Tables Before & After This Table.

| | Unit | +/−50% | WT % |
|---|---|---|---|
| Botanical | | | |
| *Aronia melanocarpa*[+] | G | 0.25 | 0.05% |
| *Citrus limonum*[+] | G | 0.25 | 0.05% |
| *Daucus carota*[+] | G | 0.25 | 0.05% |
| *Hibiscus* spp.[+] | G | 0.25 | 0.05% |
| *Malus domestica*[+] | G | 0.25 | 0.05% |
| *Ribes nigrum*[+] | G | 0.25 | 0.05% |
| *Sambucus nigra*[+] | G | 0.25 | 0.05% |
| *Vaccinium* spp.[+] | G | 0.25 | 0.05% |
| Chemical | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.43% |
| D-Ribose | G | 0.25 | 0.05% |
| Gamma-Aminobutyric Acid | G | 0.25 | 0.05% |
| Inulin | G | 5 | 1.08% |
| L-Analyl-L-Glutamine | G | 0.25 | 0.05% |
| L-Theanine | G | 0.25 | 0.05% |
| Melatonin (Extended Release) | G | 0.002 | 0.00% |
| Omega 3-6-9 Acid (Including Decosahexanoic Acid) (Nanoformulated)[1] | G | 0.25 | 0.05% |
| Plant Sterol (Nanoformulated)[1] | G | 5 | 1.08% |
| Ubiquinol (Nanoformulated)[1,2] | G | 0.25 | 0.05% |
| Uridine | G | 0.25 | 0.05% |
| Sweetener | | | |
| Erythritol | G | 10 | 2.17% |
| *Stevia rebaudiana*[+] | G | 0.025 | 0.01% |
| Trehalose | G | 0.25 | 0.05% |
| Other | | | |
| Acidified Coconut Water (Or Filter Water) | G | 435 | 94.25% |
| Live *Lactobacillus plantarum* 299v | Billion | 10 | 0.00% |
| Total Weight | G | 461.52 | 100.00% |

TABLE 3D

Composition Of Botanicals - May Also Include Some Bioactive Compounds From Tables Before & After This Table.

| Botanical | Unit | +/−50% | WT % |
|---|---|---|---|
| *Chamomilla recutita* | Mg | 200 | 16.66% |
| *Humulus lupulus* | Mg | 200 | 16.66% |
| *Lavandula angustifolia* | Mg | 200 | 16.66% |

TABLE 3D-continued

Composition Of Botanicals - May Also Include Some Bioactive Compounds From Tables Before & After This Table.

| Botanical | Unit | +/−50% | WT % |
|---|---|---|---|
| *Melissa officinalis* | Mg | 200 | 16.66% |
| *Passiflora incarnate* | Mg | 200 | 16.66% |
| *Valeriana officinalis* | Mg | 200 | 16.66% |
| Total Weight | G | 1.20 | 100.00% |

TABLE 3E

Composition Of A Mixture Of Electrolytes & Dextrose—May Also Include Some Bioactive Compounds From Tables Before & After This Table.

| Nutrient | Unit Per 8 Fluid Oz |
|---|---|
| Sodium | 10.6 mEq |
| Potassium | 4.7 mEq |
| Chloride | 8.3 mEq |
| Zinc | 1.9 Mg |
| Dextrose | 5.9 G |

Smart Container

Suitable biodegradable material (e.g., silk/plant derived plastic) can be used as a container.

A lens/an array of lenses (e.g., utilizing silk material) can be integrated on the interior wall of the container to detect a presence/growth of bacteria/microbes (e.g., bacteria/microbes in a liquid mixture).

1-D/2-D barcode/quick response (QR)-codes and/or a radio frequency identification device (RFID) active/passive tag and/or a near-field communication tag and/or an ultralower power consumption microprocessor (e.g., Ambiqmicro ARM Cortex-M3 microcontroller or an organic transistor based microprocessor) and/or a memory/storage component (e.g., a printed memristor on a flexible substrate) and a printed thin-film battery/miniature solar cell can be integrated on an exterior label (covers only a segment of the container's exterior) to (a) advertise (e.g., click to view more product (e.g., a drug) information linked with a website and/or click to receive a product coupon in near real-time/real-time), (b) interact (e.g., collective quorum vote on user liking/disliking of the product in near real-time/real-time) with a user's portable internet appliance and (c) communicate with an inventory management system and/or smart shopping cart, wherein the smart shopping cart is configured (with a removable (about seven (7) inch) display device integrated with a near-field communication tag and a near-field communication reader) to determine the user's commercial identity/personality (by interacting with the user's portable internet appliance) to a retailer on the doorway of the retailer.

Details of a portable internet appliance have been disclosed in U.S. Non-Provisional patent application Ser. No. 12/238,286 entitled, "PORTABLE INTERNET APPLIANCE", filed on Sep. 25, 2008.

However, it is possible to have the portable internet appliance handheld at one time and not be handheld in another time, as the display device of the portable internet appliance can be reconfigured/changed for at least two (2) different sizes, utilizing a removable/foldable/stretchable display device.

The removable/foldable/stretchable display device of the portable internet appliance can communicate with core electronics subsystem (the core electronics subsystem can include at least: a microprocessor component, a memory component, a storage component, a wireless/radio component (e.g., Bluetooth, millimeter wave, ultra-wideband (UWB) and Wi-Fi(N)) enabled compact removable/foldable/stretchable keyboard and an operating algorithm) of the portable internet appliance via a wireless/radio connection/an array of wireless/radio connections (e.g., Bluetooth, long term evolution (LTE), millimeter wave, near field communication, ultra-wideband (UWB), Wi-Fi(N) and WiMAX)

Alternatively, the microprocessor component and the wireless/radio connection component/the array of wireless/radio connection components (e.g., Bluetooth, long term evolution (LTE), millimeter wave, near field communication, ultra-wideband (UWB), Wi-Fi(N) and WiMAX) can be integrated as a first system-on-chip (SoC).

Furthermore, a second system-on-chip (SoC) can integrated two (2) subcomponents: a first sub component-digital microprocessor and a second subcomponent of a neural-network based analog microprocessor, wherein the neural network based analog microprocessor can be built by utilizing memristors/phase change memory elements.

Details of the second system-on-chip (SoC) have been disclosed in U.S. Non-Provisional patent application Ser. No. 13/448,378 entitled "SYSTEM AND METHOD FOR INTELLIGENT SOCIAL COMMERCE", filed on Apr. 15, 2012.

Furthermore, a third system-on-chip (or a system-in-package) can be fabricated/constructed by integrating the second system-on-chip (SoC) and the wireless/radio connection component/the array of wireless/radio connection components (e.g., Bluetooth, long term evolution (LTE), millimeter wave, near field communication, ultra-wideband (UWB), Wi-Fi(N) and WiMAX)

Alternatively, the above third system-on-chip (or a system-in-package) can be fabricated/constructed by integrating the second system-on-chip (SoC), a software defined/programmable wireless/radio connection component (wherein the software-defined/programmable wireless/radio connection component can switch/flip between Bluetooth, long term evolution (LTE), millimeter wave, near field communication, ultra-wideband (UWB), Wi-Fi(N) and WiMAX wireless/radio connections) and a tunable antenna.

The portable internet appliance can also communicate externally to a device and/or sensor via (e.g., Bluetooth, long term evolution (LTE), millimeter wave, near field communication, ultra-wideband (UWB), Wi-Fi(N) and WiMAX and sensor communication network).

Furthermore, Bluetooth, long term evolution (LTE), millimeter wave, near field communication, ultra-wideband (UWB), Wi-Fi(N) and WiMAX and sensor communication network can be provided from a dongle (e.g., a small USB device). The above dongle can be alternatively configured with a software-defined/programmable radio and/or many fixed antennas and/or a tunable antenna.

The user's commercial identity/personality can be enhanced by a collection of inputs from statistically similar users in near real time/real time. These inputs can complement/enhance the user's commercial identity/personality.

Furthermore, these inputs can be enhanced by statistical analysis, data mining analysis (e.g., ANN (artificial neural network), hierarchical cluster analysis and KNN (K-nearest neighbor analysis) and an integrated intelligent algorithm.

Furthermore, the integrated intelligent algorithm (can be located at a cloud server), can be enhanced by a first set of intelligent learning instructions-such as: artificial intelligence, data mining, fuzzy logic, machine vision, natural language processing, neural networks, pattern recognition, reasoning modeling (including hypothesis based reasoning modeling) and self-learning (including evidence based learning) and a second set of intelligent learning instructions-such as: algorithm-as-a-service, users' behavior modeling, physical search algorithm and software agent.

The exterior label can be integrated with thermochromic ink dot to indicate the temperature of the container.

The exterior label can be placed on a heat-dissipating thermally conducting flexible polymer film. Furthermore, the thermally conducting flexible polymer film can be integrated with a barrier thin-film (e.g., 100 nm thick atomic layer deposited $Al_2O_3$).

Humidity, oxygen and water can slowly diffuse into the container to degrade the liquid mixture over time. The barrier thin-film can prevent against humidity, oxygen and water.

The container can be suitably (about 15 degree centigrade hot-cold side temperature difference) heated or cooled by an array of (embedded superlattice based thin-film Peltier) thermoelectrics, wherein the thermoelectrics can be integrated (by utilizing Lithographie-Galvanoformung-Abformung (LIGA), electroforming and MEMS process) on the heat-dissipating thermally conducting flexible polymer film. The thermoelectrics covers only a section of the container's exterior.

Thermal resistance between the thermoelectrics and thermally conducting flexible polymer film is a critical parameter for an efficient heating and cooling.

The array of thermoelectrics can be electrically powered by an array of printed thin-film batteries/titanium dioxide solar cells (with porphyrin dyes).

TABLE 4

Composition Of A Mixture For Expression Of Beneficial NrF2 Protein—May Also Include Some Bioactive Compounds From Tables Before & After This Table.

| Botanical | Unit | +/−50% | WT % |
|---|---|---|---|
| Astragalus membranaceus[+] | Mg | 200 | 6.25% |
| Bacopa monnieri[+] | Mg | 200 | 6.25% |
| Camellia sinensis[+] (Black) | Mg | 200 | 6.25% |
| Camellia sinensis[+] (Green) | Mg | 200 | 6.25% |
| Curcuma longa[+] (Or A Curcuminoids Compound)[1,2,3,4] | Mg | 400 | 12.50% |
| Euterpe oleracea[+] | Mg | 200 | 6.25% |
| Hippophae rhamnoides[+] | Mg | 200 | 6.25% |
| Lycium barbarum[+] | Mg | 200 | 6.25% |
| Phyllanthus emblica[+] | Mg | 200 | 6.25% |
| Punica granatum[+] | Mg | 200 | 6.25% |
| Silybum marianum[+] | Mg | 200 | 6.25% |
| Tinospora cordifolia[+] | Mg | 200 | 6.25% |
| Vitis spp.[+] | Mg | 200 | 6.25% |
| Wasabia japonica[+] | Mg | 200 | 6.25% |
| Withania somnifera[+] | Mg | 200 | 6.25% |
| Total Weight | G | 3.20 | 100.00% |

Mitochondria are both generators of and targets for reactive molecular species. Therefore oxidative stress is intimately linked with mitochondrial dysfunction. The abundant mitochondria in a human brain is a major site of generation and action of reactive oxygen species (ROS)/reactive nitrogen species (RNS), since a human brain utilizes 20% of the inspired oxygen and 90% of the consumed oxygen to produce energy during oxidative phosphorylation. Thus a human brain is particularly sensitive to free radical damage/oxidative stress. Mitochondrial turnover is dependent on autophagy (meaning self-eating), which declines with age and is frequently dysfunctional in many neurodegenerative diseases (including Alzheimer's). Autophagy can engage in cross-talk with ROS/RNS in both cell signaling and protein damage. The mammalian Target of Rapamycin (mTOR) is an autophagy pathway. mTOR pathway can function as an inhibitor of the initiation process of autophagy.

Alzheimer's, Cardiovascular and Type-2 Diabetes diseases have misfolded and toxic damaged proteins triggered pathology at a molecular level. There are about 100,000 different proteins in a human body. After each protein is synthesized, it must be folded into a right shape to be functional. Mistakes can happen, that is why cells have sophisticated housekeeping mechanisms to repair or destroy poorly formed proteins before they can do any harm. Occasionally, a misfolded protein can evade these sophisticated housekeeping mechanisms and accumulates in sufficient quantities to clump together to damage/kill the cell.

One way to treat Alzheimer's, Cardiovascular and Type-2 Diabetes diseases, caused by misfolded proteins is to stimulate the housekeeping mechanisms by activating autophagy (or alternatively suppressing/inhibiting mTOR).

As a central controller of cell growth and nutrient sensor, mTOR plays a key role in ageing, Alzheimer's, Cardiovascular and Diabetes diseases.

Furthermore, AMPK up regulation (via bioactive compounds and/or bioactive molecules in *Momordica charantia*) activates autophagy via dual mechanisms involving not only by suppressing/inhibiting mTOR (in particular mTORC1), but also by direct phosphorylation of ULK1 protein.

The bioactive compounds 100 and/or bioactive molecules 100A to suppress/inhibit mTOR can be encapsulated/caged in the nanoshell 120.

The nanoshell 120 decorated with a targeting ligand, wherein the targeting ligand can recognize/match/bind with adenosine receptors—thus allowing the blood brain barrier to be opened for the passage of the nanoshell 120 to deliver the bioactive compounds 100 and/or bioactive molecules 100A to suppress/inhibit mTOR in a human brain.

TABLE 5

Molecular Docking Score With mTOR Utilizing Computational Chemistry Software (Also Illustrated in FIG. 5A and FIG. 5B).

| Chemical | Molecular Score |
|---|---|
| Rapamycin/Sirolimus (Known To Suppress/Inhibit mTOR) | −8.64 |
| Withaferin A | −7.04 |
| Cycloastragenol | −2.27 |
| Bisdemethoxycurcumin | −1.86 |
| Curcumin | −1.82 |
| Vitamin $D_3$ | −1.72 |
| Verbascoside | −1.13 |
| Momordin | −0.86 |
| SMER-28 | −0.71 |
| Resveratrol | −0.31 |
| Epigallocatechin gallate | −0.28 |
| Trehalose (Can Induce Autophagy Independent Of mTOR) | −0.25 |
| N,N-dimethylimidodicarbonimidic diamide (Metformin) | −0.11 |

TABLE 6A

Composition Of A Mixture For Suppressing/Inhibiting mTOR—May Also Include Some Bioactive Compounds From Tables Before & After This Table.

| | Unit | +/−50% | WT % |
|---|---|---|---|
| Botanical | | | |
| *Momordica charantia*+ | Mg | 200 | 20.00% |
| Chemical | | | |
| Withaferin A (Or A Chemical Derivative Or A Structural Analog Of Withaferin A) (Nanoformulated)[1,2] | Mg | 400 | 40.00% |
| Withanolides (Or A Chemical Derivative Or A Structural Analog Of Withanolides) (Nanoformulated)[1,2] | Mg | 200 | 20.00% |
| Withanosides (Or A Chemical Derivative Or A Structural Analog Of Withanosides) (Nanoformulated)[1,2] | Mg | 200 | 20.00% |
| Total Weight | G | 1.00 | 100.00% |

TABLE 6B

Composition Of A Mixture For Suppressing/Inhibiting mTOR—May Also Include Some Bioactive Compounds From Tables Before & After This Table.

| | Unit | +/−50% | WT % |
|---|---|---|---|
| Botanical | | | |
| *Momordica charantia*+ | Mg | 200 | 12.50% |
| Chemical | | | |
| Bisdemethoxycurcumin (Nanoformulated)[1,2] | Mg | 200 | 12.50% |
| Curcumin (Nanoformulated)[1,2,3,4] | Mg | 200 | 12.50% |
| Cycloastragenol (Nanoformulated)[1,2] | Mg | 200 | 12.50% |
| Withaferin A (Or A Chemical Derivative Or A Structural Analog Of Withaferin A)[1,2] | Mg | 400 | 25.00% |
| Withanolides (Or A Chemical Derivative Or A Structural Analog Of Withanolides) (Nanoformulated)[1,2] | Mg | 200 | 12.50% |
| Withanosides (Or A Chemical Derivative Or A Structural Analog Of Withanosides) (Nanoformulated)[1,2] | Mg | 200 | 12.50% |
| Vitamin | | | |
| Vitamin D$_3$ (Cholecalciferol) | Mg | 0.06 | 0.00% |
| Total Weight | G | 1.60 | 100.00% |

TABLE 6C

Composition Of A Mixture For Suppressing/Inhibiting mTOR—May Also Include Some Bioactive Compounds From Tables Before & After This Table.

| | Unit | +/−50% | WT % |
|---|---|---|---|
| Botanical | | | |
| *Momordica charantia*+ | Mg | 200 | 7.66% |
| Chemical | | | |
| 6-Bromo-N-2-propenyl-4-quinazolinamine (SMER-28) | Mg | 10 | 0.38% |
| Bisdemethoxycurcumin (Nanoformulated)[1,2] | Mg | 200 | 7.66% |
| Curcumin (Nanoformulated)[1,2,3,4] | Mg | 200 | 7.66% |
| Cycloastragenol (Nanoformulated)[1,2] | Mg | 200 | 7.66% |
| Epigallocatechin gallate | Mg | 200 | 7.66% |
| Momordin | Mg | 200 | 7.66% |
| Resveratrol (Nanoformulated)[1,2] | Mg | 200 | 7.66% |
| Trehalose | Mg | 200 | 7.66% |
| Verbascoside | Mg | 200 | 7.66% |
| Withaferin A (Or A Chemical Derivative Or A Structural Analog Of Withaferin A) (Nanoformulated)[1,2] | Mg | 400 | 15.33% |
| Withanolides (Or A Chemical Derivative Or A Structural Analog Of Withanolides) (Nanoformulated)[1,2] | Mg | 200 | 7.66% |
| Withanosides (Or A Chemical Derivative Or A Structural Analog Of Withanosides) (Nanoformulated)[1,2] | Mg | 200 | 7.66% |
| Vitamin | | | |
| Vitamin D$_3$ (Cholecalciferol) | Mg | 0.06 | 0.00% |
| Total Weight | G | 2.61 | 100.00% |

TABLE 6D

Composition Of A Mixture For Suppressing/Inhibiting mTOR—May Also Include Some Bioactive Compounds From Tables Before & After This Table.

| | Unit | +/−50% | WT % |
|---|---|---|---|
| Botanical | | | |
| *Cinnamomum zeylanicum*+ | Mg | 200 | 6.67% |
| *Momordica charantia*+ | Mg | 200 | 6.67% |
| *Vitis vinifera*+ (e.g., Seed Extract) | Mg | 200 | 6.67% |
| Chemical | | | |
| Bisdemethoxycurcumin (Nanoformulated)[1,2] | Mg | 200 | 6.67% |
| Curcumin (Nanoformulated)[1,2,3,4] | Mg | 200 | 6.67% |
| Cycloastragenol (Nanoformulated)[1,2] | Mg | 200 | 6.67% |
| Epigallocatechin gallate | Mg | 200 | 6.67% |
| Momordin | Mg | 200 | 6.67% |
| N,N-dimethylimidodicarbonimidic diamide (Or Chemical Derivative Or Structural Analog Of N,N-dimethylimidodicarbonimidic diamide) | Mg | 200 | 6.67% |
| Proanthocyanidins | Mg | 200 | 6.67% |
| Resveratrol (Nanoformulated)[1,2] | Mg | 200 | 6.67% |
| Withaferin A (Or A Chemical Derivative Or A Structural Analog Of Withaferin A) (Nanoformulated)[1,2] | Mg | 400 | 13.33% |
| Withanolides (Or A Chemical Derivative Or A Structural Analog Of Withanolides) (Nanoformulated)[1,2] | Mg | 200 | 6.67% |
| Withanosides (Or A Chemical Derivative Or A Structural Analog Of Withanosides) (Nanoformulated)[1,2] | Mg | 200 | 6.67% |
| Vitamin | | | |
| Vitamin D$_3$ (Cholecalciferol) | Mg | 0.06 | 0.00% |
| Total Weight | G | 3.00 | 100.00% |

TABLE 7A

Composition Of A Mixture For Lowering The Risks Of Alzheimer's Disease—May Also Include Some Bioactive Compounds From Tables Before & After This Table.

| | Unit | +/−50% | WT % |
|---|---|---|---|
| Botanical | | | |
| Bacopa monnieri[+] | Mg | 200 | 2.01% |
| Boswellia serrata[+,1] | Mg | 200 | 2.01% |
| Camellia sinensis[+] (Black) | Mg | 200 | 2.01% |
| Camellia sinensis[+] (Green) | Mg | 200 | 2.01% |
| Cinnamomum zeylanicum[+] | Mg | 200 | 2.01% |
| Curcuma longa[+] (Or A Curcuminoids Compound)[1,2,3,4] | Mg | 400 | 4.01% |
| Emblica officinalis[+] | Mg | 200 | 2.01% |
| Mucuna pruriens[+] | Mg | 200 | 2.01% |
| Paeoniae alba[+] | Mg | 200 | 2.05% |
| Panax quinquefolius[+] | Mg | 200 | 2.01% |
| Polygala tenuifolia[+] | Mg | 200 | 2.01% |
| Rosmarinus officinalis[+] | Mg | 200 | 2.01% |
| Silybum marianum[+] | Mg | 200 | 2.01% |
| Vitis vinifera[+] | Mg | 200 | 2.01% |
| Withania somnifera[+] | Mg | 200 | 2.01% |
| Chemical | | | |
| Acetylcholine (Or Choline Or Phosphatidyl Choline) | Mg | 200 | 2.01% |
| Alpha-R-Lipoic Acid | Mg | 20 | 0.20% |
| Aniracetam (Or Piracetam) | Mg | 200 | 2.01% |
| Caffeine | Mg | 20 | 0.20% |
| Citicoline (Or L-Alpha Glycerylphosphorylcholine) | Mg | 200 | 2.01% |
| Coenzyme Q$_{10}$ (Nanoformulated)[1,2] | Mg | 200 | 2.01% |
| DMAE (Dimethyl Amino Ethanol) | Mg | 200 | 2.01% |
| Epigallocatechin gallate | Mg | 200 | 2.01% |
| Fisetin | Mg | 200 | 2.01% |
| Huperzine A | Mg | 200 | 2.01% |
| L-Arginine | Mg | 200 | 2.01% |
| L-Carnosine | Mg | 200 | 2.01% |
| L-Dopa | Mg | 100 | 1.00% |
| L-Glutathione (Or Ebselen Or N-Acetyl-L-Cysteine) | Mg | 200 | 2.01% |
| L-Theanine | Mg | 200 | 2.01% |
| L-Tyrosine (Or M-Tyrosine Or N-Acetyl Tyrosine) | Mg | 200 | 2.01% |
| Melatonin | Mg | 1 | 0.01% |
| N-Acetyl-L-Carnitine | Mg | 400 | 4.01% |
| Omega 3-6-9 Acid (Including Decosahexanoic Acid) (Nanoformulated)[1] | Mg | 200 | 2.01% |
| Picamilon | Mg | 200 | 2.01% |
| Phosphatidylserine | Mg | 200 | 2.01% |
| Pyrroloquinoline Quinone (PQQ)[1,2] | Mg | 20 | 0.20% |
| Quercetin[1,2] | Mg | 200 | 2.01% |
| Resveratrol[1,2] | Mg | 200 | 2.01% |
| Tetramethylpyrazine (TMP) | Mg | 200 | 2.01% |
| Trehalose | Mg | 200 | 2.01% |
| Ubiquinol (Nanoformulated)[1,2] | Mg | 1000 | 10.04% |
| Uridine | Mg | 200 | 2.01% |
| Vinpocetine | Mg | 200 | 2.01% |
| Withaferin A (Or Chemical Derivative Or Structural Analog Of Withaferin A) (Nanoformulated)[1,2] | Mg | 400 | 4.01% |
| Mineral | | | |
| Magnesium L-Threonate | Mg | 400 | 4.01% |
| Vitamin | | | |
| Vitamin B$_{12}$ (Methylcobalamin) | Mg | 1 | 0.01% |
| Vitamin D$_3$ | Mg | 0.25 | 0.00% |
| Vitamin K$_2$ | Mg | 2.0 | 0.02% |
| Total Weight | G | 9.96 | 100.00% |

TABLE 7B

Additional Composition Of A Mixture For Lowering The Risks Of Alzheimer's Disease—May Also Include Some Bioactive Compounds From Tables Before & After This Table.

| | Unit | +/−50% | WT % |
|---|---|---|---|
| Botanical | | | |
| Bacopa monnieri[+] | Mg | 200 | 2.16% |
| Boswellia serrata[+,1] | Mg | 200 | 2.16% |
| Chamomilla recutita[+] | Mg | 200 | 2.16% |
| Cinnamomum zeylanicum[+] | Mg | 200 | 2.16% |
| Curcuma longa[+] (Or A Curcuminoids Compound)[1,2,3,4] | Mg | 400 | 4.33% |
| Humulus lupulus[+] | Mg | 200 | 2.16% |
| Melissa officinalis[+] | Mg | 200 | 2.16% |
| Passiflora incarnate[+] | Mg | 200 | 2.16% |
| Silybum marianum[+] | Mg | 200 | 2.16% |
| Valeriana officinalis[+] | Mg | 200 | 2.16% |
| Withania somnifera[+] | Mg | 200 | 2.16% |
| Chemical | | | |
| Acetylcholine (Or Choline Or Phosphatidyl Choline) | Mg | 200 | 2.16% |
| Caffeine | Mg | 20 | 0.22% |
| Citicoline (Or L-Alpha Glycerylphosphorylcholine) | Mg | 200 | 2.16% |
| Coenzyme Q$_{10}$ (Nanoformulated)[1,2] | Mg | 200 | 2.16% |
| L-Glutathione (Or Ebselen Or N-Acetyl-L-Cysteine) | Mg | 200 | 2.16% |
| L-Theanine | Mg | 200 | 2.16% |
| L-Tyrosine (Or M-Tyrosine Or N-Acetyl Tyrosine) | Mg | 200 | 2.16% |
| Melatonin | Mg | 2.5 | 0.03% |
| N-Acetyl-L-Carnitine | Mg | 400 | 4.33% |
| Omega 3-6-9 Acid (Including Decosahexanoic Acid) (Nanoformulated)[1] | Mg | 200 | 2.16% |
| Phosphatidylserine | Mg | 200 | 2.16% |
| Pyrroloquinoline Quinone (PQQ)[1,2] | Mg | 20 | 0.22% |
| Quercetin[1,2] | Mg | 200 | 2.16% |
| Resveratrol[1,2] | Mg | 200 | 2.16% |
| Tetramethylpyrazine (TMP) | Mg | 200 | 2.16% |
| Trehalose | Mg | 200 | 2.16% |
| Ubiquinol (Nanoformulated)[1,2] | Mg | 1000 | 10.82% |
| Uridine | Mg | 200 | 2.16% |
| Withaferin A (Or Chemical Derivative Or Structural Analog Of Withaferin A) (Nanoformulated)[1,2] | Mg | 400 | 4.33% |
| Mineral | | | |
| Magnesium L-Threonate | Mg | 400 | 4.33% |
| Vitamin | | | |
| Vitamin B$_{12}$ (Methylcobalamin) | Mg | 1 | 0.01% |
| Vitamin D$_3$ | Mg | 0.25 | 0.00% |
| Vitamin K$_2$ | Mg | 2.0 | 0.02% |
| Other | | | |
| Lactoferrin | Mg | 2000 | 21.63% |
| Total Weight | G | 9.25 | 100.00% |

Boswellia serrata can suppress/inhibit 5-lipoxygenase. A bioactive compound (e.g., 3-O-acetyl-11-keto-β-boswellic acid) of Boswellia serrata's can be nanoformulated to improve its bioavailability.

TABLE 7C

Additional Composition Of A Mixture For Lowering The Risks Of Alzheimer's Disease—May Also Include Some Bioactive Compounds From Tables Before & After This Table.

| | Unit | +/−50% | WT % |
|---|---|---|---|
| Botanical | | | |
| Tinospora cordifolia[+] | Mg | 200 | 5.20% |
| Withania somnifera[+] | Mg | 200 | 5.20% |

TABLE 7C-continued

Additional Composition Of A Mixture For Lowering The Risks Of Alzheimer's Disease—May Also Include Some Bioactive Compounds From Tables Before & After This Table.

| | Unit | +/−50% | WT % |
|---|---|---|---|
| Chemical | | | |
| Caffeine | Mg | 20 | 0.52% |
| Citicoline (Or L-Alpha Glycerylphosphorylcholine) | Mg | 400 | 10.41% |
| Curcumin | Mg | 200 | 5.20% |
| Decosahexanoic Acid | Mg | 400 | 10.41% |
| L-Glutathione (Or Ebselen Or N-Acetyl-L-Cysteine) | Mg | 200 | 5.20% |
| L-Theanine | Mg | 200 | 5.20% |
| Melatonin | Mg | 1 | 0.03% |
| Pyrroloquinoline Quinone (PQQ)[1,2] | Mg | 20 | 0.52% |
| Quercetin[1,2] | Mg | 200 | 5.20% |
| Ubiquinol | Mg | 1000 | 26.02% |
| Withaferin A (Or Chemical Derivative Or Structural Analog Of Withaferin A) (Nanoformulated)[1,2] | Mg | 400 | 10.41% |
| Mineral | | | |
| Magnesium L-Threonate | Mg | 400 | 10.41% |
| Vitamin | | | |
| Vitamin $D_3$ | Mg | 0.25 | 0.01% |
| Vitamin $K_2$ | Mg | 2.0 | 0.05% |
| Total Weight | G | 3.84 | 100.00% |

L-Theanine & melatonin combination for the night time dose, while L-Theanine and caffeine (or just caffeine) for the day time dose.

TABLE 7D

Additional Composition Of A Mixture For Lowering The Risks Of Alzheimer's Disease—May Also Include Some Bioactive Compounds From Tables Before & After This Table.

| Chemical | Unit | +/−50% | WT % |
|---|---|---|---|
| 4,5-Bis-(4-methoxyanilino)phthalimide | Mg | 20 | 6.78% |
| 6-Bromoindirubin-3'-oxime[2] | Mg | 10 | 3.39% |
| 6-Bromo-N-2-propenyl-4-quinazolinamine (SMER-28) | Mg | 10 | 3.39% |
| 3,6-Dibromo-α-[(phenylamino)methyl]-9H-carbazole-9-ethanol | Mg | 20 | 6.78% |
| Lithium (Lithium Orotate Or Lithium Chloride) | Mg | 5 | 1.69% |
| Sodium Phenylbutyrate[2] | Mg | 10 | 3.39% |
| Uric Acid (From Inosine: Hypoxanthine Ribose) | Mg | 20 | 6.78% |
| (+/−)-1-(1-Benzo[b]thien-2-ylethyl)-1-hydroxyurea | Mg | 200 | 67.80% |
| Total Weight | G | 0.29 | 100.00% |

TABLE 8

Composition Of A Mixture For Lowering The Risks Of Cardiovascular Disease—May Also Include Some Bioactive Compounds From Tables Before & After This Table.

| | Unit | +/−50% | WT % |
|---|---|---|---|
| Botanical | | | |
| Allium sativum[+] | Mg | 200 | 1.55% |
| Crataegus oxyacantha[+] | Mg | 200 | 1.55% |
| Inula racemosa[+] | Mg | 200 | 1.55% |
| Olea europaea[+] | Mg | 200 | 1.55% |
| Rauwolfia serpentina[+] | Mg | 200 | 1.55% |
| Terminalia arjuna[+] | Mg | 200 | 1.55% |
| Capsaicin (Or Capsinoid) | Mg | 200 | 1.55% |
| Chromium Polynicotinate | Mg | 0.2 | 0.00% |
| Cocoa Flavanols | Mg | 400 | 3.10% |
| Coenzyme $Q_{10}$ (Nanoformulated)[1,2] | Mg | 1000 | 7.75% |
| L-Glutathione (Or Ebselen Or N-Acetyl-L-Cysteine) | Mg | 200 | 1.55% |
| Plant Sterols (Nanoformulated)[1] | Mg | 5000 | 38.76% |
| Red Yeast Rice Extract | Mg | 2500 | 19.38% |
| Ubiquinol (Nanoformulated)[1,2] | Mg | 1000 | 7.75% |
| Mineral | | | |
| Magnesium | Mg | 400 | 3.10% |
| Other | | | |
| Coconut Oil | Mg | 1000 | 7.75% |
| Total Weight | G | 12.90 | 100.00% |

TABLE 9A

Composition Of A Mixture For Lowering The Risks Of Type-2 Diabetes Disease—May Also Include Some Bioactive Compounds From Tables Before After This Table.

| | Unit | +/−50% | WT % |
|---|---|---|---|
| Botanical | | | |
| Andrographis paniculata[+] | Mg | 200 | 4.00% |
| Artemisia princeps[+] | Mg | 200 | 4.00% |
| Camellia sinensis[+] (Black) | Mg | 200 | 4.00% |
| Camellia sinensis[+] (Green) | Mg | 200 | 4.00% |
| Caralluma fimbriata[+] | Mg | 200 | 4.00% |
| Cinnamomum zeylanicum[+] | Mg | 200 | 4.00% |
| Coccinia indica[+] | Mg | 800 | 16.00% |
| Irvingia gabonensis[+] | Mg | 200 | 4.00% |
| Litchi chinensis[+] | Mg | 200 | 4.00% |
| Momordica charantia[+] | Mg | 200 | 4.00% |
| Salacia oblonga[+] | Mg | 800 | 16.00% |
| Chemical | | | |
| Beta Glucan | Mg | 200 | 4.00% |
| Chromium Polynicotinate | Mg | 0.2 | 0.0% |
| Chlorogenic Acid | Mg | 200 | 4.00% |
| Nobiletin (Or 2000 Mg Naringenin) | Mg | 200 | 4.00% |
| Touchi | Mg | 1000 | 20.00% |
| Total Weight | G | 5.00 | 100.00% |

Chlorogenic acid (CHA) is an activator of calcineurin.

TABLE 9B

Composition Of A Mixture For Lowering The Risks Of Type-2 Diabetes Disease—May Also Include Some Bioactive Compounds From Tables Before & After This Table.

| | Unit | +/−50% | WT % |
|---|---|---|---|
| Botanical | | | |
| Banaba | Mg | 200 | 6.25% |
| Coccinia cordifolia[+] | Mg | 200 | 6.25% |
| Emblica officinalis[+] | Mg | 200 | 6.25% |
| Green Coffee Bean Extract | Mg | 1200 | 37.50% |
| Lagerstroemia speciosa[+] (Jarul) | Mg | 200 | 6.25% |
| Punica granatum | Mg | 200 | 6.25% |
| Syzygium cumini[+] | Mg | 200 | 6.25% |

TABLE 9B-continued

Composition Of A Mixture For Lowering The Risks Of Type-2 Diabetes Disease—May Also Include Some Bioactive Compounds From Tables Before & After This Table.

| | Unit | +/−50% | WT % |
|---|---|---|---|
| Chemical | | | |
| 4-(4-Hydroxyphenyl)butan-2-one (Nanoformulated)[1,2] | Mg | 400 | 12.50% |
| Cyanidin 3-glucoside (Nanoformulated)[1,2] | Mg | 400 | 12.50% |
| Total Weight | G | 3.20 | 100.00% |

4-(4-Hydroxyphenyl)butan-2-one is raspberry ketone. Green coffee bean extract has chlorogenic acid (CHA).

Explanation Of Notations {+, *, 1, 2, 3 and 4}

| | |
|---|---|
| + | A component (meaning an extract or a powder or a bioactive compound or a bioactive molecule from any part of the specific plant) |
| * | Found in *Citrullus vulgaris*[+] |
| 1 | Nanoformulated means nanoemulsion/nanodispersion/nanosuspension or nanoencapsulation |
| 2 | Chemically coupled with Triphenylphosphonium (TPP) or a chemical derivative of Triphenylphosphonium (TPP) or a structural analog of Triphenylphosphonium (TPP) |
| 3 | Higher bioavailability with black pepper (*Piper nigrum*) and/or vitamin $D_3$ |
| 4 | FLLL-11 or FLLL-12 or GO-Y030 or GO-Y031 can replace curcumin |

TABLE 10

Composition Of A Mixture Of Sugar Free Sweetener

| | Unit | +/−50% | WT % |
|---|---|---|---|
| Botanical | | | |
| *Stevia rebaudiana*[+] | Mg | 20 | 0.42% |
| Chemical | | | |
| Erythritol | Mg | 4500 | 95.34% |
| Trehalose | Mg | 200 | 4.24% |
| Total Weight | G | 4.72 | 100.00% |

TABLE 11A

Composition Of A Mixture Of Sugar Free Super-Sweetener

| | Unit | +/−50% | WT % |
|---|---|---|---|
| Botanical | | | |
| *Capparis masaikai*[+] (Mabinlins Protein) | Mg | 5 | 0.11% |
| *Stevia rebaudiana*[+] | Mg | 20 | 0.42% |
| Chemical | | | |
| Erythritol | Mg | 4500 | 95.24% |
| Trehalose | Mg | 200 | 4.23% |
| Total Weight | G | 4.72 | 100.00% |

TABLE 11B

Composition Of A Mixture Of Sugar Free Super-Sweetener

| | Unit | +/−50% | WT % |
|---|---|---|---|
| Botanical | | | |
| *Curculigo latifolia*[+] (Curculin Protein) | Mg | 5 | 0.11% |
| *Stevia rebaudiana*[+] | Mg | 20 | 0.42% |
| Chemical | | | |
| Erythritol | Mg | 4500 | 95.24% |
| Trehalose | Mg | 200 | 4.23% |
| Total Weight | G | 4.72 | 100.00% |

TABLE 11C

Composition Of A Mixture Of Sugar Free Super-Sweetener

| | Unit | +/−50% | WT % |
|---|---|---|---|
| Botanical | | | |
| *Dioscoreophyllum cumminsii*[+] (Monellin Protein) | Mg | 2 | 0.04% |
| *Stevia rebaudiana*[+] | Mg | 20 | 0.42% |
| Chemical | | | |
| Erythritol | Mg | 4500 | 95.30% |
| Trehalose | Mg | 200 | 4.24% |
| Total Weight | G | 4.72 | 100.00% |

TABLE 11D

Composition Of A Mixture Of Sugar Free Super-Sweetener

| | Unit | +/−50% | WT % |
|---|---|---|---|
| Botanical | | | |
| *Momordica grosvenorii*/*Siraitia grosvenorii*[+] | Mg | 5 | 0.11% |
| *Stevia rebaudiana*[+] | Mg | 20 | 0.42% |
| Chemical | | | |
| Erythritol | Mg | 4500 | 95.24% |
| Trehalose | Mg | 200 | 4.23% |
| Total Weight | G | 4.72 | 100.00% |

TABLE 11E

Composition Of A Mixture Of Sugar Free Super-Sweetener

| | Unit | +/−50% | WT % |
|---|---|---|---|
| Botanical | | | |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| Chemical | | | |
| Erythritol | Mg | 4500 | 95.14% |
| Trehalose | Mg | 200 | 4.23% |
| Total Weight | G | 4.73 | 100.00% |

TABLE 11F

Composition Of A Mixture Of Sugar Free Super-Sweetener

| | Unit | +/−50% | WT % |
|---|---|---|---|
| Botanical | | | |
| Stevia rebaudiana+ | Mg | 20 | 0.42% |
| Synsepalum dulcificum+ (Miraculin Protein) | Mg | 5 | 0.11% |
| Chemical | | | |
| Erythritol | Mg | 4500 | 95.24% |
| Trehalose | Mg | 200 | 4.23% |
| Total Weight | G | 4.72 | 100.00% |

TABLE 11G

Composition Of A Mixture Of Sugar Free Super-Sweetener

| | Unit | +/−50% | WT % |
|---|---|---|---|
| Botanical | | | |
| Stevia rebaudiana+ | Mg | 20 | 0.42% |
| Thaumatococcus daniellii+ (Thaumatin Protein) | Mg | 1 | 0.02% |
| Chemical | | | |
| Erythritol | Mg | 4500 | 95.32% |
| Trehalose | Mg | 200 | 4.24% |
| Total Weight | G | 4.72 | 100.00% |

TABLE 11H

Composition Of A Mixture Of Sugar Free Super-Sweetener

| | Unit | +/−50% | WT % |
|---|---|---|---|
| Botanical | | | |
| Dioscoreophyllum cumminsii+ (Monellin Protein) | Mg | 2 | 0.04% |
| Pentadiplandra brazzeana+ (Brazzein Protein) | Mg | 5 | 0.11% |
| Pentadiplandra brazzeana+ (Pentadin Protein) | Mg | 5 | 0.11% |
| Stevia rebaudiana+ | Mg | 20 | 0.42% |
| Chemical | | | |
| Erythritol | Mg | 4500 | 95.10% |
| Trehalose | Mg | 200 | 4.23% |
| Total Weight | G | 4.73 | 100.00% |

TABLE-11I

Composition Of A Mixture Of Sugar Free Super-Sweetener

| | Unit | +/−50% | WT % |
|---|---|---|---|
| Botanical | | | |
| Dioscoreophyllum cumminsii+ (Monellin Protein) | Mg | 2 | 0.04% |
| Pentadiplandra brazzeana+ (Brazzein Protein) | Mg | 5 | 0.11% |
| Pentadiplandra brazzeana+ (Pentadin Protein) | Mg | 5 | 0.11% |
| Stevia rebaudiana+ | Mg | 20 | 0.42% |
| Synsepalum dulcificum+ (Miraculin Protein) | Mg | 5 | 0.11% |
| Chemical | | | |
| Erythritol | Mg | 4500 | 95.00% |
| Trehalose | Mg | 200 | 4.22% |
| Total Weight | G | 4.73 | 100.00% |

TABLE 11J

Composition Of A Mixture Of Sugar Free Super-Sweetener

| | Unit | +/−50% | WT % |
|---|---|---|---|
| Botanical | | | |
| Capparis masaikai+ (Mabinlins Protein) | Mg | 5 | 0.11% |
| Dioscoreophyllum cumminsii+ (Monellin Protein) | Mg | 2 | 0.04% |
| Pentadiplandra brazzeana+ (Brazzein Protein) | Mg | 5 | 0.11% |
| Pentadiplandra brazzeana+ (Pentadin Protein) | Mg | 5 | 0.11% |
| Stevia rebaudiana+ | Mg | 20 | 0.42% |
| Synsepalum dulcificum+ (Miraculin Protein) | Mg | 5 | 0.11% |
| Chemical | | | |
| Erythritol | Mg | 4500 | 94.90% |
| Trehalose | Mg | 200 | 4.22% |
| Total Weight | G | 4.74 | 100.00% |

TABLE 11K

Composition Of A Mixture Of Sugar Free Super-Sweetener

| | Unit | +/−50% | WT % |
|---|---|---|---|
| Botanical | | | |
| Curculigo latifolia+ (Curculin Protein) | Mg | 5 | 0.11% |
| Dioscoreophyllum cumminsii+ (Monellin Protein) | Mg | 2 | 0.04% |
| Pentadiplandra brazzeana+ (Brazzein Protein) | Mg | 5 | 0.11% |
| Pentadiplandra brazzeana+ (Pentadin Protein) | Mg | 5 | 0.11% |
| Stevia rebaudiana+ | Mg | 20 | 0.42% |
| Synsepalum dulcificum+ (Miraculin Protein) | Mg | 5 | 0.11% |
| Chemical | | | |
| Erythritol | Mg | 4500 | 94.90% |
| Trehalose | Mg | 200 | 4.22% |
| Total Weight | G | 4.74 | 100.00% |

TABLE 11L

Composition Of A Mixture Of Sugar Free Super-Sweetener

| | Unit | +/−50% | WT % |
|---|---|---|---|
| Botanical | | | |
| Capparis masaikai+ (Mabinlins Protein) | Mg | 1 | 0.02% |

TABLE 11L-continued

Composition Of A Mixture Of Sugar Free Super-Sweetener

|  | Unit | +/−50% | WT % |
|---|---|---|---|
| *Curculigo latifolia*+ (Curculin Protein) | Mg | 1 | 0.02% |
| *Dioscoreophyllum cumminsii*+ (Monellin Protein) | Mg | 2 | 0.04% |
| *Pentadiplandra brazzeana*+ (Brazzein Protein) | Mg | 5 | 0.11% |
| *Pentadiplandra brazzeana*+ (Pentadin Protein) | Mg | 5 | 0.11% |
| *Stevia rebaudiana*+ | Mg | 20 | 0.42% |
| *Synsepalum dulcificum*+ (Miraculin Protein) | Mg | 5 | 0.11% |
| Chemical |  |  |  |
| Erythritol | Mg | 4500 | 94.96% |
| Trehalose | Mg | 200 | 4.22% |
| Total Weight | G | 4.74 | 100.00% |

TABLE 11M

Composition Of A Mixture Of Sugar Free Super-Sweetener

|  | Unit | +/−50% | WT % |
|---|---|---|---|
| Botanical |  |  |  |
| *Capparis masaikai*+ (Mabinlins Protein) | Mg | 1 | 0.02% |
| *Curculigo latifolia*+ (Curculin Protein) | Mg | 1 | 0.02% |
| *Dioscoreophyllum cumminsii*+ (Monellin Protein) | Mg | 5 | 0.04% |
| *Pentadiplandra brazzeana*+ (Brazzein Protein) | Mg | 5 | 0.11% |
| *Pentadiplandra brazzeana*+ (Pentadin Protein) | Mg | 5 | 0.11% |
| *Stevia rebaudiana*+ | Mg | 20 | 0.42% |
| *Synsepalum dulcificum*+ (Miraculin Protein) | Mg | 5 | 0.11% |
| Chemical |  |  |  |
| Erythritol | Mg | 4500 | 94.90% |
| Trehalose | Mg | 200 | 4.22% |
| Total Weight | G | 4.74 | 100.00% |

+Meaning a component (meaning an extract or a powder or a bioactive compound or a bioactive molecule from any part of the specific plant)

Nanoemulsion/Nanodispersion/Nanosuspension

An oil dissolved bioactive compound 100 (e.g., curcumin in coconut oil) and an anti-solvent (e.g., water) are individually pressurized to collide head-on at a high velocity to form nanoemulsion/nanodispersion/nanosuspension of the (oil dissolved) bioactive compound 100 (in the anti-solvent).

Furthermore, nanoparticles of the bioactive compound 100 can be realized after evaporating the anti-solvent of nanoemulsion/nanodispersion/nanosuspension.

Furthermore, nanoemulsion/nanodispersion/nanosuspension/nanoparticle can enhance the efficacy and/or bioavailability of the bioactive compound 100 at a lower concentration.

Targeted Delivery: Nanoencapsulation

FIG. 6A illustrates a bioactive compound 100 and a bioactive molecule 100A respectively.

FIG. 6B illustrates the bioactive compound 100 and bioactive molecule 100A, which is encapsulated/caged in a nanoshell 120.

The size of the nanoshell 120 is about 25 nm to 115 nm in diameter and generally spherical in shape.

The nanoshell 120 can be biodegradable and less toxic.

By way of an example and not by way of any limitation, the nanoshell 120 can be a boron nitride nanotube, carbon nanotube, cubisome, dendrimer (including plant based dendrimer), deoxyribonucleic acid (DNA) origami nanostructure, fullerene $C_{60}$ (e.g., malonic acid derivative of $C_{60}$), liposome, mesoporous silica, micelle, nanocrystal, niosome, polysebacic acid (PSA), polysilsesquioxane (PSQ), quantum dot, ribonucleic acid (RNA) origami nanostructure, self-assembling peptide (or self-assembling protein), solid-lipid nanoparticle, synthasome, tubular/tetrahedral structure fabricated/constructed by DNA/RNA origami process and zein-plant protein.

Furthermore, a micelle can be fabricated/constructed from an aptamer, casein protein, epigallocatechin-3-O-gallate derivative (with vitamin E at the center of epigallocatechin-3-O-gallate derivative) and polymer.

By way of an example and not by way of any limitation, the nanocrystal can be a nanodiamond or nanoHydroxyapatite. Hydroxyapatite is a form of calcium phosphate $Ca_{10}(PO_4)_6(OH)_2$.

Synthasome is a spherical hollow nanoshell and it contains an aqueous solution for protecting the bioactive compounds 100 and/or bioactive molecules 100A. The synthasome has a nanosized channel(s) (e.g., a transmembrane protein channel) to permit or deny transport of the bioactive compounds 100 and/or bioactive molecules 100A across the synthasome membrane.

Furthermore, an appropriate synthetic polymer material can be utilized to customize the characteristics (e.g., control permeability, release rate and stability) of the synthasome membrane.

The interior surface of the nanoshell 120 can be electrically charged (e.g., an opposite electrical charge polarity with respect to the electrical charge polarity of the bioactive compounds 100 and/or bioactive molecules 100A to be encapsulated/caged in the nanoshell 120) to increase the encapsulation efficiency of the bioactive compounds 100 and/or bioactive molecules 100A.

The exterior surface of the nanoshell 120 can be electrically charged to increase the delivery efficiency of the bioactive compounds 100 and/or bioactive molecules 100A.

FIG. 6C illustrates the surface of the nanoshell 120, which can be coated with an optional protective (to protect from a human body's biological fluid) functional surface 140.

The optional protective functional surface 140 can be fabricated/constructed from a casein protein.

Optionally, the nanoshell 120 can be coated with an immune shielding (to protect from a human body's inherent immune surveillance) functional surface 180.

FIG. 6D illustrates the nanoshell 120, which can be further encapsulated/caged in a nanocarrier (e.g., an artificial cell, capsosome, DNA/RNA origami nanostructure, natural biopolymer chitosan and polyethylene glycol (PEG)) 160.

The size of the nanocarrier 160 is about 200 nm to 300 nm in diameter and generally spherical in shape.

The nanocarrier 160 can be biodegradable and less toxic.

To construct a capsosome, a polymer film (containing building blocks modified with cholesterol) is deposited onto small silica spheres. Liposomes (with an immune shielding functional surface 180) are anchored to the cholesterol. Subsequently, more polymer films are added and cross-linked by disulfide bridges. Finally, the small silica spheres are etched away.

FIG. 6E illustrates the nanocarrier 160, which can be coated with the optional protective (to protect from a human body's biological fluid) functional surface 140.

The nanocarrier 160 can be coated with an immune shielding (to protect from a human body's inherent immune surveillance) functional surface 180.

A natural red blood/artificial red blood cell membrane can be utilized as an immune shielding functional surface 180.

A polymer membrane (e.g., polyethylene glycol (PEG) polymer/water-like polymer) can also be utilized as an immune shielding functional surface 180 instead of the red blood cell membrane.

Polyethylene glycol (PEG) membrane is a low-toxicity polymer and it can shield against hydrophobic and/or electrostatic interactions.

However, the natural red blood/artificial red blood can be utilized as an immune shielding functional surface 180, along with polyethylene glycol (PEG) membrane, wherein polyethylene glycol (PEG) membrane is configured to shield against hydrophobic and/or electrostatic interactions.

The extracellular space of a human brain is viscous and the viscosity can impede propagation of the nanoshell 120 in a human brain.

Considering the passage through the blood brain barrier (BBB) and viscosity in the extracellular space of a human brain, a suitable diameter for propagation is estimated between 65 nm to 115 nm.

Thus only the nanoshell 120 (without the nanocarrier 160) can be suitable for the passage through the blood brain barrier (BBB) and extracellular space of a human brain.

Biological receptors 240 are located on cell 260 of tissue 280.

A first targeting ligand 200 (e.g., cobalamin/vitamin) can recognize/match/bind with specific biological receptors 240A of 240, located on cell 260 of tissue 280.

A second targeting ligand 220 (e.g., an antibody/aptamer) can recognize/match/bind with specific biological receptors 240B of 240, located on cell 260 of tissue 280.

Both targeting ligands 200 and 220 can be utilized as dual navigators toward the biological receptors 240A and 240B respectively.

Both the nanocarrier 160 and nanoshell 120 can break, when (a) the first targeting ligand 200 recognizes/matches/binds with the specific biological receptors 240A and (b) the second targeting ligand 220 recognizes/matches/binds with the specific biological receptors 240B.

Alternatively, both the nanocarrier 160 and nanoshell 120 can break under an external condition/response (e.g., pH and light).

Thus the bioactive compounds 100 and/or bioactive molecules 100A can be delivered from the nanoshell 120 to the cell 260.

Example Applications of A Nanoshell (Can Be Decorated With Both Red Blood Cell Membrane & Polyethylene Glycol (PEG) Membrane) With A Nanocarrier (Can Be Decorated With Both Red Blood Cell Membrane & Polyethylene Glycol (PEG) Membrane)

Molecular Coupling/Reprogramming

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with the second targeting ligand 220 (e.g., a messenger RNA (m-RNA) aptamer). The nanoshell 120 can be uncapped in the cell 260, when the second targeting ligand 220 recognizes/matches/binds with a specific RNA (e.g., a messenger RNA (m-RNA)).

The bioactive compounds 100 and/or bioactive molecules 100A can be delivered from the nanoshell 120 specifically to couple and/or edit and/or modulate the specific RNA (e.g., a messenger RNA (m-RNA))—thus enabling a molecular coupling/reprogramming for disease prevention.

However, for a specific application of molecular coupling/reprogramming, only the nanoshell 120 (without the nanocarrier 160) can be utilized.

Molecular Coupling to a Virus/Programmed Suicide of a Virus Infected Cell to Inhibit Virus Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell infected with a virus.

The nanoshell 120 can be decorated with the second targeting ligand 220 (e.g., an aptamer/protein kinase R (PKR) protein) which can recognize/match/bind with a single-stranded RNA/double-stranded RNA/double-stranded DNA of a virus). The nanoshell 120 can be uncapped in the cell infected with the virus, when the second targeting ligand 220 recognizes/matches/binds with a single-stranded RNA/double-stranded RNA/double-stranded DNA of the virus in the cell.

The bioactive compounds 100 and/or bioactive molecules 100A can be delivered from the nanoshell 120 to induce the cell infected with the virus for a programmed cell suicide (e.g., via apoptotic protease activating factor 1) to inhibit the multiplication/propagation of the virus.

However, for a specific application of molecular coupling to a virus/programmed suicide of a virus infected cell to inhibit virus multiplication/propagation, only the nanoshell 120 (without the nanocarrier 160) can be utilized.

Molecular Coupling to a Cancer Cell/Programmed Suicide of a Cancer Cell to Inhibit Cancer Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cancer cell to allow the nanoshell 120 to the cancer cell.

The nanoshell 120 can be decorated with the second targeting ligand 220 (e.g., an aptamer is designed to be complementary to an RNA sequence unique to the cancer cell). The nanoshell 120 can be uncapped in the cancer cell, when the second targeting ligand 220 recognizes/matches/binds with an RNA sequence unique to the cancer cell.

The bioactive compounds 100 and/or bioactive molecules 100A can be delivered from the nanoshell 120 to induce the cancer cell 260 for a programmed cell suicide (e.g., via p53 pathway) to stop cancer multiplication/propagation.

For example a Bax activator compound can bind directly and selectively to Bax for Bax activation. When activated, Bax damages the cell's mitochondria, releasing signals to self-destruct the cell apart and digest its pieces.

However, for a specific application of molecular coupling to a cancer cell/programmed suicide of a cancer cell to inhibit cancer multiplication/propagation, only the nanoshell 120 (without the nanocarrier 160) can be utilized.

Example Applications of a Nanoshell (can be Decorated with Both Red Blood Cell Membrane & Polyethylene Glycol (PEG) Membrane) Without A Nanocarrier In many size constrained applications, the nanoshell 120 (without the nanocarrier 160) coated with an immune shielding functional surface 180 can be utilized.

The nanoshell 120 (coated with a light sensitive layer) can be activated by a suitable wavelength from an external light source (e.g., an ultraviolet/visible/infrared light source) to deliver the bioactive compounds 100 and/or bioactive molecules 100A from the nanoshell 120 to the cell 260.

Alternatively the nanoshell 120 (alternatively configured with a magnetic nanoparticle) can be activated by a suitable external magnetic field to deliver the bioactive compounds 100 and/or bioactive molecules 100A from the nanoshell 120 to the cell 260.

A specific small interfering RNA (s-RNAi) can be designed to suppress/inhibit unwanted protein manufacturing in the cell 260. The specific s-RNAi can be encapsulated/caged in the nanoshell 120. The nanoshell 120 decorated with a targeting ligand can deliver the specific s-RNAi to suppress/inhibit specific unwanted protein manufacturing to the cell 260.

Molecular Coupling to a Virus/Programmed Death of a Virus Infected Cell to Inhibit Virus Multiplication/Propagation To sense an invading virus, a cell can use a pattern recognition receptor. The pattern recognition receptor can recognize/match/bind to a molecular signature, specific to the virus. This binding causes the pattern recognition receptors to change its structural shape, thus initiating a chain-reaction of a signal (regarding the virus) to the surrounding cells.

For example, one of these pattern recognition receptors is RIG-I, which can practically target all RNA viruses. In an absence of a virus, a molecular virus sensor of RIG-1 receptor is exposed, while the domain responsible for cell signaling is hidden out of reach of the signaling machinery.

But when RIG-I receptor detects a virus, it changes its shape—waking up the cell signaling domains and triggering interferon production in the cell.

The changing shape of RIG-1 receptor can be detected upon binding of the molecular virus sensor of RIG-1 receptor with a molecular probe targeting ligand (e.g., a molecular beacon) wherein the molecular probe is configured with a suitable fluorophore.

The molecular probe (configured with the suitable fluorophore) targeting ligand can be decorated on the nanoshell 120.

Furthermore, the bioactive compound 100 and/or bioactive molecule 100A for programmed cell suicide can be encapsulated/caged in/with an ultra-sensitive photolabile protecting group (PPG). The photolabile protecting group (PPG) can be encapsulated/caged in the nanoshell 120.

Thus in-vivo fluorescence can trigger a release of the bioactive compound 100 and/or bioactive molecule 100A from the photolabile protecting group (PPG) for programmed cell suicide (e.g., via apoptotic protease activating factor 1) of the virus infected cell to inhibit virus multiplication/propagation.

However, instead of RIG-1 receptor, the nanoshell 120 can be decorated with a specific targeting ligand. The specific targeting ligand can recognize/match/bind with a single-stranded RNA/double-stranded RNA/double-stranded DNA of a virus.

Molecular Coupling to a Virus/Programmed Death of a Virus Infected Cell to Inhibit Virus Multiplication/Propagation Utilizing DNA/RNA Origami Structure Smart Nanoshell The (DNA/RNA origami structure based) nanoshell 120 can be fabricated/constructed by inputting a list of DNA/RNA strands that can be mixed together, by utilizing DNA/RNA modeling software.

DNA/RNA modeling software can predict how DNA/RNA base pairs can bind/match together to create a particular DNA/RNA origami structure.

The (DNA/RNA origami structure based) nanoshell 120 can be decorated with a targeting ligand (specific aptamer) to recognize/match/bind a target molecule in the signaling domain of RIG-1 receptor, when RIG-1 receptor changes its shape in the presence of a virus.

When the targeting ligand and target molecule recognize/match/bind in the signaling domain of RIG-1 receptor, when RIG-1 receptor changes its shape in the presence of a virus, the DNA strand can be configured to unzip, unlocking the (DNA/RNA origami structure based) nanoshell 120 and releasing the bioactive compound 100 and/or bioactive molecule 100A for programmed cell suicide (e.g., via apoptotic protease activating factor 1) of a virus infected cell to inhibit virus multiplication/propagation.

However, instead of RIG-1 receptor, the (DNA/RNA origami structure based) nanoshell 120 can be decorated with a specific targeting ligand. The specific targeting ligand can recognize/match/bind with a single-stranded RNA/double-stranded RNA/double-stranded DNA of a virus.

To enhance specificity, two targeting ligands (two specific aptamer based targeting ligands) instead of one targeting ligand can also be utilized.

Thus it would require two different matching signals in order to unzip the (DNA/RNA origami structure based) nanoshell 120.

Synthesis of Protein On-Demand

An amino acid, a DNA/modified DNA (wherein the DNA/modified DNA encapsulated/caged in/with a photolabile protecting group (PPG)) and a ribosome can be encapsulated/caged in the nanoshell 120.

For example, a nano-sized hole in a DNA can be drilled by an atomic beam to insert/delete a suitable atom or a molecule in order to fabricate/construct the modified DNA.

An incident light can activate the photolabile protecting group (PPG) to synthesize a desired protein on-Demand in vitro and in vivo. The nanoshell 120 can then deliver the desired protein directly to the cell 260. The desired protein can be utilized as a treatment against a disease.

Alzheimer's Disease

Shape and/or electrical polarity of the nanoshell 120 can be important parameters to suppress/inhibit Alzheimer's disease.

A tubular shaped nanoshell 120 can enhance/promote amyloid beta (Aβ) protein, increasing rate of decline in cognitive abilities in a human brain.

A negative electrical charged and tetrahedral shaped nanoshell 120 can distort and suppress/inhibit amyloid beta (Aβ) protein, significantly decreasing rate of decline in cognitive abilities in a human brain.

A specific small interfering RNA (s-RNAi) can be designed to suppress/inhibit unwanted protein manufacturing in the cell 260. The specific s-RNAi can be encapsulated/caged in the nanoshell 120. The nanoshell 120 decorated with a targeting ligand, wherein the targeting ligand can recognize/match/bind with adenosine receptors—thus allowing the blood brain barrier to be opened for the passage of the nanoshell 120 to deliver a specific s-RNAi to suppress/inhibit unwanted protein manufacturing in a human brain.

Alzheimer's disease can be caused by a loss of synapses (between neurons) due to disintegration of tau protein, wherein tau protein can interact with amyloid beta (Aβ) protein.

Ageing and/or poor autophagy can upregulate amyloid precursor protein (APP) cleaving enzyme: Bace1 (β-secretase-a molecular scissor).

Bace1 (β-secretase) can cut amyloid precursor protein (APP) to produce amyloid beta (Aβ) protein and another small fragment called AICD. Both amyloid beta (Aβ) protein and AICD can be linked to Alzheimer's disease. If Bace1 (β-secretase) is acetylated via activation of ATase1 enzyme and ATase2 enzyme, then Bace1 (β-secretase) can travel through the cell in a series of steps to produce amyloid precursor protein (APP). If Bace1 (β-secretase) is not acetylated, then Bace1 (β-secretase) takes a different pathway toward degradation.

RanBP9 protein can push amyloid precursor protein (APP) at the cell (neuron cell) edge, wherein both Bace1 (β-secretase-a molecular scissor) and presenilin complex (γ-secretase-a molecular scissor) can cut amyloid precursor protein (APP) to generate amyloid beta (Aβ) protein.

A potential prevention and/or treatment of Alzheimer's disease can be achieved by suppressing/inhibiting RanBP9 protein manufacturing. RanBP9 protein is encoded by RanBP9 gene.

Curcumin (e.g., a nanoformulated curcumin) can suppress/inhibit RanBP9 protein manufacturing in a human brain.

Cucurbitacin (e.g., Cucurbitacin E) can suppress/inhibit RanBP9 protein manufacturing in a human brain. Nanoformulated cucurbitacin can enhance the efficacy and/or bioavailability at a lower concentration.

Metformin (N,N-dimethylimidodicarbonimidic diamide) can suppress/inhibit RanBP9 protein manufacturing in a human brain.

An anti-cancer compound imatinib mesylate can suppress/inhibit RanBP9 protein manufacturing in a human brain. But imatinib mesylate cannot pass through the blood brain barrier Imatinib mesylate is 4-[(4-Methyl1-piperazinyl)methyl]-N-[4-methyl-3-[[4-(3-pyridinyl)-2-pyrimidinyl]amino]-phenyl]benzamide methanesulfonate and its structural formula is shown below:

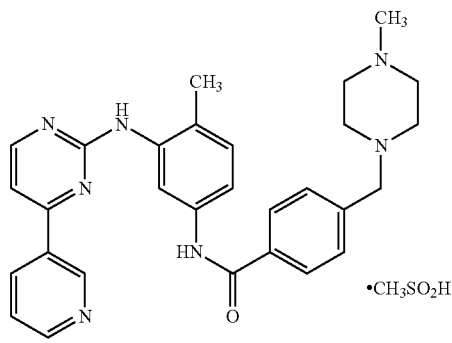

The molecular formula of Imatinib mesylate is $C_{29}H_{31}N_7O \cdot CH_4SO_3$ and its molecular weight is 589.7.

Imatinib mesylate can be encapsulated/caged in the nanoshell 120. The nanoshell 120 decorated with a targeting ligand, wherein the targeting ligand can recognize/match/bind with adenosine receptors—thus allowing the blood brain barrier to be opened for the passage of the nanoshell 120 to deliver imatinib mesylate to suppress/inhibit RanBP9 protein manufacturing in a human brain.

Nanoformulated imatinib mesylate can enhance the efficacy and/or bioavailability at a lower concentration.

Sodium phenylbutyrate can suppress/inhibit RanBP9 protein manufacturing in a human brain.

An anti-cancer compound dasatinib can suppress/inhibit RanBP9 protein manufacturing in a human brain.

The dasatinib is N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate and its structural formula is shown below:

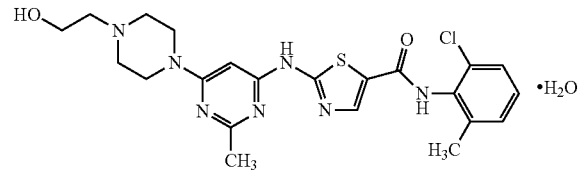

The molecular formula of dasatinib is $C_{22}H_{26}ClN_7O_2S \cdot H_2O$ and its molecular weight is 506.02 (monohydrate).

Nanoformulated dasatinib can enhance the efficacy and/or bioavailability at a lower concentration.

Dasatinib can be encapsulated/caged in the nanoshell 120. The nanoshell 120 decorated with a targeting ligand, wherein the targeting ligand can recognize/match/bind with adenosine receptors—thus allowing the blood brain barrier to be opened for the passage of the nanoshell 120 to deliver dasatinib to suppress/inhibit RanBP9 protein manufacturing in a human brain.

Affibody molecule (an engineered protein) can be encapsulated/caged in the nanoshell 120. The nanoshell 120 decorated with a targeting ligand, wherein the targeting ligand can recognize/match/bind with adenosine receptors—thus allowing the blood brain barrier to be opened for the passage of the nanoshell 120 to deliver affibody molecule to suppress/inhibit formation of amyloid beta (Aβ) protein in a human brain.

PARK7 gene (known as DJ-1) can protect cells (neurons) against oxidative damage. Sodium phenylbutyrate and/or a short protein fragment of non-mutated PARK7 can turn on PARK7 gene (known as DJ-1) to protect against oxidative damage.

Sodium phenylbutyrate and/or a short protein fragment of non-mutated PARK7 can be encapsulated/caged in the nanoshell 120. The nanoshell 120 decorated with a targeting ligand, wherein the targeting ligand can recognize/match/bind with adenosine receptors—thus allowing the blood brain barrier to be opened for the passage of the nanoshell 120 to deliver sodium phenylbutyrate and/or a short protein fragment of non-mutated PARK7 to protect against oxidative damage.

Diabetes Disease

Long acting insulin derivative [2-sulfo-9fluoroenyl-methoxycarbonyl]-3insulin and leptin (or a chemical derivative/structural analog of leptin) can be encapsulated/caged in a pH responsive nanoshell 120. The pH responsive nanoshell 120 can be delivered for oral intake/inhale.

A specific small interfering RNA (s-RNAi) can be designed to suppress/inhibit cryptochrome protein manufacturing. The specific s-RNAi can be encapsulated/caged in the nanoshell 120. The nanoshell 120 can deliver the specific s-RNAi to suppress/inhibit cryptochrome protein manufacturing.

Hearing Loss Disease

Free radicals can induce manufacturing of Bak, a protein. Bak protein can trigger suicide of cells (these cells do not regenerate like other cells in a human body) in the auditory portion of the inner ear.

The level of Bak protein can also increase with ageing.

A specific small interfering RNA (s-RNAi) can be designed to suppress/inhibit Bak protein manufacturing. The specific s-RNAi can be encapsulated/caged in the nanoshell 120. The nanoshell 120 can deliver the specific s-RNAi (locally through the round window membrane (RWM) of the inner ear) to suppress/inhibit Bak protein manufacturing in a human ear.

The administration of the bioactive compound 100 and/or bioactive molecule 100A to treat hearing loss disease is the permeation of the round window membrane (RWM). The ultra-fine structure of the round window membrane is not well known, but there are vesicles in the round window membrane (RWM), wherein clathrin and caveolin pathways may be involved in the transportation of the nanoshell 120 through round window membrane (RWM).

Furthermore, the nanoshell 120 can be decorated with targeting ligands, which can bind to specific receptors on spiral ganglion cells (Trk-B receptors) and on the vasculature (the matrix metalloproteins, MMP2).

Brain-derived neurotrophic factor (BDNF) can interact with Trk-B receptors.

Furthermore, cell entry of the nanoshell 120 can be facilitated by a viral-TAT peptide (e.g., TAT-Influenza-HA), binding of the nanoshell 120 with Trk-B receptors can be facilitated by brain-derived neurotrophic factor ligand and nuclear pore complex entry of the nanoshell 120 can be facilitated by a nuclear targeting peptide.

Furthermore, brain-derived neurotrophic factor, Atoh1/Math1 gene (for growth of hair cells), s-RNAi (designed to suppress/inhibit Bak protein manufacturing in a human ear), MRI contrast agent and molecular tags can be encapsulated/caged in the nanoshell 120—thus realizing a multifunctional nanoshell.

Premature Ageing (Progeria) Disease

A cellular instability leading to premature aging (Progeria) disease can be caused by toxic Lamin A protein. Toxic Lamin A protein is manufactured due to a mutation in the LMNA gene. A specific small interfering RNA (s-RNAi) can be designed to suppress/inhibit toxic Lamin A protein manufacturing. The nanoshell 120 can deliver the specific s-RNAi to suppress/inhibit toxic Lamin A protein manufacturing.

Furthermore, Lamin A protein interacts with SUN 1 protein. The nanoshell 120 can deliver the specific s-RNAi to suppress/inhibit SUN 1 protein manufacturing.

Inflammation

Reactive oxygen species (ROS) can cause an inflammation in cardiovascular, hearing loss, infection and neurological diseases. An accumulation of reactive oxygen species (ROS) can result in manifestation hydrogen peroxide or hypochlorous acid.

Hydrogen peroxide or hypochlorous acid sensitive nanoshell 120 can degrade in presence of a minute amount of hydrogen peroxide or hypochlorous acid in order to deliver the bioactive compound 100 and/or bioactive molecule 100A to reduce the inflammation in cardiovascular, hearing loss, infection and neurological diseases.

Delivery of Bioactive Compounds &/or Bioactive Molecules from a Nanoshell: a Nanoshell Configured with a Bacterium/Microbe/Genetically Engineered Microbe The nanoshell 120 can be configured with a harmless bacterium (e.g., *lactobacillus*)/microbe/genetically engineered microbe to deliver the bioactive compounds 100 and/or bioactive molecules 100A.

Delivery of Bioactive Compounds &/or Bioactive Molecules from a Nanotube: a Nanotube Configured with a Nanopump A nanotube (e.g., a boron nitride/carbon nanotube or a tubular/tetrahedral structure, fabricated/constructed by DNA/RNA origami process) can cross a cell membrane and enter the nuclei of the cell, while the cell may not recognize the nanotube as an unfriendly intruder. The nanotube can be biodegradable and less toxic.

The uptake of the bioactive compounds 100 and/or bioactive molecules 100A from a solution into the nanotube can be achieved by Van der Waals attraction between the nanotube and the bioactive compounds 100 and/or bioactive molecules 100A.

The nanotube's exterior surface can be can be coated with (a) an optional protective (to protect from a human body's biological fluid) functional surface and (b) an immune shielding (to protect from a human body's inherent immune surveillance) functional surface.

Furthermore, the nanotube's exterior surface can be decorated with a targeting ligand to recognize/match/bind with specific biological receptors on the cell to allow the nanotube to the cell.

Therefore the bioactive compounds 100 and/or bioactive molecules 100A can be delivered to the cell with unprecedented accuracy and efficiency.

A nanopump configured by prestin motor protein can generate a sustained mechanical wave in the nanotube to release/eject the bioactive compounds 100 and/or bioactive molecules 100A from the nanotube.

Prestin is a motor protein enabling direct voltage-to-force converter.

Thus a battery (fabricated/constructed from engineered M13 bacteriophage) coupled with prestin motor protein can act as a nanopump.

M13 bacteriophage can translate mechanical energy into electrical energy. To improve the piezoelectric property of M13 bacteriophage, the outer protein layer of M13 bacteriophage can be engineered by adding appropriate molecules.

Furthermore, to amplify piezoelectric effect, multi-layers of engineered M13 bacteriophage can be utilized.

Multi-layers of engineered M13 bacteriophage can then be sandwiched between two biocompatible electrodes to act as a battery, when stressed mechanically (e.g., by a cardiac cycle).

Targeted Delivery to Mitochondria

The mitochondria are the power plants of cells. Mitochondria generate most of the cell's supply of adenosine triphosphate (ATP). Adenosine triphosphate (ATP) is used as a source of chemical energy.

While mitochondria are present in all cells, in some cells, because of their size and purpose—need to transport mitochondria at proper positions within the cell to maintain proper function of the cell.

For example, neurons have a complex cellular structure of a main cell body and enormous arms of axons and dendrites that fan out from the cell core and transmit signals to adjoining cells via synapses at their terminus.

Thus the supply chain including mitochondria is very long. Mitochondria are also constantly cycling throughout the neuron. Neurons can transport mitochondria (some mitochondria are stationary/fixed, while other mitochondria are mobile) down the enormous arms of axons and dendrites at proper positions to provide other parts of the cell with energy, help with the transmission of signals and maintenance of the cellular health.

Additionally, at any given time about half of the mobile mitochondria in the neurons are returning to the cell—to be recycled/replenished.

One interesting property of mitochondria is that they have their own DNA. Mitochondrial DNA is different from chromosomal/nuclear DNA. First, it exists as a simple plasmid (a DNA loop) than the chromosomal/nuclear DNA. Second, most repair mechanisms to correct chromosomal/nuclear DNA are missing from mitochondrial DNA. Thus relatively unprotected/unrepairable mitochondrial DNA can suffer about 10 times more damage than chromosomal/nuclear DNA.

Mitochondrial electron transport is not perfect. Even under ideal mitochondrial conditions, some electrons can leak from the electron transport chain. These leaking electrons can interact with oxygen to produce superoxide radicals.

Furthermore, with mitochondrial dysfunction, leakage of electrons can increase significantly.

The close proximity of mitochondrial DNA to the flux of superoxide radicals (or hydroxyl radicals) and the lack of mitochondrial protection/repair mechanism can lead to mitochondrial dysfunction.

Many diseases can be related to mitochondrial dysfunction—thus an ability to transport the bioactive compounds 100 and/or bioactive molecules 100A to mitochondria specifically can be beneficial.

Furthermore, the disruptive changes to mitochondria can occur when both amyloid beta (Aβ) protein and tau protein (rather truncated version of tau protein, not regular version of tau protein) are present together and the disruptive changes are: (a) about 30% remaining electrical potential (but 100% electrical potential is needed to produce energy efficiently), (b) abnormal mitochondria clumping, (c) fragmentation of mitochondria, (d) incorrect control of calcium level correctly and (e) release of (toxic) free radicals.

Triphenylphosphonium (TPP) can pass through and accumulate several hundred folds in mitochondrial matrix.

The bioactive compounds 100 and/or bioactive molecules 100A can be chemically coupled with triphenylphosphonium (TPP)/chemical derivative of triphenyl phosphonium (TPP)/structural analog of triphenylphosphonium (TPP) to enhance an uptake of the bioactive compounds 100 and/or bioactive molecules 100A in mitochondria.

A Passive Micropatch

Figure 7A:
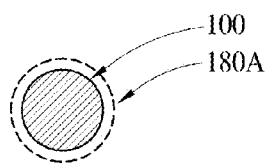
FIGS. 7A, 7B, 7C, 7D, 7E, 7F, 7G, 7H, 7I, 7J, 7K, 7L and 7M illustrate a passive (via a micropatch) delivery of bioactive compounds and/or bioactive molecules, utilizing thin-films, nanocrystals and microelectro-mechanical-system (MEMS) reservoirs.

FIG. 7A illustrates an expanded view of a negative electrical charged surface 180A on the bioactive compound 100.

Figure 7B:
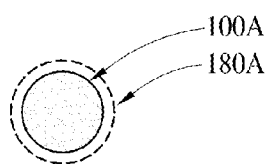

FIG. 7B illustrates an expanded view of a negative electrical charged surface 180A on the bioactive molecule 100A.

Figure 7C:
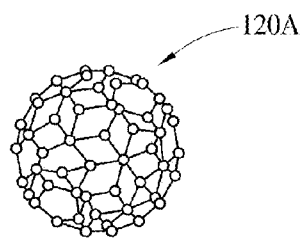

FIG. 7C illustrates an expanded view of a nanocrystal 120A.

Figure 7D:
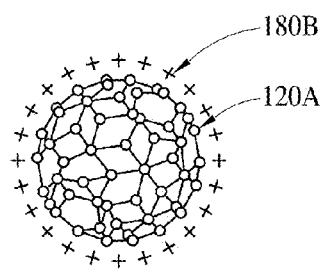

FIG. 7D illustrates expanded view of a positive electrical charged surface 180B on the nanocrystal 120A.

The charge conjugation can increase the encapsulation efficiency and/or delivery efficiency of the bioactive compounds 100 and/or bioactive molecules 100A.

Figure 7E:
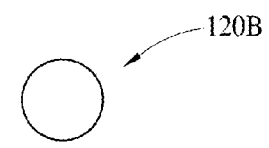

FIG. 7E illustrates an expanded view of a fluorophore (e.g., a quantum dot fluorophore) 120B.

With a quantum dot fluorophore, the size of the bandgap can be controlled by varying the diameter of the quantum dot. Larger diameter (e.g., 10 nm in diameter) quantum dot fluorophore will have a smaller bandgap, thus the larger diameter quantum dot fluorophore will fluoresce in the red part of the optical spectrum. Conversely, smaller diameter (e.g., 5 nm in diameter) quantum dot fluorophore will have a larger bandgap, thus the smaller diameter quantum dot fluorophore will fluoresce in the blue part of the optical spectrum.

Figure 7F:
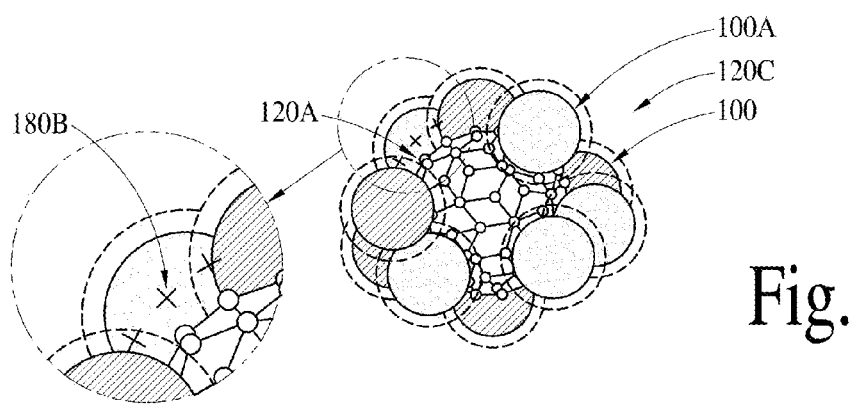

FIG. 7F illustrates 120C, wherein the negative electrical charged bioactive compounds 100 and/or bioactive molecules 100A are surrounded by a cluster of the positive electrical charged nanocrystals 120A.

Figure 7G:
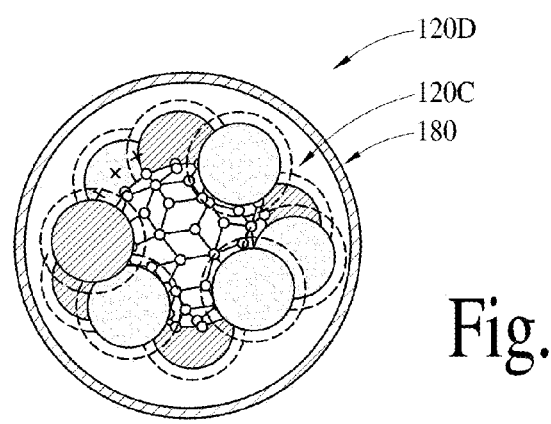

FIG. 7G illustrates 120D, wherein 120C is chemically bonded with the immune shielding functional surface 180.

Figure 7H:
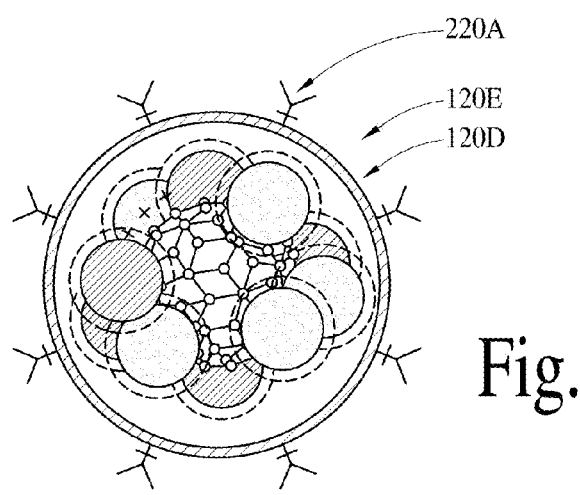
Figure 7:
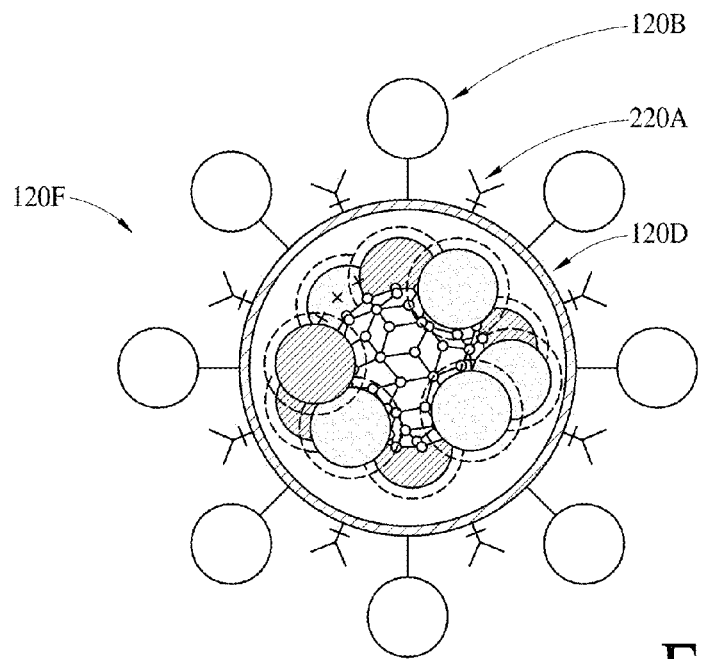
FIG. 7N illustrates a programmable/active (via a micropatch and MEMS reservoir(s) integrated with needles) delivery of bioactive compounds and/or bioactive molecules, utilizing thin-films, nanocrystals, hydrogels, MEMS reservoirs and micropumps.
FIG. 7O illustrates a programmable/active (via a micropatch and MEMS reservoir(s) integrated with nanotubes) delivery of bioactive compounds and/or bioactive molecules, utilizing thin-films, nanocrystals, hydrogels, MEMS reservoirs and micropumps.
Figure 7:
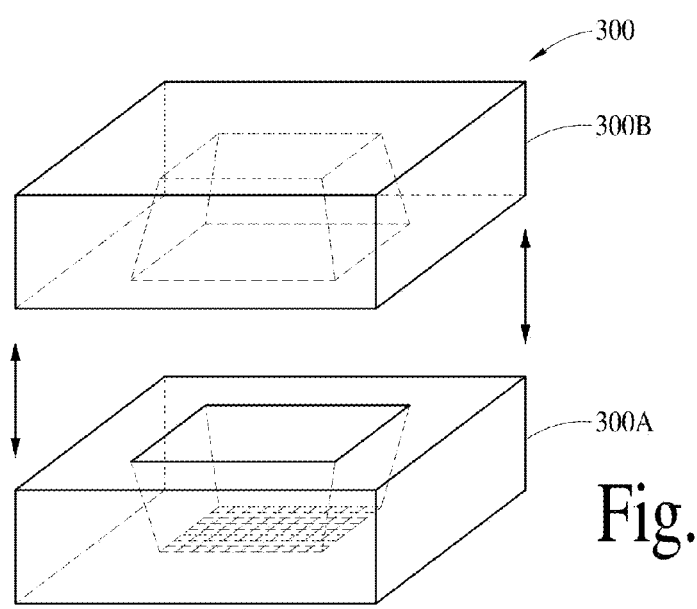

FIG. 7H illustrates 120E, wherein 120D can be chemically bonded with a specific targeting ligand 220A.

FIG. 7I illustrates 120F, wherein 120E is optionally chemically bonded with the fluorophore 120B.

The above nanoassembly 7I can be utilized for targeted delivery of the bioactive compounds 100 and/or bioactive molecules 100A.

FIG. 7J illustrates a microelectromechanical systems (MEMS) reservoir 300.

MEMS reservoir 300 can be fabricated/constructed from liquid crystal polymers/polyimide/silicon/silk/SU-8 resin/other suitable material.

Figure 7K:
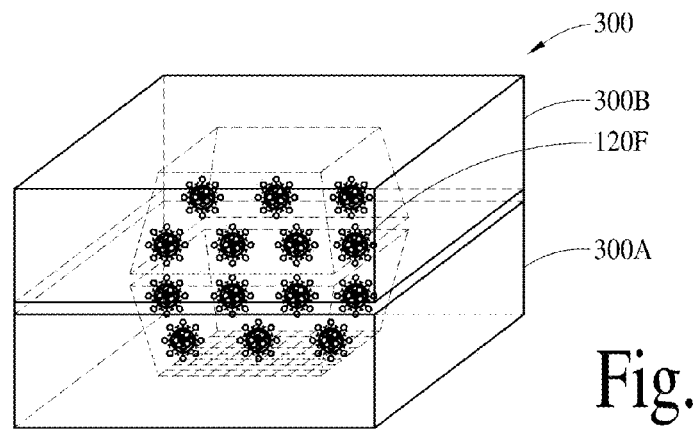

FIG. 7K illustrates 120Fs. 120Fs are inserted/caged in the MEMS reservoir 300.

Figure 7L:
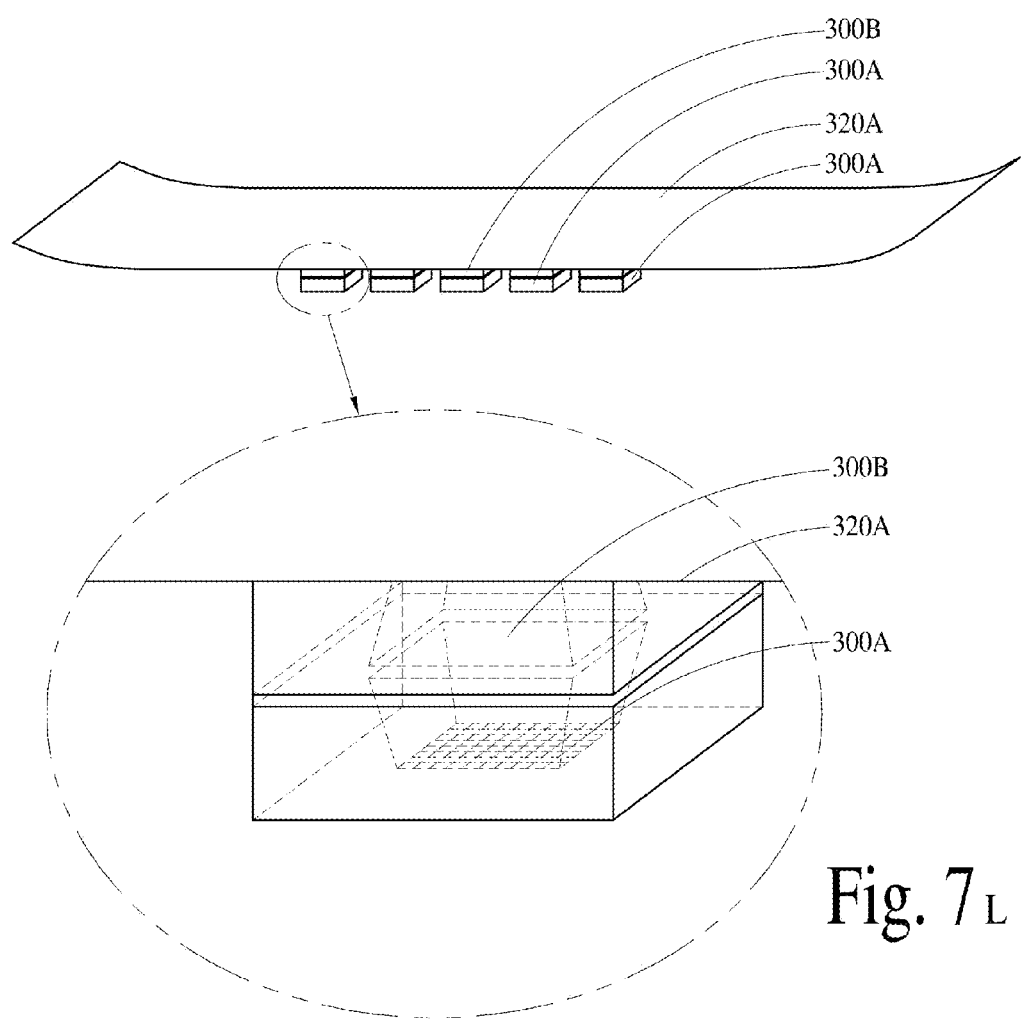

FIG. 7L illustrates the top surface 300B of the MEMS reservoir 300. 300B can be attached onto a non-porous adhesive top thin-film 320A.

The porous bottom surface of the MEMS reservoir 300 is 300A. 300A can be attached onto a biological transport medium (e.g., skin) for delivery of the bioactive compounds 100 and/or bioactive molecules 100A.

Thus a long-term passive micropatch (about 15 mm$^2$ in area) (with the porous bottom surface of the MEMS reservoir) can be fabricated/constructed for delivery of the bioactive compounds 100 and/or bioactive molecules 100A.

The porous bottom surface of the MEMS reservoir 300 is 300A. Furthermore, 300A can be attached onto a nanoporous membrane (e.g., a nanoporous membrane of titanium dioxide nanotubes), then onto a biological transport medium for delivery of the bioactive compounds 100 and/or bioactive molecules 100A.

Thus a long-term passive micropatch (about 15 mm$^2$ in area) (with the porous bottom surface of the MEMS reservoir and nanoporous membrane) can be fabricated/constructed for the delivery of the bioactive compounds 100 and/or bioactive molecules 100A.

Figure 7M:
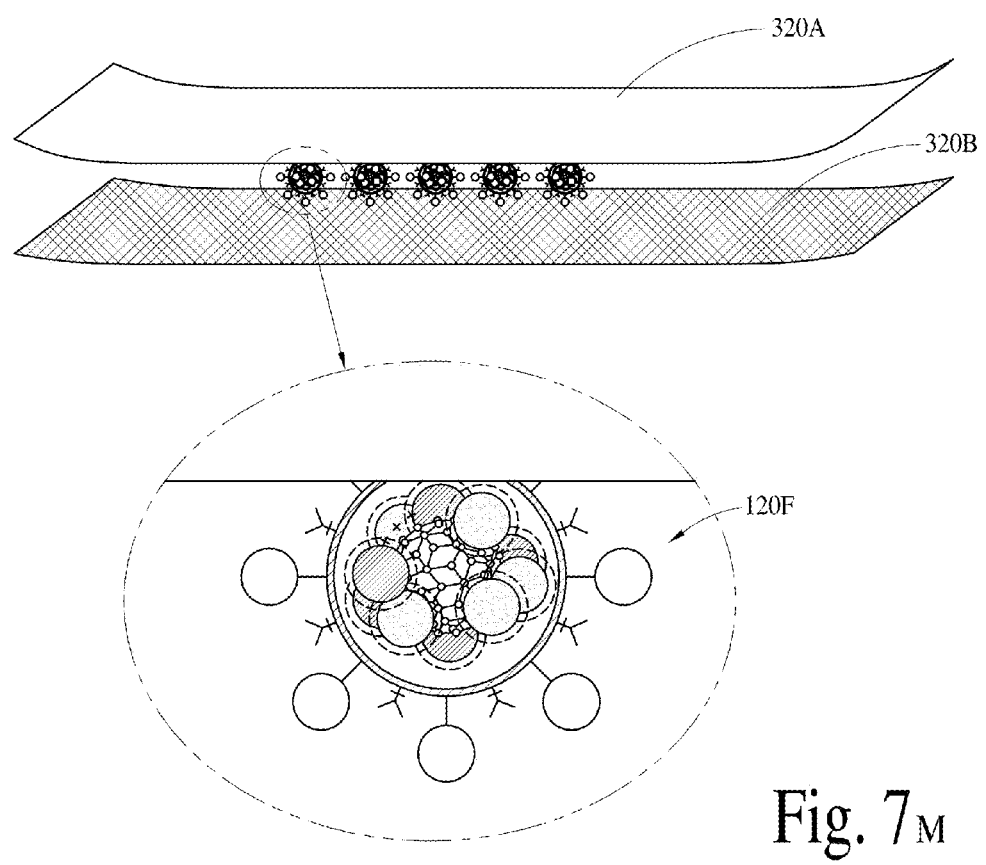

FIG. 7M illustrates 120F bonded directly between a non-porous adhesive top thin-film 320A and a porous bottom adhesive thin-film 320B. The porous bottom thin-film 320B can be attached onto a biological transport medium.

Thus a short-term passive micropatch (about 15 mm$^2$ in area) (with the porous bottom adhesive thin-film) can be fabricated/constructed for delivery of the bioactive compounds 100 and/or bioactive molecules 100A.

A Two-Dimensional (2-D) Array of Nanosized Wells of a Porous Material, as an Alternative to a MEMS Reservoir Alternatively, a two-dimensional (2-D) array of nanosized wells of a suitable porous material (e.g., porous hydrogel/porous silicon/silicate based polymer nanocomposite) containing the bioactive compounds 100 and/or bioactive molecules 100A (or indirectly utilizing nanocrystals, wherein the nanocrystals encapsulate/cage the bioactive compounds 100 and/or bioactive molecules 100A) can replace the above MEMS reservoir 300 in both the long-term/short-term passive micropatch.

The two-dimensional (2-D) array of nanosized wells of the suitable porous material thin-film can be fabricated/constructed by lithography (e.g., phase mask lithography/electron beam lithography) and inductively-coupled plasma (ICP) etching.

A Smart Porous Thin-Film, as an Alternative to a MEMS Reservoir

A smart thin-film (e.g., a composite-gel) can regulate permeability in response to an external stimulus.

The smart thin-film can contain an ordered array of nanochannels.

Furthermore, the ordered array of nanochannels can contain an ordered array of magnetic polystyrene latex particles.

The magnetic polystyrene latex particle can change its size in response to an external stimulus (e.g., temperature). Expansion/contraction of the magnetic polystyrene latex particles can affect the permeability of the smart porous thin-film from on state to off state.

Thus, a controlled and/or tunable transport of the bioactive compounds 100 and/or bioactive molecules 100A can be achieved, by utilizing the suitable smart porous material thin-film.

Other bio/health sensors to monitor vital health parameters (e.g., blood sugar and heart rate) can be integrated with the long-term/short-term passive micropatch.

Furthermore, Wibree/Bluetooth/near field communication/WiFi can be integrated with the long-term/short-term passive micropatch.

Example Applications of a Passive Micropatch 7M can be utilized as a passive micropatch to deliver a compound, drug, molecule (e.g., a micro RNA (mi-RNA) and small interfering RNA (s-RNAi)) and protein.

7M can be utilized as a passive micropatch to deliver an antibiotic bioactive compound.

Furthermore, an antibiotic bioactive compound can be integrated with magnesium oxide nanoparticles, self-assembling peptides (e.g., RADA16-I) and silver nanoparticles.

7M can be utilized as a passive micropatch to deliver sildenafil.

7M can be utilized as a passive micropatch to deliver testosterone.

7M can be utilized as a passive micropatch to deliver luric acid and/or an isolated active protein from the *propionibacterium acnes* phages for treatment against acne.

*Propionibacterium acnes* phages, (a family of harmless viruses that live on human skin) are naturally programmed to kill the *propionibacterium acnes*, a bacterium that triggers acne.

7M can be utilized as a passive micropatch to deliver rivastigmine for treatment against Alzheimer's disease.

7M can be utilized as a passive micropatch to deliver rotigotine for treatment against Parkinson's disease.

Bacteria outnumber human cells about ten to one. A human body has a complex network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

7M can be utilized as a passive micropatch to deliver a pro-quorum sensing compound.

7M can be utilized as a passive micropatch to deliver an anti-quorum sensing compound.

7M can be placed (attached and/or implanted) on or in (meaning within) a human body.

An Active Micropatch Integrated with an Electrically Controlled Layer

The porous bottom thin-film 320B can be composed of electrically charged (an opposite electrical charge polarity with respect to the electrical charge polarity of nanocrystals 120A) pigmented layers. Electrically charged pigmented layers can hold (an opposite electrical charge polarity) electrically charged nanocrystals 120A by an electrostatic field.

By applying a voltage (about millivolts from a printed thin-film battery), the electrically charged pigmented layers can disintegrate.

Thus the bioactive compounds 100 and/or bioactive molecules 100A can be delivered in a variable quantity from the electrically charged nanocrystals 120A.

An Active Micropatch Integrated with an Electrically Controlled Layer & a Smart Porous Thin-Film The porous bottom thin-film 320B can be composed of a smart thin-film.

A smart thin-film (e.g., a composite-gel) can regulate permeability in response to an external stimulus.

The smart thin-film can contain an ordered array of nanochannels.

Furthermore, the ordered array of nanochannels can contain an ordered array of magnetic polystyrene latex particles.

The magnetic polystyrene latex particle can change its size in response to an external stimulus (e.g., temperature). Expansion/contraction of the magnetic polystyrene latex particles can affect the permeability of the smart porous thin-film from on state to off state.

Thus, a controlled and/or tunable transport of the bioactive compounds 100 and/or bioactive molecules 100A can be achieved, by utilizing the suitable smart porous material thin-film.

Other bio/health sensors to monitor vital health parameters (e.g., blood sugar and heart rate) can be integrated with the active micropatch.

Furthermore, Wibree/Bluetooth/near field communication/WiFi can be integrated with the active micropatch.

Example Applications of an Active Micropatch Integrated with Electrically Controlled Layer An active micropatch can be utilized to deliver a compound, drug and molecule (e.g., a micro RNA (mi-RNA) and small interfering RNA (s-RNAi)).

An active micropatch can be utilized to deliver an antibiotic bioactive compound.

Furthermore, an antibiotic bioactive compound can be integrated with magnesium oxide nanoparticles, self-assembling peptides (e.g., RADA16-I) and silver nanoparticles.

An active micropatch can be utilized to deliver sildenafil.

An active micropatch can be utilized to deliver testosterone.

An active micropatch can be utilized to deliver luric acid and/or an isolated active protein from the *propionibacterium acnes* phages for treatment against acne.

An active micropatch can be utilized to deliver rivastigmine for treatment against Alzheimer's disease.

An active micropatch can be utilized to deliver rotigotine for treatment against Parkinson's disease.

Bacteria outnumber human cells ten to one. A human body has a complex molecular network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

An active micropatch can be utilized to deliver a pro-quorum sensing compound.

An active micropatch can be utilized to deliver an anti-quorum sensing compound.

An active micropatch can be placed (attached and/or implanted) on or in (meaning within) a human body.

An Active Micropatch Integrated with MEMS Reservoirs & Microneedles

A passive delivery of the bioactive compounds 100 and/or bioactive molecules 100A is generally limited by a low permeability (of the bioactive compounds 100 and/or bioactive molecules 100A) in a biological transport medium.

Figure 7N:
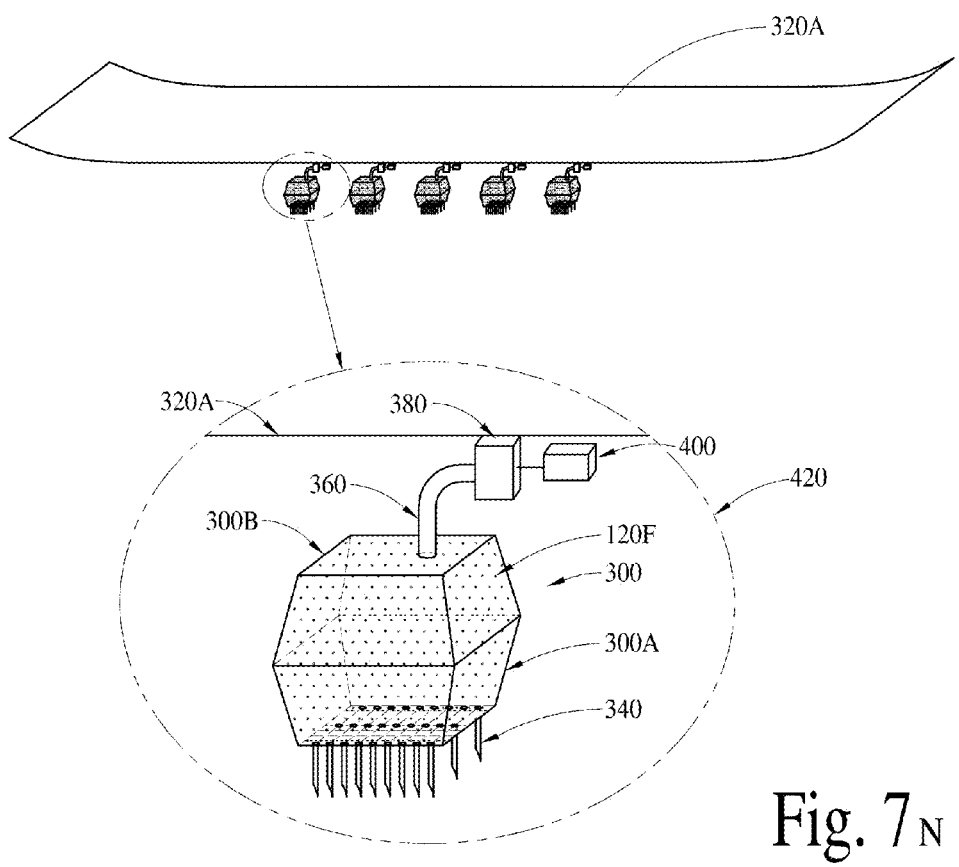

FIG. 7N illustrates a thin-film 320A attached with a MEMS microassembly as 420.

The MEMS microassembly 420 illustrates MEMS reservoirs 300 with monolithically integrated microneedles 340, utilizing a microflow tube 360.

The microflow tube 360 can be connected to a micropump 380.

The micropump 380 can be powered by an electrical power providing component 400.

The electrical power providing component 400 can be a printed thin-film battery.

M13 bacteriophage can translate mechanical energy into electrical energy.

To improve the piezoelectric property of M13 bacteriophage, the outer protein layer of M13 bacteriophage can be engineered by adding appropriate molecules.

Furthermore, to amplify piezoelectric effect, multi-layers of engineered M13 bacteriophage can be utilized.

Multi-layers of engineered M13 bacteriophage can then be sandwiched between two biocompatible electrodes to act as a battery, when stressed mechanically (e.g., by a cardiac cycle).

Furthermore, prestin is a motor protein enabling direct voltage-to-force converter.

Thus the battery (fabricated/constructed from engineered M13 bacteriophage) coupled with prestin motor protein can act as the micropump 380 (or the nanopump, as described earlier).

The MEMS reservoir 300 can be fabricated/constructed from liquid crystal polymers/polyimide/silicon/silk/SU-8 resin/other suitable material.

The MEMS reservoir 300 can be monolithically integrated with microneedles 340.

The microneedle 340 is biocompatible and about 450 micron long with an internal hole-diameter of about 45 micron.

The microneedle 340 can be fabricated/constructed from liquid crystal polymers/polyimide/silicon/silk/SU-8 resin/other suitable material.

The MEMS microassembly is indicated as 420.

Thus a long-term active micropatch (about 15 mm$^2$ in area) can be fabricated/constructed for the delivery of the bioactive compounds 100 and/or bioactive molecules 100A from the nanoassembly 120F in the MEMS reservoirs 300.

Alternatively, a hydrogel contain up to 99.7% water and 0.3% cellulose polymers by weight, wherein the polymers are held by cucurbiturils. Cucurbiturils are methylene-linked macrocyclic molecules made of glycoluril [=C4H2N4O2=] monomers. The oxygen atoms are located along the edges of the band and are tilted inwards, forming a partly enclosed cavity.

The hydrogel can protect the bioactive compounds 100 and/or bioactive molecules 100A for about six (6) months.

The hydrogel (embedded with the bioactive compounds 100 and/or bioactive molecules 100A) can be utilized in the MEMS reservoirs 300 without the nanoassembly 120F.

Alternatively, a long-term active micropatch (about 15 mm$^2$ in area) can be fabricated/constructed for the delivery of the bioactive compounds 100 and/or bioactive molecules 100A from the hydrogel (embedded with the bioactive compounds 100 and/or bioactive molecules 100A) in the MEMS reservoirs 300.

Furthermore, the bioactive compounds 100 and/or bioactive molecules 100A can be utilized directly in the MEMS reservoirs 300 without the nanoassembly 120F for a long-term active micropatch.

Other bio/health sensors to monitor vital health parameters (e.g., blood sugar and heart rate) can be integrated with the long-term active micropatch.

Furthermore, Wibree/Bluetooth/near field communication/WiFi can be integrated with the long-term active micropatch.

Example Applications of an Active Micropatch Integrated with MEMS Reservoirs & Microneedles 7N can be utilized as an active micropatch to deliver a liquid drug (e.g., immunoglobulin).

7N can be utilized as an active micropatch to deliver a liquid nanoemulsified drug.

7N can be utilized as an active micropatch to deliver insulin.

7N can be utilized as an active micropatch to deliver insulin with leptin.

7N can be utilized as an active micropatch to deliver exenatide.

7N can be utilized as an active micropatch to deliver specific micro RNA (mi-RNA).

7N can be utilized as an active micropatch to deliver specific small interfering RNA (s-RNAi).

7N can be placed (attached and/or implanted) on or in (meaning within) a human body.

An Active Micropatch Integrated with MEMS Reservoirs & Nanotubes

Figure 7O:
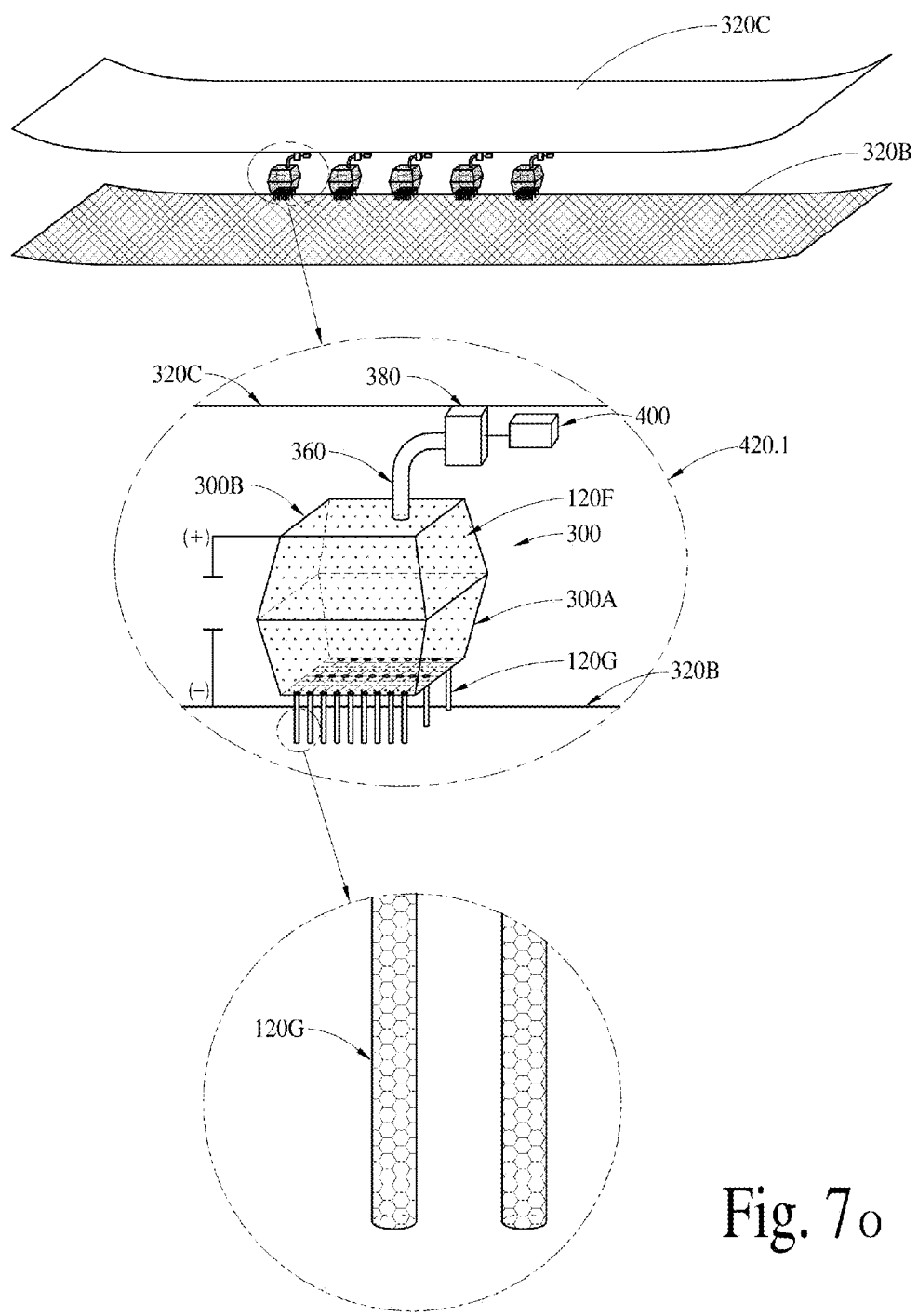

FIG. 7O illustrates a conducting thin-film 320C attached with MEMS reservoirs 300.

Furthermore, the MEMS reservoirs 300, with integrated/bonded nanotubes (e.g., a boron nitride/carbon nanotube or a tubular structure fabricated/constructed by DNA/RNA origami process) 120G, utilizing a microflow tube 360, which can be connected to a micropump 380. The MEMS microassembly is indicated as 420.1.

The micropump 380 can be powered by an electrical power providing component 400.

The electrical power providing component 400 can be a printed thin-film battery.

Thus a long-term active micropatch (about 15 mm² in area) can be fabricated/constructed for delivery of the bioactive compounds 100 and/or bioactive molecules 100A from the nanoassembly 120F.

Alternatively, a long-term active micropatch (about 15 mm² in area) can be fabricated/constructed for delivery of the bioactive compounds 100 and/or bioactive molecules 100A from the hydrogels (embedded with the bioactive compounds 100 and/or bioactive molecules 100A) in the MEMS reservoirs 300.

Furthermore, the bioactive compounds 100 and/or bioactive molecules 100A can be utilized directly within the MEMS reservoirs 300 without the nanoassembly 120F.

The nanotubes 120G can be further integrated/bonded with the porous bottom thin-film 320B.

By applying a voltage (about millivolts from a printed thin-film battery) between 320C and the nanostructure membrane 120G, the bioactive compounds 100 and/or bioactive molecules 100A can be delivered in a variable quantity according to the required dose/need.

Example Applications of An Active Micropatch Integrated With MEMS Reservoirs & Nanotubes 7O can be utilized as an active micropatch to deliver a liquid drug (e.g., immunoglobulin).

7O can be utilized as an active micropatch to deliver a nanoformulated liquid drug.

7O can be utilized as an active micropatch to deliver insulin.

7O can be utilized as an active micropatch to deliver exenatide.

7O can be utilized as an active micropatch to deliver specific micro RNA (mi-RNA).

7O can be utilized as an active micropatch to deliver specific small interfering RNA (s-RNAi).

7O can be placed (attached and/or implanted) on or in (meaning within) a human body.

Figure 8:
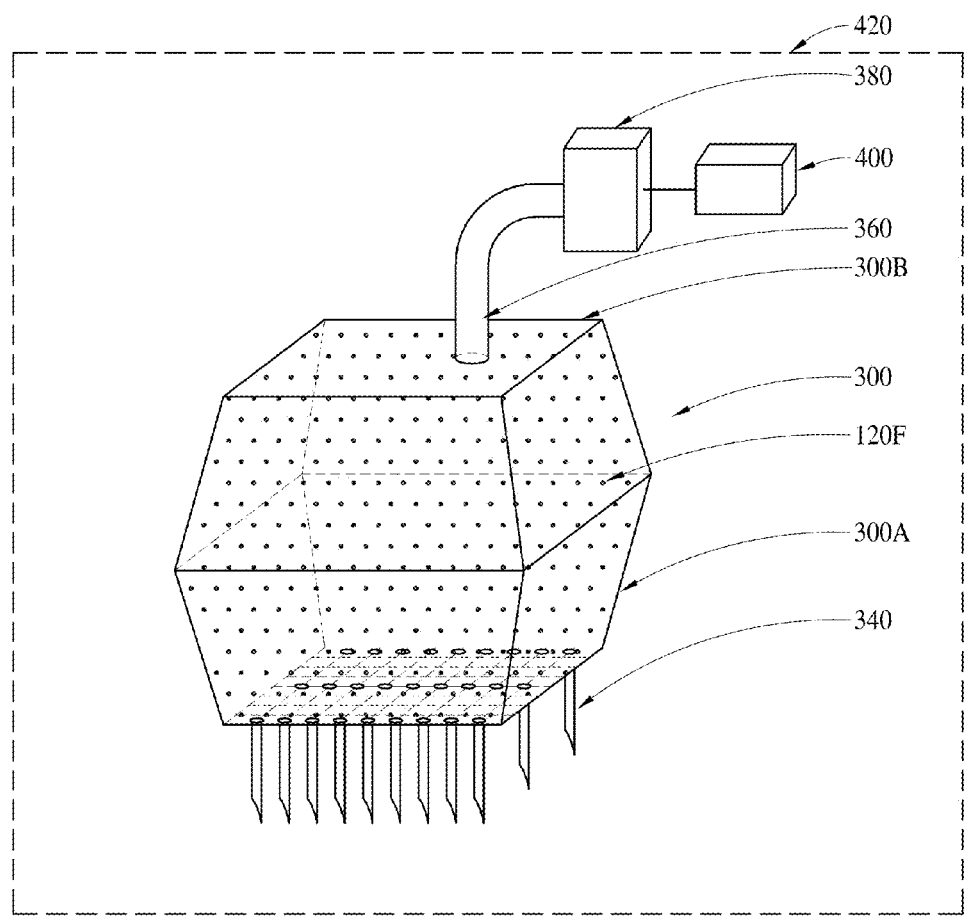
FIG. 8 illustrates a programmable/active (via a micropatch and MEMS reservoir(s) integrated with needles) delivery of bioactive compounds and/or bioactive molecules, utilizing a MEMS reservoir and a micropump.

FIG. 8 illustrates the MEMS reservoir 300 with 120Fs dispersed in a liquid medium. 120Fs can encapsulate/cage the bioactive compounds 100 and/or bioactive molecules 100A.

However, the bioactive compounds 100 and/or bioactive molecules 100A can be dispersed directly (via a liquid medium) in the MEMS reservoir 300, without the need 120F.

The MEMS reservoir 300 is about 1 mm in total thickness.

The MEMS reservoir 300 can be monolithically integrated with microneedles 340 at the bottom surface 300A of the MEMS reservoir 300.

The microneedle 340 is biocompatible and about 450 micron long with an internal hole-diameter of about 45 micron.

Microneedle 340 can be fabricated/constructed from liquid crystal polymers/polyimide/silicon/silk/SU-8 resin/other suitable material.

The MEMS reservoir 300 can be connected to a micro-flow tube 360, which is connected to a micropump 380.

The micropump 380 can be powered by an electrical power providing component 400.

The electrical power providing component 400 can be a printed thin-film battery.

Such a MEMS biomodule 420 can be utilized to achieve a higher permeability (of the bioactive compounds 100 and/or bioactive molecules 100A) through a biological transport medium for long-term programmable/active delivery of the bioactive compounds 100 and/or bioactive molecules 100A.

Alternatively, a MEMS biomodule 420 can be utilized to achieve a higher permeability (of the bioactive compounds 100 and/or bioactive molecules 100A) through a biological transport medium for a long-term programmable/active delivery of the bioactive compounds 100 and/or bioactive molecules 100A, utilizing hydrogels.

The hydrogel embedded with the bioactive compounds 100 and/or bioactive molecules 100A can be utilized in the MEMS reservoirs 300.

The MEMS biomodule 420 can be placed (attached and/or implanted) on or in (meaning within) a human body.

Figure 9A:
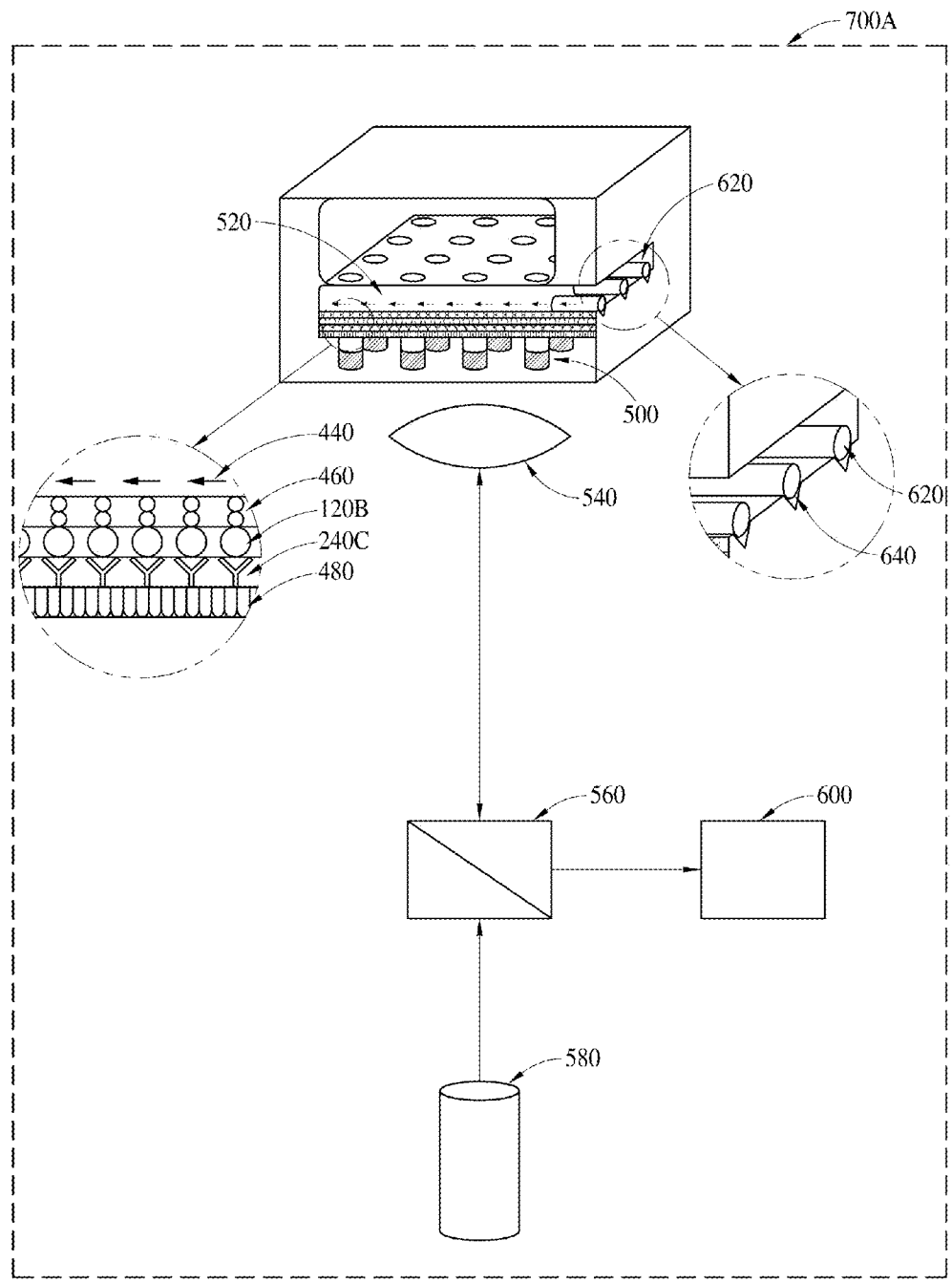
FIGS. 9A, 9B, 9C and 9D illustrate an array of photonic crystal cavities based integrated optical diagnostics biomodule to detect a disease specific biomarker/an array of disease specific biomarkers.

An Array of Photonic Crystal Cavities Based Optical Diagnostics Biomodule for Detection of a Disease Specific Biomarker/an Array of Disease Specific Biomarkers FIG. 9A illustrates an array of photonic crystal cavities 500 based optical diagnostics biomodule 700A for detection of a disease specific biomarker 460 (in a patient's blood 440 which can be propagated through a microfluidic channel 620 to a microfluidic cavity 520).

The disease specific biomarker 460 can chemically bind with a disease specific biomarker binder 240C, wherein the disease specific biomarker binder 240C can chemically bind with a fluorophore 120B on an optional biomolecular interface layer 480, within the array of photonic crystal cavities (fabricated/constructed utilizing both low and high index materials) 500.

An incident light from a MEMS enabled wavelength tunable surface emitting vertical cavity laser 580 can be splitted through an optical beam splitter 560, collimated by a lens 540, absorbed by the fluorophore 120B.

Reference incident emission from the laser 580 and the fluorescence emission wavelength can be measured by a spectrophotometer 600.

By way of an example and not by way of any limitation, the spectrophotometer 600 can be a CCD array/echelle gratings based demultiplexer/microspectrophotometer-on-a-chip/photonic crystal/planar lightwave circuit based demultiplexer/silicon nanowire waveguide based demultiplexer spectrophotometer.

700A can be scaled to an array of disease specific biomarkers 460, an array of disease specific biomarker binders 240C and an array of fluorophores 120B with distinct fluorescence emission wavelengths. A direct correlation exists between the fluorescence emission wavelength and the diameter of a quantum dot fluorophore.

Microspectrophotometer-On-A-Chip

The penetration depth of photons in silicon depends upon wavelength of photons. The shorter wavelength photons can be absorbed in top thin-films, while the longer wavelength photons travel some distance, before they can be absorbed in bottom thin-films.

A pixel of a microspectrophotometer-on-a-chip has vertically stacked detection material thin-film (e.g., silicon) and wavelength tunable optical filters (utilizing a combination of non-absorbing dielectric thin-films and resistor thin-films configured with thermo-optic semiconductor thin-films).

A two-dimensional (2-D) array of the pixels can constitute a microspectrophotometer-on-a-chip.

MEMS Biomodule to Draw/Propagate Blood

Figure 9B:
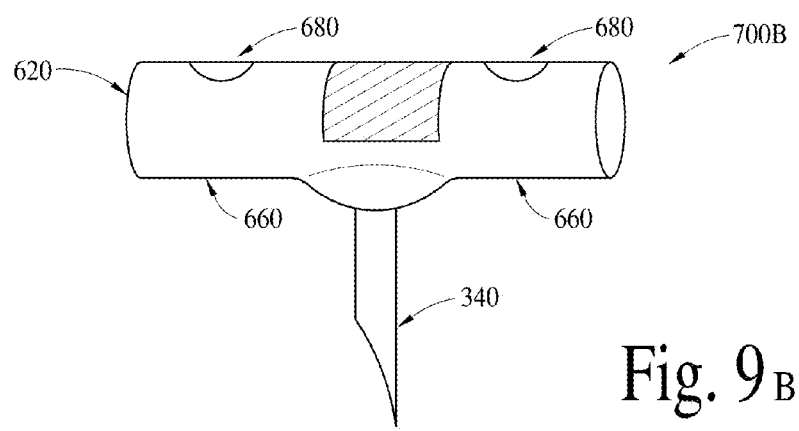

FIG. 9B illustrates a MEMS biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the MEMS biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in FIG. 9B).

The precisely machined connector can be attached precisely/detached from the MEMS biomodule for drawing/propagating the patient's blood.

Figure 9C:
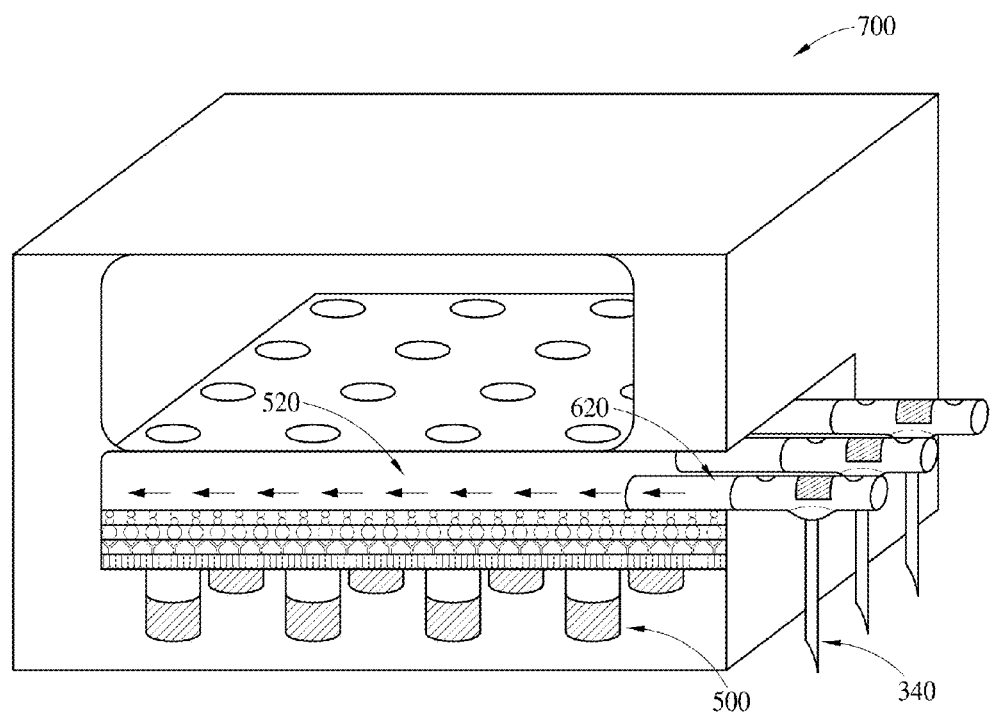

An Array of Photonic Crystal Cavities Based Integrated Optical Diagnostics Biomodule for Detection of a Disease Specific Biomarker/an Array of Disease Specific Biomarkers FIG. 9C illustrates an array of photonic crystal cavities based integrated optical diagnostics biomodule 700.

Stokes Shift to Detect a Disease Specific Biomarker/an Array of Disease Specific Biomarkers The Stokes Shift is the difference between the absorption wavelength and fluorescence emission wavelength.

Figure 9D:
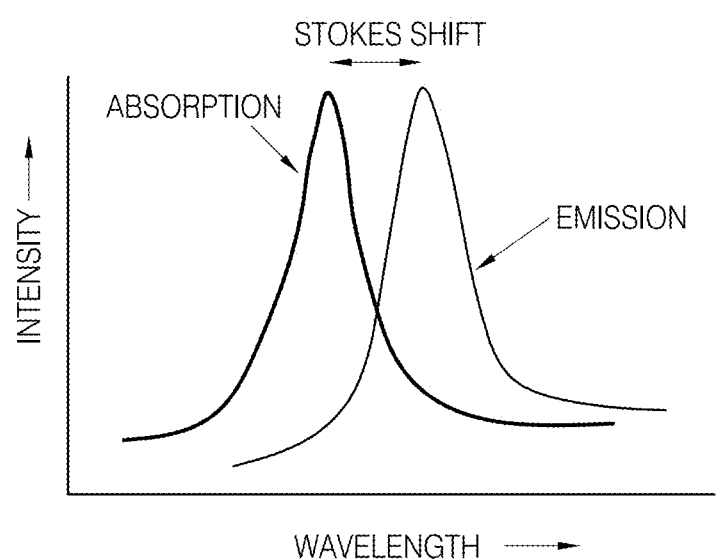

FIG. 9D illustrates the Stokes Shift due to binding of a disease specific biomarker 460 with a disease specific biomarker binder 240C.

The Stokes Shift can be utilized to detect a presence of a disease specific biomarker/an array of disease specific biomarkers.

Figure 10A:
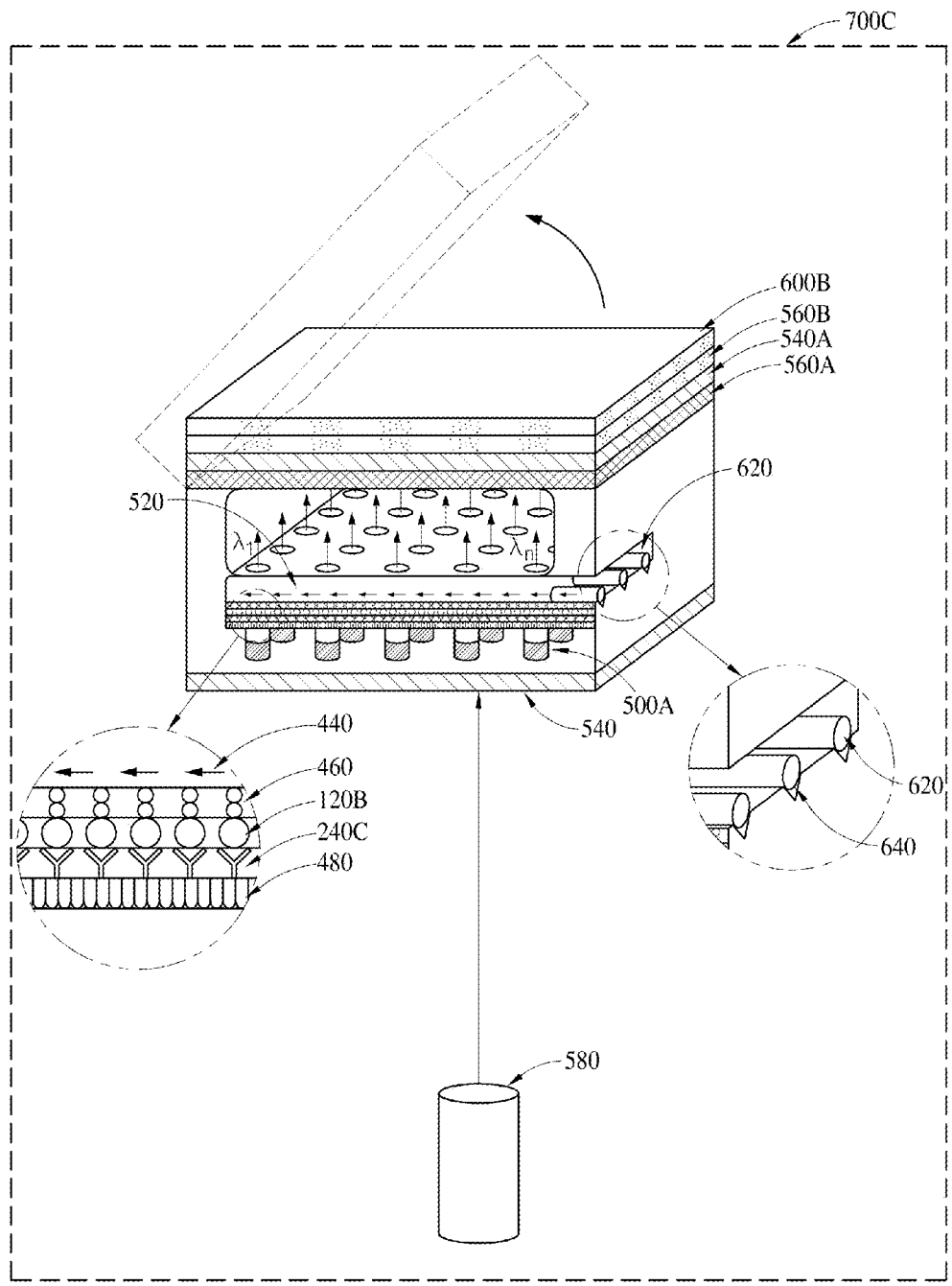
FIGS. 10A, 10B, 10C and 10D illustrate (an array of microcapillaries based) integrated optical diagnostics biomodules (various embodiments) to detect a disease specific biomarker/an array of disease specific biomarkers.

An Array of Microcapillaries Based Optical Diagnostics Biomodule for Detection of A Disease Specific Biomarker/an Array of Disease Specific Biomarkers FIG. 10A illustrates an array of microcapillaries 500A based optical diagnostics biomodule 700C for detection of a disease specific biomarker 460 (in a patient's blood 440, which can be propagated through a microfluidic channel 620 to a microfluidic cavity 520). Furthermore, the array of microcapillaries 500A can be an array of fluidic containers, micro sized fluidic containers/micro sized test tubes/nano sized test tubes.

The disease specific biomarker 460 can chemically bind with a disease specific biomarker binder 240C, wherein the disease specific biomarker binder 240C can chemically bind with a fluorophore 120B, on an optional biomolecular interface layer 480, within the array of microcapillaries 500A.

The array of microcapillaries 500A can be fabricated/constructed, utilizing fused silica/glass/paper/plastic/quartz/other suitable material.

Furthermore, the top optical assembly can be removed to allow a direct access to fill the array of microcapillaries 500A with the patient's blood/biological fluid (e.g., cerebrospinal fluid, saliva, tear and urine).

The array of microcapillaries 500A is optically transparent to the incident light. The incident light from a MEMS enabled wavelength tunable surface emitting vertical cavity laser 580 can be collimated by a lens 540, absorbed by the fluorophore 120B.

A fluorophore 120B can exist within one well of the array of microcapillaries 500A.

700C can be scaled to an array of disease specific biomarkers 460, an array of disease specific biomarker binders 240C and an array of fluorophores 120B with distinct fluorescence emission wavelengths.

Fluorescence emission can propagate through a first optical filter (not to transmit the incident wavelength from the laser 580) 560A, an array of lenses 540A and an array of second optical filters 560B, then finally be detected by an array of light detectors 600B.

By way of an example and not by way of any limitation, the light detector 600B can be a charge-coupled detector (CCD)/intensified charge-coupled detector (ICCD)/color-complementary metal-oxide-semiconductor (CMOS) detector, wherein a CMOS pixel can be integrated with a transparent polyimide light collecting lens and a color (blue, green and red) selective optical filter.

A color selective optical filter can be a wavelength tunable optical filter (utilizing a combination of non-absorbing dielectric thin-films and resistor thin-films configured with thermo-optic semiconductor thin-films).

MEMS Biomodule to Draw/Propagate Blood

Figure 10B:
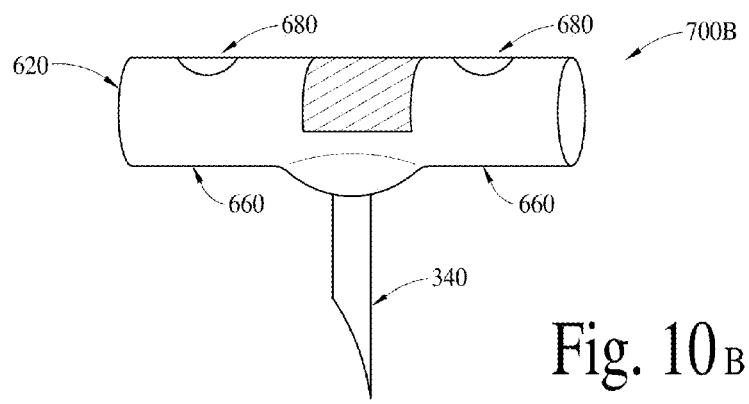

FIG. 10B illustrates a MEMS biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the MEMS biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in FIG. 10B).

The precisely machined connector can be attached precisely/detached from the MEMS biomodule for drawing/propagating the patient's blood.

Figure 10C:
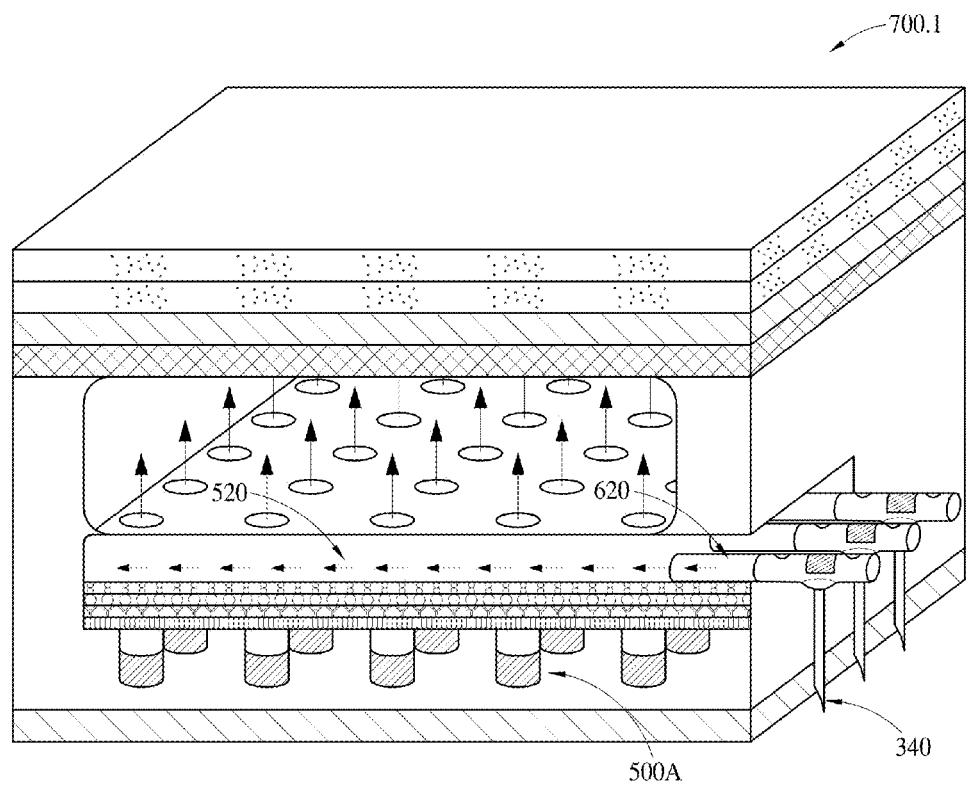

An Array of Microcapillaries Based Optical Integrated Diagnostics Biomodule for Detection of a Disease Specific Biomarker/an Array of Disease Specific Biomarkers FIG. 10C illustrates an array of microcapillaries based integrated optical diagnostics biomodule 700.1

Stokes Shift to Detect a Disease Specific Biomarker/an Array of Disease Specific Biomarkers The Stokes Shift is the difference between the absorption wavelength and fluorescence emission wavelength.

Figure 10D:
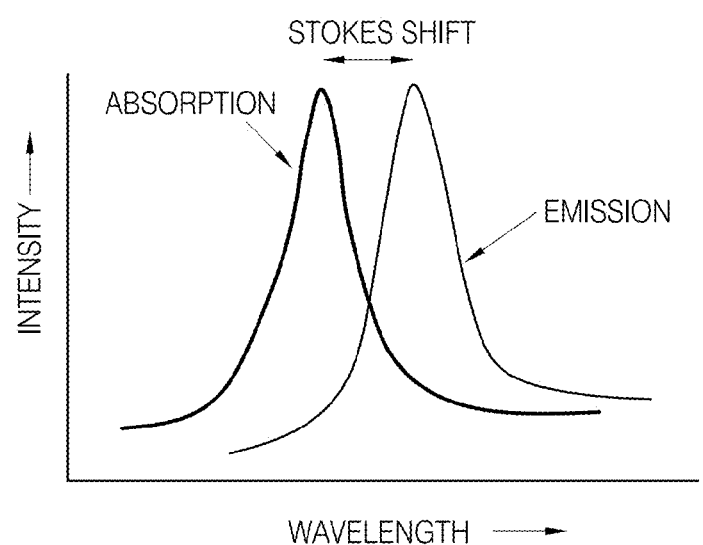

FIG. 10D illustrates the Stokes Shift due to binding of a disease specific biomarker 460 with a disease specific biomarker binder 240C.

The Stokes Shift can be utilized to detect a presence of a disease specific biomarker/an array of disease specific biomarkers.

Figure 11A:
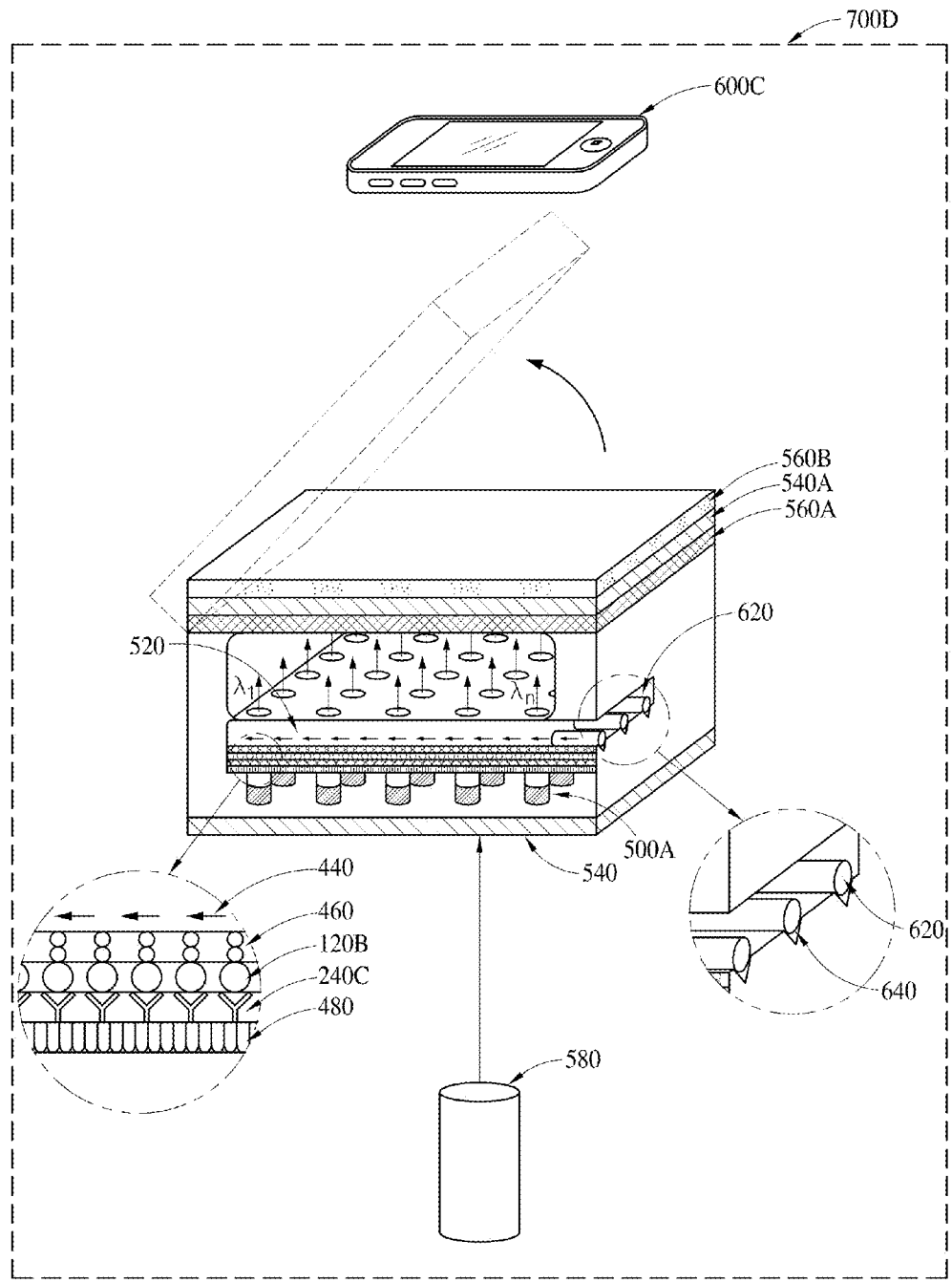
Figure 11:
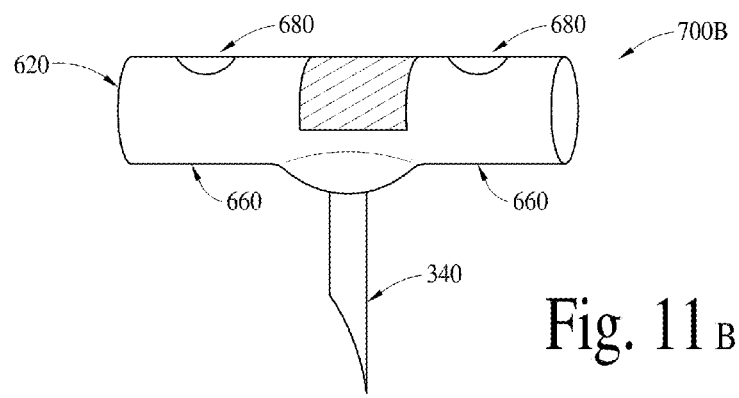
Figure 11:
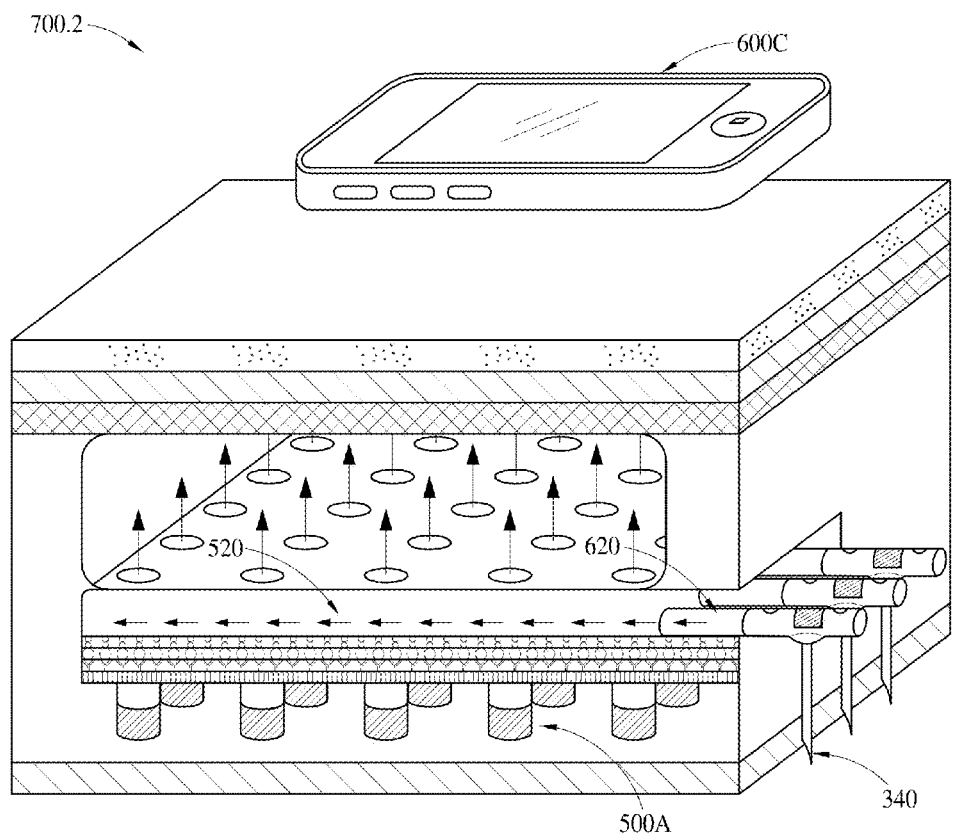

An Array of Microcapillaries Based Optical Diagnostics Biomodule (Configured by A Camera of a Portable Internet Appliance) for Detection of a Disease Specific Biomarker/an Array of Disease Specific Biomarkers FIG. 11A illustrates an array of microcapillaries 500A based optical diagnostics biomodule 700D, configured by a camera (optionally integrated with a color image processing algorithm) 600C of a portable internet appliance. This configuration can replace an array of light detectors 600B.

Furthermore, the top optical assembly can be removed to allow a direct access to fill the array of microcapillaries 500A with the patient's blood/biological fluid (e.g., cerebrospinal fluid, saliva, tear and urine).

700D can be scaled to an array of disease specific biomarkers 460, an array of disease specific biomarker binders 240C and an array of fluorophores 120B with distinct fluorescence emission wavelengths.

Furthermore, the portable internet appliance (as described in U.S. Non-Provisional patent application Ser. No. 12/238, 286 entitled, "PORTABLE INTERNET APPLIANCE", filed on Sep. 25, 2008) can have a profound impact in the healthcare and daily life. The portable internet appliance can communicate with other bio/health sensors to monitor vital health parameters (e.g., blood sugar and heart rate) of a user. For example the portable internet appliance integrated with a QR barcode reader and/or radio frequency identification (RFID) reader and/or near field communication (NFC) reader can access relevant information/website regarding a drug in a container, wherein the container has a QR barcode and/or a passive radio frequency identification (RFID) tag and/or a near field communication (NFC) tag. As the portable internet appliance aware of its location via its embedded GPS module, the portable internet appliance can locate a nearby reputable (statistically ranked by the inputs from other users) pharmacy so that the user's doctor can transmit a secure prescription to the specific pharmacy, the portable internet appliance can order and pay for a transportation service (e.g., a taxi) to reach the specific pharmacy and the portable internet appliance can calculate and advise the transportation service for least-traffic route in order to reach the specific pharmacy quickly. The portable internet appliance can then pay for the prescription drug at the specific pharmacy and later on it can automatically (without any manual input) remind the specific pharmacy for a refill for the prescription drug, when refill is needed.

Furthermore, the portable internet appliance can be integrated with a first set of intelligent learning instructions-such as: artificial intelligence, data mining, fuzzy logic, machine vision, natural language processing, neural networks, pattern recognition, reasoning modeling (including hypothesis based reasoning modeling) and self-learning (including evidence based learning) and a second set of intelligent learning instructions-such as: algorithm-as-a-service, patients' behavior/nutrition modeling, physical search algorithm and software agent.

MEMS Biomodule to Draw/Propagate Blood

FIG. 11B illustrates a MEMS biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the MEMS biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 11B).

The precisely machined connector can be attached precisely/detached from the MEMS biomodule for drawing/propagating the patient's blood.

An Array of Microcapillaries Based Optical Integrated Diagnostics Biomodule (Configured by a Camera of a Portable Internet Appliance) for Detection of a Disease Specific Biomarker/an Array of Disease Specific Biomarkers FIG. 11C illustrates an array of microcapillaries based integrated optical diagnostics biomodule (configured by a camera of a portable internet appliance) 700.2.

Stokes Shift to Detect a Disease Specific Biomarker/an Array of Disease Specific Biomarkers The Stokes Shift is the difference between the absorption wavelength and fluorescence emission wavelength.

Figure 11D:
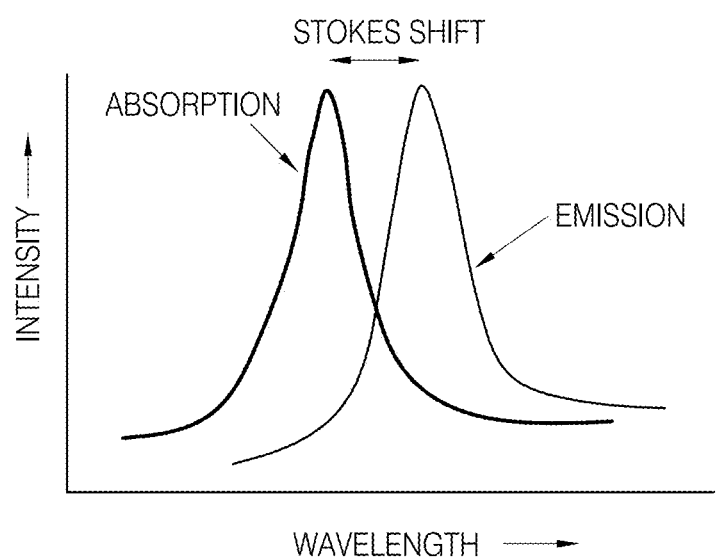

FIG. 11D illustrates the Stokes Shift due to binding of a disease specific biomarker 460 with a disease specific biomarker binder 240C.

The Stokes Shift can be utilized to detect a presence of a disease specific biomarker/an array of disease specific biomarkers.

An Array of Microcapillaries Based Optical Diagnostics Biomodule (Configured by an Array of Optical Fibers & a Nx1 Optical Switch) for Detection of a Disease Specific Biomarker/an Array of Disease Specific Biomarkers FIG. 12A illustrates an array of microcapillaries 500A based optical diagnostics biomodule 700E, configured by an array of optical fibers 620A and a Nx1optical switch 600C.

FIG. 12A illustrates a microcapillary optical diagnostics biomodule 700E for detection of a disease specific biomarker (in a patient's blood 440, which can be propagated through a microfluidic channel 620 to a microfluidic cavity 520).

The disease specific biomarker 460 can chemically bind with a disease specific biomarker binder 240C, wherein the disease specific biomarker binder 240C can chemically bind with a fluorophore 120B, on an optional biomolecular interface layer 480 within the array of microcapillaries 500A.

Furthermore, the top optical assembly can be removed to allow a direct access to fill the array of microcapillaries 500A with the patient's blood/biological fluid (e.g., cerebrospinal fluid, saliva, tear and urine).

The incident light from a MEMS enabled wavelength tunable surface emitting vertical cavity laser 580 can be collimated by a lens 540, absorbed by the fluorophore 120B.

Fluorescence emission can propagate through an array of optical filters (not to transmit the incident wavelength from the laser 580) 560A, an array of focusing lenses 540B and an array of multi-mode/single-mode optical fibers 620A to the Nx1 multi-mode/single mode optical switch 600C and a spectrophotometer 600.

Furthermore, the array of optical fibers 620A can be attached onto an array of precise silicon/ceramic v-grooves 640.

The array of optical fibers 620A can be replaced by an array of optical waveguides (not shown in FIG. 12A).

700E can be scaled to an array of disease specific biomarkers 460, an array of disease specific biomarker binders 240C and an array of fluorophores 120B with distinct fluorescence emission wavelengths.

MEMS Biomodule to Draw/Propagate Blood

FIG. 12B illustrates a MEMS biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the MEMS biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 12B).

The precisely machined connector can be attached precisely/detached from the MEMS biomodule for drawing/propagating the patient's blood.

Light Incident at Side of an Array of Microcapillaries

In FIGS. 10A, 11A and 12A light from the MEMS enabled wavelength tunable surface emitting vertical cavity laser 580 can be incident at the side of the array of microcapillaries 500A.

An Array of Microcapillaries Based Optical Integrated Diagnostics Biomodule (Configured by an Array of Optical Fibers & a Nx1 Optical Switch) for Detection of a Disease Specific Biomarker/an Array of Disease Specific Biomarkers FIG. 12C illustrates an array of microcapillaries based integrated optical diagnostics biomodule 700.3 (configured by an array of optical fibers 620A and a Nx1 optical switch 600C).

Figure 12D:
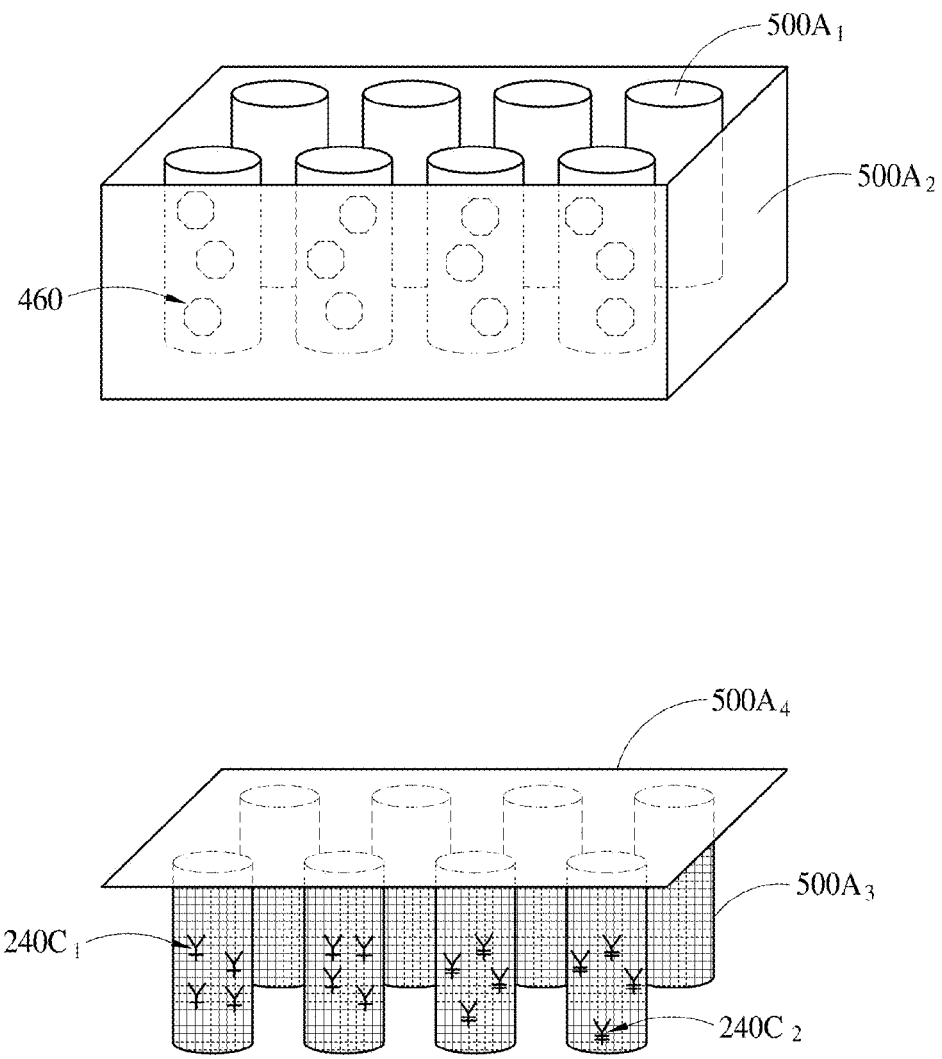

An Array of Microcapillaries Based Optical Integrated Diagnostics Biomodule (Configured by an Array of Optical Fibers, a Nx1 Optical Switch & Multiplexing of Biomarker Binders) for Detection of a Disease Specific Biomarker/an Array of Disease Specific Biomarkers FIG. 12D illustrates an array of microwells $500A_1$, containing blood/biological fluid with an array of disease specific biomarkers 460.

$500A_2$ is an enclosure for the array of microwells $500A_1$. $500A_3$ is an array of micron/nano-sized meshed tubes. $500A_4$ is a removable holder.

The array of micro-meshed/nano-meshed tubes $500A_3$ can contain a biomarker binder assembly $240C_1$ and biomarker binder assembly $240C_2$.

Figure 12E:
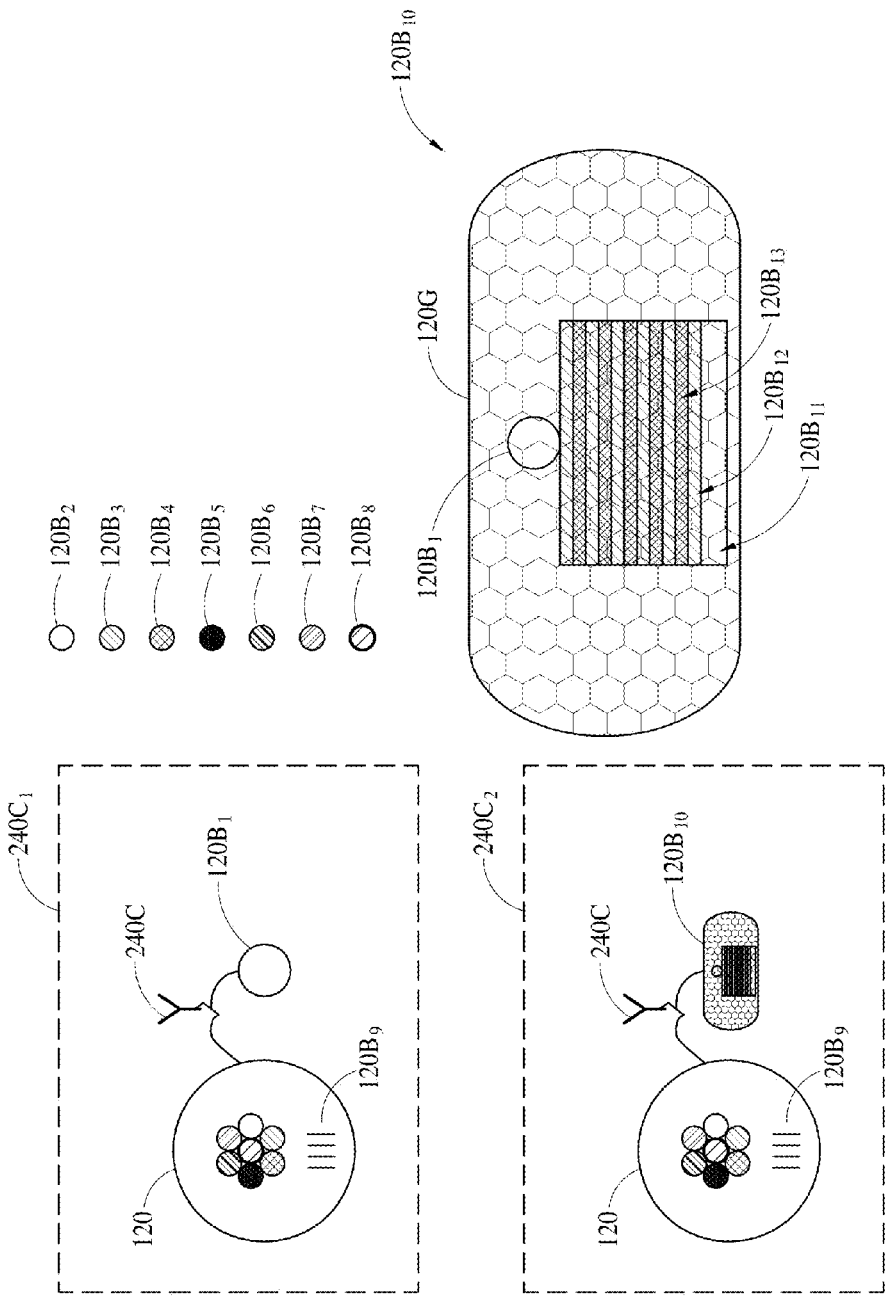

FIG. 12E illustrates the biomarker binder assembly $240C_1$. $240C_1$ can integrate a biomarker binder 240C, a nanoshell 120 and a fluorophore $120B_1$.

The nanoshell 120 can have a printed (by electroplating/laser induced direct printing/soft lithography) metal barcode patterns of alternating reflective gold/silver/nickel/platinum metal $120B_9$ on it.

The stripe width of the metal barcode patterns can be controlled by an amount of current passed during the electroplating process.

The nanoshell 120 can also encapsulate/cage six (6) quantum dot fluorophores $120B_2$, $120B_3$, $120B_4$, $120B_5$, $120B_6$ and $120B_7$, wherein each quantum dot fluorophore has a unique fluorescence color based on the diameter of the quantum dot fluorophore.

Furthermore, intensity of each fluorophore's unique fluorescence emission colors can be varied.

The nanoshell 120 can also encapsulate/cage a paramagnetic nanoparticle (e.g., an iron oxide nanoparticle) $120B_8$.

FIG. 12E also illustrates the biomarker binder assembly $240C_2$. $240C_2$ can integrate a biomarker binder 240C, a nanoshell 120 and a nanotube assembly $120B_{11}$.

The nanotube assembly $120B_{11}$ can consist of a nanotube (e.g., a boron nitride/carbon nanotube or a tubular structure fabricated/constructed by DNA/RNA origami process) 120G. The nanotube 120G can encapsulate/cage at least one quantum dot fluorophore $120B_1$ on alternating thin-films of titanium dioxide dielectric (about 15-30 nm in thickness) $120B_{12}$ and metal silver $120B_{13}$ (about 5-10 nm in thickness) on a biochemically functional glass/plastic substrate $120B_{11}$.

FIG. 12F illustrates the biomarker binder assembly $240C_1$, chemically bonded with a biomarker 460 and an entire biomarker binder assembly-biomarker combination is represented as 460A.

FIG. 12F illustrates the biomarker binder assembly $240C_2$, chemically bonded with a biomarker 460 and an entire biomarker binder assembly-biomarker combination is represented as 460B.

FIG. 12G illustrates an optical diagnostics biomodule 700.4 to determine fluorescence of 460A and 460B upon magnetically pulled down by an optically transparent magnetic substrate $120B_{14}$ and then excited by an array of MEMS enabled wavelength tunable surface emitting vertical cavity lasers 580 and collimated by an array of lenses 540.

An assembly 640A integrates suitable optical filters, suitable lenses and two (2) optical fibers 620A on precise silicon/ceramic v-grooves.

At one instance utilizing wavelength $\lambda=\lambda_1$ from the MEMS enabled wavelength tunable surface emitting vertical cavity lasers 580, transmission of wavelength $\lambda=\lambda_1$ through a metal barcode pattern, further propagated through a suitable optical filter, suitable lens and optical fiber 620A is then multiplexed by the Nx1 multi-mode/single optical switch 600C and analyzed by the spectrophotometer 600.

Any suitable image processing software can be utilized to resolve any mis-orientated metal barcode pattern.

At another instance, utilizing wavelength $\lambda=\lambda_2$ from the MEMS enabled wavelength tunable surface emitting vertical cavity lasers 580, a fluorescence spectrum of the entire biomarker binder assembly-biomarker combination 460A/460B, is propagated through a suitable optical filter, suitable lens and optical fiber 620A, then multiplexed by the Nx1 multi-mode/single optical switch 600C and analyzed by the spectrophotometer 600.

The array of optical fibers 620A can be replaced by an array of optical waveguides (not shown in FIG. 12G).

Furthermore, an array of optical waveguides and lenses can be integrated (by a monolithic and/or hybrid process) on silica on silicon substrate.

One million optical barcodes can be realized utilizing six (6) unique fluorescent emission colors and ten (10) intensity levels for each unique fluorescent emission color.

Furthermore, one million optical barcodes can be also enhanced in conjunction with reflective metal barcode patterns.

Up to 2 million or more disease specific biomarkers 460 per microwells $500A_1$ can be identified utilizing a combination of optical barcode multiplexing and metal barcode multiplexing.

Enhancement of Fluorescent Signal

Light is a wave. Thus an optical antenna can amplify light wave in the same way as a television and/or mobile phone captures radio waves.

Two gold particles (about 40 nm diameter) and a fluorophore (e.g., a quantum dot fluorophore) bonded to a synthetic DNA strand (about 15 nm long) can act as an optical antenna.

The fluorophore can act as a quantum source, supplying the antenna with photons.

Generation of Raman Signal

In FIGS. 12A and 12G, the function of the disease specific biomarker binder 240C can be enhanced by a dielectric (e.g., silica) sphere (about 50 nm in diameter).

The dielectric sphere can be encapsulated/caged in a thin metal (e.g., gold), wherein the thin metal is coupled with the biomarker binder (e.g., an aptamer) 240C to bind with the disease specific biomarker 460.

When light from the MEMS enabled wavelength tunable surface emitting vertical cavity laser 580 is incident on the above silica sphere, it can shift a characteristic Raman signal (Raman Shift) upon chemically binding with the disease specific biomarker 460.

Measurement of Raman Shift

Measurements of Raman Shift can require a high-performance laser module. But a Raman sensor can utilize the MEMS enabled wavelength tunable surface emitting vertical cavity laser 580 to scan over a narrow band of Raman Shift via a suitable wavelength tunable optical filter.

Surface-Enhanced Raman Scattering/Spectroscopy (SERS) Surface-Enhanced Resonance Raman Scattering/Spectroscopy (SERRS)

If bottom of the micro-meshed tubes 500$A_3$ (FIG. 12D) is atomically rough, then the disease specific biomarker 240C can be identified by surface-enhanced Raman scattering/spectroscopy (SERS) or alternatively by surface-enhanced Resonance Raman scattering/spectroscopy (SERRS)

Electron-beam lithographically patterned and ion beam etched (about) 25 nm pitch surface gratings of metal thin-film (about 2 to 5 nm in thickness deposited by a low-temperature atomic layer deposition (ALD) process) on porous silicon substrate can be utilized as a reproducible atomically rough surface.

Surface-enhanced Raman scattering/spectroscopy (SERS) is a surface-sensitive analytical technique that can enhance Raman scattering by a factor of $10^{10}$.

One disadvantage of SERS is spectral interpretation. The signal enhancement is so dramatic that even weak Raman bands (unnoticeable in conventional Raman scattering/spectroscopy) can appear in SERS.

Some trace contaminants can contribute unwanted peaks in SERS. Furthermore, chemical interactions with metal surfaces, certain strong peaks (noticeable in conventional Raman scattering/spectroscopy) might not appear in SERS.

Because of above complications in SERS, SERRS can integrate both the surface-enhancement and the Raman resonance—thus the Raman signal intensity can be as high as $10^{14}$ and Raman spectra can be easier to interpret.

Addition of Nanostructures to Enhance Fluorescence Signal or Raman Signal from an Array of Microcapillaries To enhance the fluorescence signal or Raman signal from the array of microcapillaries 500A, a two-dimensional (2-D) array of nanometer sized linear gratings can be fabricated/constructed/bonded at the bottom of each microcapillary of the array of microcapillaries 500A.

To enhance the fluorescence signal or Raman signal from the array of microcapillaries 500A, alternatively a two-dimensional (2-D) array of nanometer sized curved gratings can be fabricated/constructed/bonded at the bottom of each microcapillary of the array of microcapillaries 500A.

To enhance the fluorescence signal or Raman signal from the array of microcapillaries 500A, alternatively a two-dimensional (2-D) array of nanometer sized photonic crystal gratings can be fabricated/constructed/bonded at the bottom of each microcapillary of the array of microcapillaries 500A.

To enhance the fluorescence signal or Raman signal from the array of microcapillaries 500A, alternatively a two-dimensional (2-D) array of nanometer sized three-dimensional (3-D) structures can be fabricated/constructed/bonded at the bottom of each microcapillary of the array of microcapillaries 500A.

The shape, diameter, height and pitch of the three-dimensional (3-D) structures can be varied for maximum enhancement of the fluorescence or Raman emission.

Furthermore, the above linear gratings, curved gratings, photonic crystal gratings and three-dimensional (3-D) structures can be decorated with a thin-film metal (e.g., gold/silver).

By Way of an Example and not by Way of any Limitation, an Exosome as a Disease Specific Biomarker A disease specific biomarker 460 can indicate a progression of a disease. Exosome (40 nm-100 nm in diameter) and microvesicle (100 nm-1000 nm in diameter) are small vesicles that are shed by cells.

Exosome and microvesicle carry messenger RNAs, micro-RNAs and signaling proteins.

The circulating level, origination and message transported by exosome and/or microvesicle can be utilized as a disease specific biomarker 460.

Furthermore, exosome and/or microvesicle as a disease specific biomarker can be selectively qualified and/or quantified by a disease specific biomarker binder, wherein the disease specific biomarker binder is coupled with a fluorophore.

By Way of an Example and not by Way of any Limitation, an Antibody or Aptamer or Molecular Beacon as a Disease Specific Biomarker Binder A disease specific biomarker binder 240C can be an antibody/aptamer/molecular beacon.

Furthermore, an aptamer can be a (fluorescence) wavelength-shifting aptamer, wherein upon binding a (fluorescence) wavelength-shifting aptamer switches fluorescence wavelength from one wavelength to another wavelength. Thus a (fluorescence) wavelength-shifting aptamer can reduce background signal in the biological fluid.

A molecular beacon is looped like a hairpin. The loop like hairpin can contain a molecular probe sequence, which is complementary to a disease specific nucleic acid molecule. The molecular beacon can be chemically coupled with a fluorophore at one end and a non-fluorescent quencher at the other end.

Furthermore, in addition to molecular quenchers, many nanomaterials (e.g., graphene oxide (GO)) also possess excellent quenching efficiency.

Upon binding to the disease specific nucleic acid molecule, the molecular probe sequence undergoes a spontaneous conformational reorganization, which removes the fluorophore from the vicinity of the quencher and restores its fluorescence.

Optionally, the molecular beacon can be chemically coupled with two (2) or more quantum dot fluorophores, assembled/fabricated/constructed by a tip of an atomic force microscope (AFM).

Furthermore, the molecular beacons chemically coupled with fluorophores (each fluorophore has a distinct fluorescence emission) can be utilized as an array of disease specific biomarkers.

An Electrical Diagnostics Biomodule for Detection of a Disease Specific Biomarker/an Array of Disease Specific Biomarkers Graphene is a two-dimensional (2-D) crystal with a high carrier mobility and low noise. It has the ideal properties to be an excellent component of electrical circuits. Graphene epitaxially grown on silicon carbide (SiC) substrate can be suitable for production of electrical circuits.

Graphene variant called graphane, wherein hydrogen atoms are attached to the carbon lattice in insulating layers.

Graphyne is one-atom-thick sheet of carbon that resembles graphene, except in its two-dimensional (2-D) framework (of atomic bonds) contains triple bonds in addition of double bonds.

Graphyne has a graphene-like electronic structure resulting in effectively massless electrons due to Dirac Cones. All electrons are travelling at roughly the same speed (about 0.3 percent of the speed of light). This uniformity leads to conductivity greater than copper.

Graphyne can be utilized as a semiconductor practically as-is, rather than requiring noncarbon dopant atoms to be added as a source of electrons, as noncarbon dopants are required for graphene. Furthermore, structures of graphyne crystal allow electrons to flow in one direction.

Molybdenite ($MoS_2$) is also a two-dimensional (2-D) crystal with a natural bandgap. It can be suitable for production of electrical circuits.

FIG. 13A illustrates an electrical diagnostics biomodule 840A based on change in electrical characteristics of a two-dimensional (2-D) crystal based field effect transistor (FET) (e.g., graphene or molybdenite) due to a disease specific biomarker 460 (in a patient's blood 440) which can be propagated through a microfluidic channel 620 to a microfluidic cavity 520).

The disease specific biomarker 460 can chemically bind with a disease specific biomarker binder 240C on the optional biomolecular interface layer 480 on a single layer of the two-dimensional (2-D) crystal substrate 820.

The field-effect transistor (FET) can integrate: a semiconductor substrate as a gate 720, a gate oxide insulator thin-film 740, a source metal thin-film 760, a drain metal thin-film 780, a polymeric insulator thin-film 800 and the single layer of the two-dimensional (2-D) crystal substrate 820.

MEMS Biomodule to Draw/Propagate Blood

FIG. 13B illustrates a MEMS biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the MEMS biomodule 700B can include an array of microneedles 340, an array of micromachined membranes 660, an array of membrane sensors 680 and an array of microfluidic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 13B).

The precisely machined connector can be attached precisely/detached from the MEMS biomodule for drawing/propagating the patient's blood.

An Integrated Two-Dimensional (2-D) Crystal Field-Effect Transistor (FET) Based Electrical Diagnostics Module for Detection of a Disease Specific Biomarker/an Array of Disease Specific Biomarkers FIG. 13C illustrates an integrated two-dimensional (2-D) crystal field-effect transistor (FET) based electrical diagnostics biomodule 840.

Engineered Protein Based Field-Effect Transistor (FET) to Replace Two-Dimensional (2-D) Crystal Field-Effect Transistor (FET)

Furthermore, the two-dimensional (2-D) crystal field-effect transistor (FET) can be replaced by an engineered protein based field-effect transistor (FET).

The engineered protein based field-effect transistor (FET) can be fabricated/constructed utilizing a suitable material decorated on engineered protein (e.g., a 3-D ball and spike engineered protein-synthesized by a fusion of both Dps and gp5c genes).

Proton Based Field-Effect Transistor ($H^+FET$) Decorated with a Lipid Layer to Replace Two-Dimensional (2-D) Crystal Field-Effect Transistor (FET)

FIG. 13D illustrates a natural biopolymer chitosan/melanin based proton field-effect transistor ($H^+FET$) 820E and it incorporates a semiconductor substrate as a gate 720, a gate oxide insulator thin-film 740, a source metal thin-film 760 and a drain metal thin-film 780 for proton current.

Furthermore, palladium hydride contacts can replace a traditional source metal thin-film 760 and/or a drain metal thin-film 780.

Furthermore, proton field-effect transistor ($H^+FET$) 820E can be decorated with a lipid layer (a double wall of oil molecules, that biological cell utilizes to separate its inside from its outside environment) 820G.

The lipid layer 820G can be decorated with a disease specific biomarker binder 240C.

The disease specific biomarker binder 240C can chemically bind with a disease specific biomarker 460—thus it can change the electrical characteristics of the proton field-effect transistor ($H^+FET$) 820E.

Furthermore, the proton field-effect transistor ($H^+FET$) 820E can be integrated with a nanotube (e.g., a boron nitride/carbon/tubular structure nanotube, fabricated/constructed by DNA/RNA origami process) 120G based nanoradio transmitter with a nanoantenna 900A.

The nanotube 120G based nanoradio transmitter with the nanoantenna 900A can be electrically powered by a nanobattery 400A.

A miniaturized non-rechargeable lithium battery can replace the nanobattery 400A.

Glucose fuel cell (fabricated/constructed on a silicon substrate with integrated platinum catalyst to strip electrons from glucose) can replace the nanobattery 400A.

M13 bacteriophage can translate mechanical energy into electrical energy.

To improve the piezoelectric property of M13 bacteriophage, the outer protein layer of M13 bacteriophage can be engineered by adding appropriate molecules.

Furthermore, to amplify piezoelectric effect, multi-layers of engineered M13 bacteriophage can be utilized.

Multi-layers of engineered M13 bacteriophage can then be sandwiched between two biocompatible electrodes to act as a battery, when stressed mechanically (e.g., by a cardiac cycle).

Similarly, prestin protein can convert tiny vibrations into a voltage output. Each prestin protein is only capable of making nanowatts of electricity. Many prestin proteins can be sandwiched between two biocompatible electrodes to act as a battery, when stressed mechanically (e.g., by a cardiac cycle).

Furthermore, in melanin based electrical circuits both electron and proton can be utilized. Chitosan/melanin based proton field-effect transistor ($H^+$ FET) 820E integrated with the nanoradio transmitter with a nanoantenna 900A and the nanobattery 400A can be indicated as 840C.

Silicon Nanowire Based Field-Effect Transistor (Si-Nano FET) Decorated with a Lipid Layer to Replace Two-Dimensional (2-D) Crystal Field-Effect Transistor (FET)

FIG. 13E illustrates a similar configuration as 13D except a silicon nanowire to replace chitosan/melanin.

Silicon nanowire field-effect transistor (FET) 820F integrated with the nanotube 120G based nanoradio transmitter, the nanoantenna 900A and the nanobattery 400A can be indicated as 840D.

Furthermore, the silicon substrate of silicon nanowire field-effect transistor (FET) 820F can also be replaced by melanin.

Furthermore, a conducting polymer nanowire can replace a silicon nanowire.

A nanoantenna printed on a biocompatible material (e.g., silk) can be placed in (within) a human body such that any change in current flow in the nanoantenna can induce a change in the radio transmitter placed on a human body.

An Interface Electrode

Boron-doped conducting diamond like material can be grown on a silicon dioxide ($SiO_2$) substrate by chemical vapor deposition at about 900 degree centigrade.

Boron-doped conducting diamond like material can be bonded on a polymer substrate and then lifted off from the silicon dioxide ($SiO_2$) substrate by hydrofluoric (HF) acid.

Thus a boron-doped conducting diamond like material can act as an interface electrode for any biological application.

Detection of a Disease Specific Biomarker/an Array of Disease Specific Biomarkers & Programmable/Active Delivery of Bioactive Compounds/Bioactive Molecules in Near Real-Time/Real-Time If 840C/840D detects an abnormal level of a disease specific biomarker 460, then the nanoradio transmitter with the nanoantenna 900A can transmit the information such that a MEMS reservoir to enable a programmable/active delivery of the bioactive compounds 100 and/or bioactive molecules 100A in near real-time/real-time via a dynamic closed feedback loop.

Furthermore, an array of 840C/840D can be utilized instead of a single 840C/840D.

Nanohole Based Diagnostics Biomodule for Detection of a Disease Specific Biomarker/an Array of Disease Specific Biomarkers Four (4) molecules, when chemically bonded together, make up the structural units of a DNA are: adenine (A), cytosine (C), guanine (G) and thymine (T). A segment of a DNA strand can be a gene.

Four (4) molecules, when chemically bonded together, make up the structural units of an RNA are: adenine (A), cytosine (C), guanine (G) and uracil (U).

FIG. 14A illustrates a nanotunnel 500C. The nanotunnel 500C can be fabricated/constructed by atomic layer deposition (ALD) on an atomically thick substrate.

Multi-layers of dielectrics 740B and metals 760B are embedded in the nanotunnel 500C.

A nanohole 500D is about 1 nm in diameter. The nanohole 500D can be fabricated/constructed just below the nanotunnel 500C.

Alternatively, the nanohole 500D can also be fabricated/constructed by DNA/RNA origami process on the same atomically thick substrate.

The nanohole 500D has four (4) embedded tunneling metal electrodes 820A.

The four (4) embedded tunneling electrodes 820A are metal (e.g., gold) nanoparticle based tunneling electrodes.

The four (4) embedded tunneling metal electrodes 820A can be fabricated/constructed by DNA/RNA origami process.

DNA origami process is a template for the design and fabrication of nanoscale structures. One can engineer selected staple strands on a DNA origami structure with site-specific attachment of gold nanoparticles to fabricate conducting nanowires from DNA origami nanostructure.

Similarly, RNA origami template can replace DNA origami template.

FIG. 14B illustrates a set of two (2) embedded tunneling metal electrodes 820A diametrically positioned as opposite to each other.

FIG. 14B also illustrates another set of two (2) embedded tunneling metal electrodes 820A diametrically positioned as opposite to each other.

The nanohole 500D can be mechanically supported on a larger (about 5 nm in diameter) nanohole in an atomically thick dielectric 740C.

The dielectric 740C can be fabricated/constructed by a low-temperature atomic layer deposition (ALD) process.

The larger (about 5 nm in diameter) nanohole in the dielectric 740C can be fabricated/constructed by electron beam lithography and ion beam etching.

Furthermore, the larger nanohole (about 5 nm in diameter) in the dielectric 740C can be mechanically supported on a relatively larger diameter (about 10 nm in diameter) fabricated/constructed in an atomically thick two-dimensional (2-D) crystal (e.g., graphene) membrane 820.

The nanohole 500D can be electrically connected to the atomically thick membrane of two-dimensional (2-D) crystal 820 for reliable electrical contacts.

A single stranded DNA/RNA 820D can be pulled down through the nanotunnel 500C and nanohole 500D by a vertical electrical field, as a DNA/RNA 820D is electrically charged.

A four-point-probe measurement of transverse tunneling currents (of about 3A° long single molecule of the single stranded DNA/RNA 820D) through the nanotunnel 500C and nanohole 500D can electrically identify each single molecule of the single stranded DNA/RNA 820D.

Tunneling is confined to tiny distances such that a tunnel junction can identify about 3A° long single molecule of the single stranded DNA/RNA 820D at a time without interference from other molecules.

But because of this extreme sensitivity required in measurement of transverse tunneling currents, tiny vibrations can severely degrade a tunneling signal.

Large electric field is needed to push single stranded DNA/RNA 820D through the nanohole 500D, but the same large electric field can also push single stranded DNA/RNA 820D too rapidly through the nanohole 500D, thus reducing four embedded tunneling metal electrodes 820A' ability to sense/read individual molecule in single stranded DNA/RNA, utilizing the four-point-probe measurement of transverse tunneling currents.

However, the pulling speed of the single stranded DNA/RNA 820D can be reduced by traversing the single stranded DNA/RNA 820D through an alternating electric field generated by multi-layers of dielectrics 740B and metals 760B, embedding/surrounding the nanotunnel 500C.

Furthermore, single stranded DNA/RNA can be chemically coupled to a magnetic nanoparticle to push single stranded DNA/RNA by a magnetic field in the opposite upward direction with respect to the downward electric field.

The tug-of-war between the electric field and the magnetic field (oppositely orientated with respect to each other)

can be optimized to reduce the velocity of single stranded DNA/RNA—thus allowing four embedded tunneling metal electrodes 820A' ability to sense/read individual molecule in single stranded DNA/RNA, utilizing the four-point-probe measurement of transverse tunneling currents.

A molecule can either be right handed (D) or left handed (L). This property is called chirality. A chiral molecule can recognize/transfer information that have the same chirality (same handedness, L to L or D to D) and discriminate the molecule of different chirality (L to D and D to L).

Furthermore, diametrically opposite first set of two (2) embedded tunneling electrodes 820A, wherein each embedded tunneling electrode is chemically configured with a recognition molecule 820B such that, the recognition molecule 820B for adenine (A) can effectively clutch adenine (A) of the single stranded DNA/RNA 820D.

Furthermore, diametrically opposite second set of two (2) embedded tunneling electrodes 820A, wherein each embedded tunneling electrode is chemically configured with a recognition molecule 820C such that, the recognition molecule 820C for guanine (G) can effectively clutch guanine (G) of the single stranded DNA/RNA 820D.

Furthermore, it may not be necessary to uniquely identify all four (4) molecules for some applications. A binary conversion of molecular sequence (e.g., A or T=0, and G or C/U=1) can be utilized to identify a disease specific biomarker and/disease specific genomic alteration/elimination in the single stranded DNA/RNA 820D.

Furthermore, statistics enhanced repeated four-point-probe measurements of transverse tunneling currents can reliably identify each single molecule of the single stranded DNA/RNA 820D—thus detecting an alteration/elimination of a single molecule of the single stranded DNA/RNA 820D, without a need of PCR and Sanger sequencing.

Furthermore, such a two dimensional (2-D) array of the nanotunnels 500C and the nanoholes 500D can sequence many single stranded DNA/RNA 820D in parallel.

The nanohole based diagnostics biomodule (including the two dimensional (2-D) array of the nanotunnels 500C and the nanoholes 500D) for detection of a disease specific biomarker/an array of disease specific biomarkers is identified as 840.1.

Bioelectronics Subsystem for Detection of a Disease Specific Biomarker/an Array of Disease Specific Biomarkers & Programmable/Active Delivery of Bioactive Compounds &/or Bioactive Molecules in Near Real-Time/Real-Time FIG. 15A illustrates an integrated bioelectronics subsystem 960 for detection of a disease specific biomarker/an array of disease specific biomarkers and programmable/active delivery of bioactive compounds 100 and/or bioactive molecules 100A in near real-time/real-time.

The integrated bioelectronics subsystem 960 at least includes (a) a MEMS biomodule 420/420.1, (b) an integrated optical diagnostics biomodule 700.1/700.2/700.3/700.4 (c) an integrated electrical diagnostics biomodule 840/840.1 and (d) an electronic module 940.

Furthermore, the electronics module 940 can be fabricated/constructed on a flexible/bendable/stretchable substrate by lifting off the electronics circuit layer from a rigid semiconductor substrate and then bonding/connecting the lifted off electronics layer on nanoribbons of wires mounted onto a lightweight and stretchable membrane, wherein the wires can bend, twist and stretch, while maintaining their functionality.

The integrated bioelectronics subsystem 960 can stick to the biological transport medium via the van der waals force, without the need of an adhesive.

Thus the integrated bioelectronics subsystem 960 can be removed easily from the biological transport medium.

The electronics module 940 can integrate: (a) an electrical power providing component 400, (b) a microprocessor component 860, (c) a memory/data storage component 880, (d) a wireless (radio) transceiver component 900 and (e) an embedded operating algorithm 920.

By way of an example and not by way of any limitation, the wireless (radio) transceiver component 900 can be configured with Wibree/Bluetooth/near field communication/WiFi.

Other bio/health sensors to monitor vital health parameters (e.g., blood sugar and heart rate) can be integrated with the electronics module 940 to monitor vital health parameters (e.g., blood sugar and heart rate).

Silicon on Insulator as an Integration Platform Substrate for the Integrated Bioelectronics Subsystem 960

For fabricating/constructing a compact bioelectronics subsystem 960 optical components/electronics circuitry components can be attached (including flip-chip bonding on metallized thermal bumps integrated with thin-film solder) on silicon on insulator (SOI) as an integration platform substrate.

Printed Electronics Over a Three-Dimensional (3-D) Structure for Miniaturization/Manufacturing of the Integrated Bioelectronics Subsystem 960

Aerosol Jet can atomize nanoparticle based print materials into microscopic droplets. These microscopic droplets can be focused utilizing a sheath of gas into a precise jet stream by a nozzle.

The nozzle can be placed about 5 mm away from a surface/irregular shaped surface.

Both the nozzle and a container securing the surface/irregular shaped surface can be manipulated through different angles to print (size smaller than 0.01 mm wide) on a three-dimensional (3-D) structure.

Higher level of miniaturization and manufacturing can be realized, utilizing printed electronics (e.g., aerosol nanoparticle Jet to print an antenna, electronics circuitry, radio frequency component and sensor).

Furthermore, printed electronics can print a section of the integrated bioelectronics subsystem 960 over a three-dimensional (3-D) structure, instead of assembling many discrete components.

However, printed electronics can be extended to any substrate of any material of any shape.

For example, resting arms of a wheel chair can be printed with various bio/health sensors to monitor vital health parameters (e.g., blood pressure, blood sugar, heart rate, % oxygen in blood and weight) and low-power wireless sensors (e.g., Bluetooth/Wibree/near field communication/WiFi) to transmit such vital health parameters to a portable internet appliance for statistical analysis, then eventually to a health care professional.

Furthermore, DuPont Kevlar and carbon fiber can be utilized to reduce the weight of the wheel chair.

Alternatively, fiber-reinforced composite (thermoplastic composite) can be utilized to reduce the weight of the wheel chair.

The integrated bioelectronics subsystem 960 can communicate with an integrated intelligent expert algorithm (utilizing an artificial intelligence algorithm and/or a neural network algorithm and/or a fuzzy logic algorithm) of diseases/treatments (the integrated intelligent expert algorithm can be located at a cloud server).

Furthermore, the intelligent expert algorithm can be complimented by a collection of inputs (including identification of images) from healthcare professionals. The inputs from the healthcare professionals can be in near real-time/real-time. These inputs can complement/enhance the intelligent expert algorithm.

Furthermore, the integrated intelligent expert algorithm can include: statistical analysis (e.g., Student t-test, ANOVA (analysis of variance) and Chi-Square), data mining analysis (e.g., ANN (artificial neural network), hierarchical cluster analysis and KNN (K-nearest neighbor analysis) and performance analysis (e.g., specificity, sensitivity and accuracy).

Furthermore, the integrated intelligent expert algorithm can be enhanced by a first set of intelligent learning instructions-such as: artificial intelligence, data mining, fuzzy logic, machine vision, natural language processing, neural networks, pattern recognition, reasoning modeling (including hypothesis based reasoning modeling) and self-learning (including evidence based learning) and a second set of intelligent learning instructions-such as: algorithm-as-a-service, patients' behavior/nutrition modeling, physical search algorithm and software agent.

FIG. 15B illustrates a near real-time/real-time application of a wearable integrated bioelectronics subsystem of 960.

The above bioelectronics subsystem 960 can enable a near real-time/real-time measurement of a disease specific biomarker and instantaneous programmable/active delivery of the bioactive compounds 100 and/or bioactive molecules 100A in near real-time/real-time (via a dynamic closed feedback loop).

The above bioelectronics subsystem 960 can enable a near real-time/real-time measurement of a disease specific biomarker and delayed programmable/active delivery of the bioactive compounds 100 and/or bioactive molecules 100A in near real-time/real-time (via a dynamic closed feedback loop) utilizing a remote wireless command from a healthcare professional.

X-Ray Fluorescence Diagnostics Biomodule Utilizing an Array of Microcapillaries & an Array of Miniature X-Ray Sources An array of microcapillaries containing a biological sample can be excited by an array of miniature x-ray sources (powered by a portable electrical power providing component) to induce x-ray fluorescence in the biological sample for various elemental concentrations related to a disease.

Furthermore, multiple DNA and/or protein biomarkers can be detected based on characteristic x-ray fluorescence.

The array of sharp tips of a pyroelectric crystal (e.g., lithium niobate/lithium tantalite can be fabricated/constructed on a thin-film resistor. The array of sharp tips can be capped with a metal thin-film. The metal thin-film emits x-rays when bombarded by electrons emitted by the sharp tips.

The x-ray fluorescence can be detected by an array of silicon drift detectors. Due to the unique process/fabrication technology of the silicon drift detectors, the leakage current of the silicon drift detectors is low such that the silicon drift detectors can be operated with a moderate cooling, provided by a single stage thermoelectric cooler (TEC)/microrefrigerator.

Furthermore, a high-efficiency nanostructure 50 A° thick $Sb_2Te_3$/10 A° thick $Bi_2Te_3$ based thin-film super-lattices miniature thermoelectric cooler (TEC)/microrefrigerator (about 1 mm×3 mm in size) can be utilized to cool the array of silicon drift detectors.

However, significant thermoelectric cooler (TEC)/microrefrigerator efficiency can be gained by fabricating a quantum wire/quantum dot, transitioning from a two-dimensional (2-D) super-lattice.

Retinal Contact Lens Biomodule Subsystem for Detection of a Disease Specific Biomarker/an Array of Disease Specific Biomarkers & Programmable/Active Delivery of Bioactive Compounds &/or Bioactive Molecules in Near Real-Time/Real-Time Specific proteins (e.g., a protein biomarker of Alzheimer disease) can accumulate in retina. These specific proteins can be utilized to diagnose a disease specific biomarkers/an array of disease specific biomarkers in near real-time/real-time.

FIG. 16A illustrates a retinal contact lens biomodule subsystem 1180 on a biocompatible frame 980.

The biocompatible frame 980 can be fabricated/constructed from liquid crystal polymers/polyimide/silica/silicon/silk/SU-8 resin/other suitable material.

Furthermore, if needed, the biocompatible frame 980 can be coated with a fluorinated silicon material to protect against water and/or oil.

The retinal contact lens biomodule subsystem 1180 can integrate: (a) a control circuitry component 1000, (b) an array of display pixels 1020, (c) an array of microlenses 1040, (d) a biosensor component 1060, (e) a biosensor read-out component 1080, (f) a solar cell component 1120, (g) a micropatch component 1140, (h) a low-power wireless (radio) transmitter (with an antenna) component 1160 and (g) an electrical power providing component (e.g., a printed thin-film battery) 400, utilizing a connecting electrical contact layer 1100.

Multi-layers of positive electrical charged ferritin protein, separated by a layer of nanocrystals, from multi-layers of negative electrical charged ferritin protein—sandwiched between two (2) transparent metal electrodes on a biocompatible substrate (e.g., silk) can act as the solar cell component 1120.

Printed Electronics Over a Three-Dimensional (3-D) Structure for Miniaturization/Manufacturing of the Retinal Contact Lens Biomodule Subsystem 1180

Furthermore, printed electronics can print a section of the retinal contact lens biomodule subsystem 1180 over a three-dimensional (3-D) structure, instead of assembling many discrete components. Higher level of miniaturization and manufacturing can be realized, utilizing printed electronics (e.g., aerosol nanoparticle Jet to print an antenna, electronics circuitry, radio frequency component and sensor).

Furthermore, the retinal contact lens biomodule subsystem 1180 can be fabricated/constructed by lifting off the electronics circuit layer from a rigid semiconductor substrate and then bonding/connecting the lifted off electronics layer on nanoribbons of wires mounted onto a lightweight and stretchable membrane, wherein the wires can bend, twist and stretch, while maintaining their functionality.

Furthermore, the micropatch components 1140 can integrate a MEMS reservoir to store the bioactive compounds 100 and/or bioactive molecules 100A for a sustained delivery. The above retinal contact lens biomodule subsystem 1180 can enable a near real-time/real-time measurement of a disease specific biomarker and programmable/active delivery of the bioactive compounds 100 and/or bioactive molecules 100A in near real-time/real-time (via a dynamic closed feedback loop).

FIG. 16B illustrates a near real-time/real-time application of a wearable retinal contact lens biomodule subsystem 1180.

In the above disclosed specifications "/" has been used to indicate "or".

Any example in the above disclosed specifications is by way of an example and not by way of any limitation.

All the terms in the above disclosed specifications have a plain meaning for a person ordinary skilled in the art/subject matter.

The above disclosed specifications are the preferred embodiments of the present invention. However, they are not intended to be limiting only to the preferred embodiments of the present invention. Numerous variations and/or modifications are possible within the scope of the present invention.

We claim:

1. An optical biomodule for detecting a disease or plurality of diseases in a biological fluid, wherein the biological fluid comprises: a biomarker or plurality, of biomarkers, wherein the biomarker or the plurality of biomarkers indicate a presence or an absence of the disease or the plurality of diseases, comprising:
(a) an array of fluidic containers,
   wherein each fluidic container is a microcapillary,
   wherein each [fluidic container] microcapillary within the array of microcapillaries comprises:
   a first biomarker binder or a second biomarker binder,
      wherein the first biomarker binder comprises: an antibody or an aptamer or a synthetically designed protein,
      wherein the first biomarker binder is chemically coupled with a fluorophore or a quantum dot fluorophore,
   wherein the second biomarker binder comprises: a molecular beacon, wherein each microcapillary comprises: one or more three-dimensional (3-D) protruded structures at the bottom of each microcapillary for enhancing a fluorescence emission due to an interaction of the first biomarker binder or the second biomarker binder with a biomarker,
   wherein the one three-dimensional (3-D) protruded structure comprises: a metal thin-film,
   wherein shape or diameter or height, or pitch of the one three-dimensional (3-D) protruded structure is varied for maximum enhancement of the fluorescence emission,
   wherein more than the one three-dimensional (3-D) protruded structure is spaced or arranged in a two-dimensional (2-D) array,
   wherein the two-dimensional (2-D) array is a systematic arrangement of similar three-dimensional (3-D) protruded structures;
(b) a light source or an array of light sources directed at the array of microcapillaries for inducing the fluorescence emission due to an interaction of the first biomarker binder or the second biomarker binder with the biomarker in each microcapillary within the array of microcapillaries; and
(c) a device or an array of devices for detecting the fluorescence emission due to the interaction of the first biomarker binder or the second biomarker binder with the biomarker in each [fluidic container] microcapillary within the array of [fluidic containers] microcapillaries.

2. The optical biomodule according to claim 1, wherein each microcapillary within the array of microcapillaries is a recessed surface or a planar surface for placing the biological fluid.

3. The optical biomodule according to claim 1, further comprises a distinct first biomarker binder or a distinct second biomarker binder in each microcapillary within the array of microcapillaries.

4. The optical biomodule according to claim 1, wherein the light source or array of light sources is a coherent light source or an array of coherent light sources for inducing the fluorescence emission.

5. The optical biomodule according to claim 1, further comprises an array of optical fibers or an array of optical waveguides for transmitting the fluorescence emission in each microcapillary within the array of microcapillaries, to the device or the array of devices for detecting the fluorescence emission.

6. The optical biomodule according to claim 5, further comprises an array of optical filters for optical filtering the fluorescence emission in each microcapillary within the array of microcapillaries, prior to transmitting the fluorescence emission to the array of optical fibers or the array of optical waveguides.

7. The optical biomodule according to claim 5, further comprises an array of lenses for optical coupling the fluorescence emission in each microcapillary within the array of microcapillaries, prior to transmitting the fluorescence emission to the array of optical fibers or the array of optical waveguides.

8. The optical biomodule according to claim 1, wherein the device or the array of device for detecting fluorescence comprises a charged-coupled detector or a complementary metal-oxide-semiconductor (CMOS) detector, or an array of charged-coupled detectors or an array of complementary metal-oxide-semiconductor (CMOS) detectors for detecting the fluorescence emission in each microcapillary within the array of microcapillaries.

9. The optical biomodule according to claim 1, wherein the biomarker binder further comprises: a fluorescence amplifier or a nanoshell,
   wherein the fluorescence amplifier comprises the fluorophore or the quantum dot fluorophore,
   wherein the fluorescence amplifier further comprises one or more metal particles and a DNA,
   wherein the nanoshell comprises a metal barcode or an optical barcode.

10. The optical biomodule according to claim 9, wherein the nanoshell further comprises a paramagnetic nanoparticle.

11. The optical biomodule according to claim 1, further comprises an optical device for optical path switching of the fluorescence emission in each [fluidic container] microcapillary within the array of [fluidic containers] microcapillaries, prior to transmitting the fluorescence emission to the device or the array of devices for detecting the fluorescence emission.

* * * * *

UNITED STATES PATENT AND TRADEMARK OFFICE
CERTIFICATE OF CORRECTION

| | | |
|---|---|---|
| PATENT NO. | : 9,557,271 B2 | Page 1 of 1 |
| APPLICATION NO. | : 13/663376 | |
| DATED | : January 31, 2017 | |
| INVENTOR(S) | : Mohammad A. Mazed and Sayeeda Mazed | |

It is certified that error appears in the above-identified patent and that said Letters Patent is hereby corrected as shown below:

In the Claims

In Claim 1, Column 59, Line 24:
Please delete "[fluidic container]"
And insert --fluidic container--

In Claim 1, Column 59, Line 44:
Please delete "maximum"
And insert --a maximum--

In Claim 1, Column 60, Line 1:
Please delete "[fluidic container]"
And insert --fluidic container--

In Claim 1, Column 60, Line 2:
Please delete "[fluidic container]"
And insert --fluidic container--

In Claim 11, Column 60, Line 55:
Please delete "[fluidic container]"
And insert --fluidic container--

In Claim 11, Column 60, Line 56:
Please delete "[fluidic container]"
And insert --fluidic container--

Signed and Sealed this
Fourth Day of July, 2023

Katherine Kelly Vidal
*Director of the United States Patent and Trademark Office*